US008333754B2

United States Patent
Boyden et al.

(10) Patent No.: US 8,333,754 B2
(45) Date of Patent: *Dec. 18, 2012

(54) MEDICAL OR VETERINARY DIGESTIVE TRACT UTILIZATION SYSTEMS AND METHODS

(75) Inventors: Edward S. Boyden, Cambridge, MA (US); Roderick A. Hyde, Redmond, WA (US); Muriel Y. Ishikawa, Livermore, CA (US); Jordin T. Kare, Seattle, WA (US); Robert Langer, Newton, MA (US); Eric C. Leuthardt, St. Louis, MO (US); Dennis J. Rivet, Portsmouth, VA (US); Michael A. Smith, Phoenix, AZ (US); Charles Whitmer, North Bend, WA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 697 days.

This patent is subject to a terminal disclaimer.

(21) Appl. No.: 12/002,777

(22) Filed: Dec. 17, 2007

(65) Prior Publication Data

US 2009/0112191 A1 Apr. 30, 2009

Related U.S. Application Data

(63) Continuation-in-part of application No. 12/001,983, filed on Dec. 12, 2007, and a continuation-in-part of application No. 11/982,448, filed on Oct. 31, 2007.

(51) Int. Cl.
*A61K 9/22* (2006.01)
*A61J 7/00* (2006.01)
*A61M 31/00* (2006.01)

(52) U.S. Cl. ......... 604/891.1; 604/77; 604/79; 604/275; 604/514; 604/516

(58) Field of Classification Search ............... 604/890.1, 604/891.1, 275–279, 19, 21, 31, 503, 510, 604/514, 93.01, 97.03, 65, 164.05, 264, 528, 604/516, 77, 79, 270, 910
See application file for complete search history.

(56) References Cited

U.S. PATENT DOCUMENTS 4,096,238 A   6/1978   Zaffaroni et al.
(Continued)

FOREIGN PATENT DOCUMENTS

WO   WO 2006/077527 A2   7/2006
(Continued)

OTHER PUBLICATIONS

Duchene, D. et al.; "Pharmaceutical and Medical Aspects of Bioadhesive Systems for Drug Administration"; Drug Development and Industrial Pharmacy; 1988; pp. 283-318; vol. 14, No. 2 & 3; Marcel Dekker, Inc.

(Continued)

*Primary Examiner* — Kevin C Sirmons
*Assistant Examiner* — Bradley Thomas, Jr.

(57) ABSTRACT

Systems and methods are described for implementing or deploying medical or veterinary utility modules comprising a first module operable in a digestive or respiratory tract to engage a second module, optionally by a magnetic field. Alternatively or additionally, systems may be operable to remain in situ and also operable to permit a therapeutic material dispensation. In some contexts, for example, systems or methods may dispense a therapeutic material via a subject's throat or elsewhere in the digestive or respiratory tract.

23 Claims, 23 Drawing Sheets

U.S. PATENT DOCUMENTS

| | | | |
|---|---|---|---|
| 4,207,890 | A | 6/1980 | Mamajek et al. |
| 4,522,625 | A | 6/1985 | Edgren |
| 4,595,583 | A | 6/1986 | Eckenhoff et al. |
| 4,735,804 | A | 4/1988 | Caldwell et al. |
| 4,758,436 | A | 7/1988 | Caldwell et al. |
| 4,878,905 | A | 11/1989 | Blass |
| 4,925,446 | A * | 5/1990 | Garay et al. ............ 604/103.02 |
| 5,198,229 | A | 3/1993 | Wong et al. |
| 5,318,557 | A | 6/1994 | Gross |
| 5,354,264 | A * | 10/1994 | Bae et al. ........................ 604/21 |
| 5,576,025 | A | 11/1996 | Akiyama et al. |
| 5,797,898 | A | 8/1998 | Santini, Jr. et al. |
| 5,938,654 | A * | 8/1999 | Wong et al. ................ 604/892.1 |
| 6,120,803 | A | 9/2000 | Wong et al. |
| 6,240,312 | B1 | 5/2001 | Alfano et al. |
| 6,283,953 | B1 | 9/2001 | Ayer et al. |
| 6,285,897 | B1 | 9/2001 | Kilcoyne et al. |
| 6,358,197 | B1 | 3/2002 | Silverman et al. |
| 6,425,904 | B1 | 7/2002 | Lemelson |
| 6,428,813 | B1 | 8/2002 | Akiyama et al. |
| 6,475,521 | B1 | 11/2002 | Timmins et al. |
| 6,535,764 | B2 | 3/2003 | Imran et al. |
| 6,582,720 | B1 | 6/2003 | Inagi et al. |
| 6,632,655 | B1 | 10/2003 | Mehta et al. |
| 6,656,194 | B1 | 12/2003 | Gannoe et al. |
| 6,656,464 | B2 | 12/2003 | Kondo |
| 6,677,313 | B1 | 1/2004 | Mathiowitz et al. |
| 6,689,056 | B1 | 2/2004 | Kilcoyne et al. |
| 6,776,165 | B2 | 8/2004 | Jin |
| 6,797,268 | B2 | 9/2004 | Kodama et al. |
| 6,797,283 | B1 | 9/2004 | Edgren et al. |
| 6,911,004 | B2 | 6/2005 | Kim et al. |
| 6,929,636 | B1 | 8/2005 | von Alten |
| 6,939,290 | B2 * | 9/2005 | Iddan ............................ 600/109 |
| 6,942,771 | B1 | 9/2005 | Kayyem |
| 6,950,690 | B1 | 9/2005 | Meron et al. |
| 6,958,034 | B2 | 10/2005 | Iddan |
| 6,960,356 | B1 | 11/2005 | Talwar et al. |
| 6,994,095 | B2 | 2/2006 | Burnett |
| 7,016,735 | B2 | 3/2006 | Imran et al. |
| 7,020,531 | B1 * | 3/2006 | Colliou et al. ................ 607/133 |
| 7,033,322 | B2 | 4/2006 | Silver |
| 7,041,083 | B2 | 5/2006 | Chu et al. |
| 7,083,578 | B2 | 8/2006 | Lewkowicz et al. |
| 7,097,851 | B1 | 8/2006 | Takada |
| 7,105,300 | B2 | 9/2006 | Parce et al. |
| 7,105,810 | B2 | 9/2006 | Kameoka et al. |
| 7,160,258 | B2 | 1/2007 | Imran et al. |
| 7,182,957 | B2 | 2/2007 | Zentner et al. |
| 7,220,237 | B2 | 5/2007 | Gannoe et al. |
| 7,353,067 | B1 | 4/2008 | Helland et al. |
| 7,654,985 | B2 * | 2/2010 | Dinsmoor et al. ............ 604/174 |
| 7,857,767 | B2 * | 12/2010 | Ferren et al. .................. 600/481 |
| 2002/0012651 | A1 | 1/2002 | Loeb |
| 2002/0055734 | A1 | 5/2002 | Houzego et al. |
| 2002/0129443 | A1 | 9/2002 | Di Cecco |
| 2002/0137803 | A1 | 9/2002 | Kirkland |
| 2002/0151776 | A1 | 10/2002 | Shawgo et al. |
| 2002/0173770 | A1 | 11/2002 | Flory et al. |
| 2003/0092964 | A1 | 5/2003 | Kim et al. |
| 2003/0113371 | A1 | 6/2003 | Dhawan et al. |
| 2003/0191476 | A1 | 10/2003 | Smit |
| 2003/0216622 | A1 | 11/2003 | Meron et al. |
| 2003/0232078 | A1 | 12/2003 | Dong et al. |
| 2004/0109894 | A1 | 6/2004 | Shefer et al. |
| 2004/0214311 | A1 | 10/2004 | Levy |
| 2004/0220498 | A1 | 11/2004 | Li et al. |
| 2004/0224019 | A1 | 11/2004 | Shefer et al. |
| 2004/0236180 | A1 | 11/2004 | Uchiyama et al. |
| 2004/0260346 | A1 | 12/2004 | Overall et al. |
| 2005/0019407 | A1 | 1/2005 | Sowden et al. |
| 2005/0037312 | A1 | 2/2005 | Uchida |
| 2005/0058701 | A1 | 3/2005 | Gross et al. |
| 2005/0060030 | A1 | 3/2005 | Lashinski et al. |
| 2005/0064027 | A1 | 3/2005 | Jacob et al. |
| 2005/0100937 | A1 | 5/2005 | Holmes |
| 2005/0147559 | A1 | 7/2005 | von Alten |
| 2005/0158246 | A1 | 7/2005 | Takizawa et al. |
| 2005/0165272 | A1 | 7/2005 | Okada et al. |
| 2005/0201974 | A1 | 9/2005 | Schestopol et al. |
| 2005/0222537 | A1 | 10/2005 | Dinsmoor et al. |
| 2005/0234399 | A1 | 10/2005 | Wood et al. |
| 2005/0245906 | A1 | 11/2005 | Makower et al. |
| 2005/0246037 | A1 | 11/2005 | Starkebaum |
| 2005/0249799 | A1 | 11/2005 | Jacob et al. |
| 2005/0277912 | A1 | 12/2005 | John |
| 2006/0003007 | A1 | 1/2006 | Odidi et al. |
| 2006/0045865 | A1 | 3/2006 | Jacob et al. |
| 2006/0062852 | A1 | 3/2006 | Holmes |
| 2006/0063974 | A1 | 3/2006 | Uchiyama et al. |
| 2006/0099245 | A1 | 5/2006 | Kumar et al. |
| 2006/0152309 | A1 | 7/2006 | Mintchev et al. |
| 2006/0157067 | A1 | 7/2006 | Saadat et al. |
| 2006/0167339 | A1 | 7/2006 | Gilad et al. |
| 2006/0182738 | A1 | 8/2006 | Holmes |
| 2006/0190019 | A1 | 8/2006 | Gannoe et al. |
| 2006/0195015 | A1 | 8/2006 | Mullick et al. |
| 2006/0241718 | A1 | 10/2006 | Tyler et al. |
| 2006/0248698 | A1 | 11/2006 | Hanson et al. |
| 2006/0289640 | A1 | 12/2006 | Mercure et al. |
| 2007/0080658 | A1 | 4/2007 | Farritor et al. |
| 2007/0088334 | A1 | 4/2007 | Hillis et al. |
| 2007/0106213 | A1 | 5/2007 | Spera et al. |
| 2007/0161851 | A1 | 7/2007 | Takizawa et al. |
| 2007/0178160 | A1 | 8/2007 | Burnett |
| 2007/0213659 | A1 | 9/2007 | Trovato et al. |
| 2007/0219405 | A1 | 9/2007 | Uchiyama et al. |
| 2007/0225576 | A1 | 9/2007 | Brown et al. |
| 2007/0244388 | A1 | 10/2007 | Sato et al. |
| 2007/0253761 | A1 | 11/2007 | May |
| 2007/0255100 | A1 | 11/2007 | Barlow et al. |
| 2007/0265496 | A1 | 11/2007 | Kawano et al. |
| 2008/0194912 | A1 | 8/2008 | Trovato et al. |
| 2008/0214619 | A1 * | 9/2008 | Wolfe et al. .................... 514/338 |
| 2009/0306633 | A1 | 12/2009 | Trovato et al. |

FOREIGN PATENT DOCUMENTS

WO    WO 2007/013059 A2    2/2007

OTHER PUBLICATIONS

Quirini, Marco et al.; "Design of a Pill-Sized 12-Legged Endoscopic Capsule Robot"; IEEE International Conference on Robotics and Automation in Rome, Italy; Apr. 10-14, 2007; pp. 1856-1862; vol. ThA7.2; IEEE.

Rentschler, Mark E. et al.; "Natural Orifice Surgery With an Endoluminal Mobile Robot"; SAGES Meeting; 2006; pp. 1-14; located at: http://robots.unl.edu/Files/Papers2/Rentschler_Natural_Orifice_Robot_with_figures.pdf.

Excerpt from the American Heritage Dictionary of the English Language; bearing a date of 2009; Printed on Jan. 19, 2011; located at: http://education.yahoo.com/reference/dictionary/entry/moor: total of 2 pages.

* cited by examiner

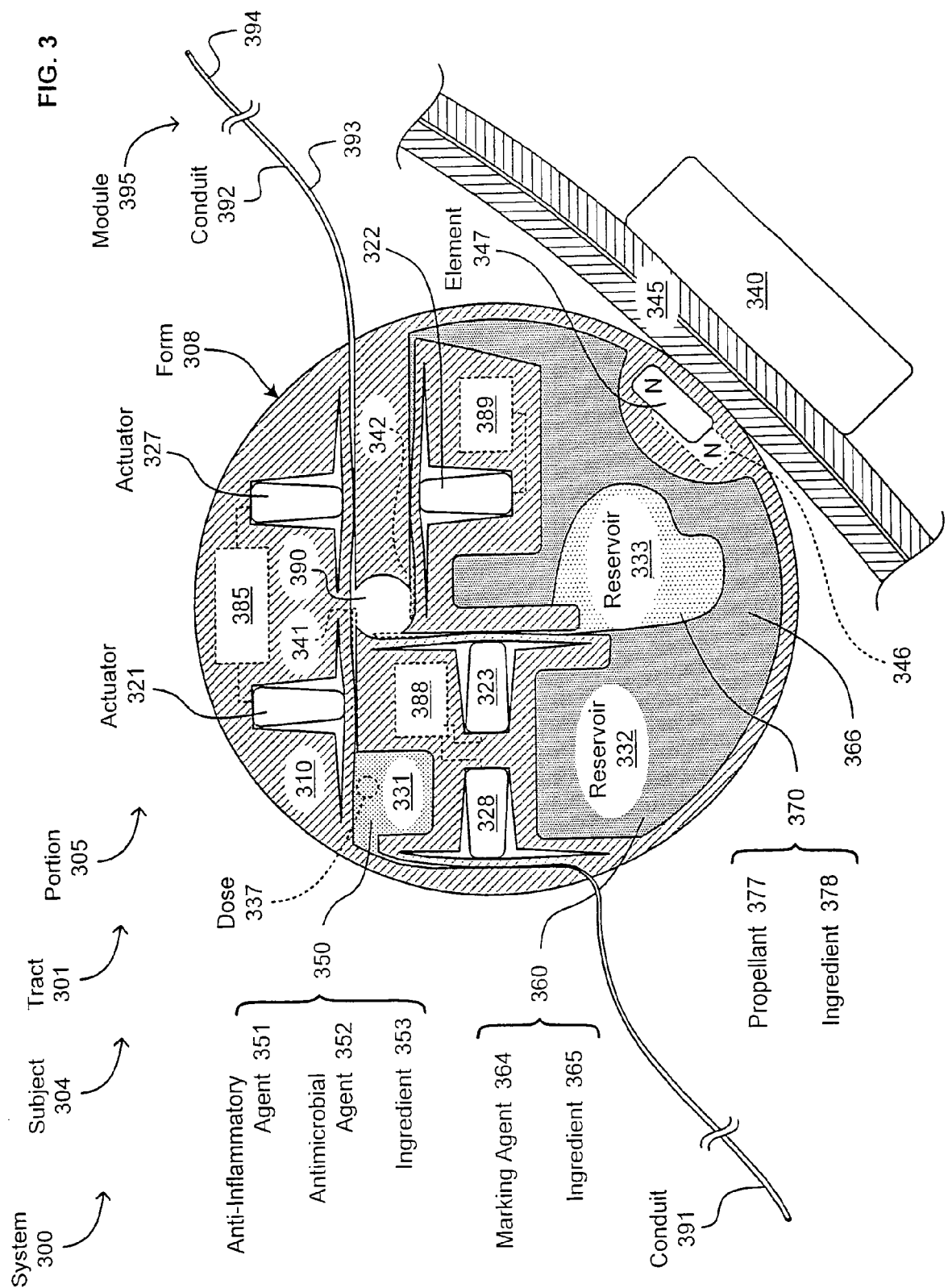

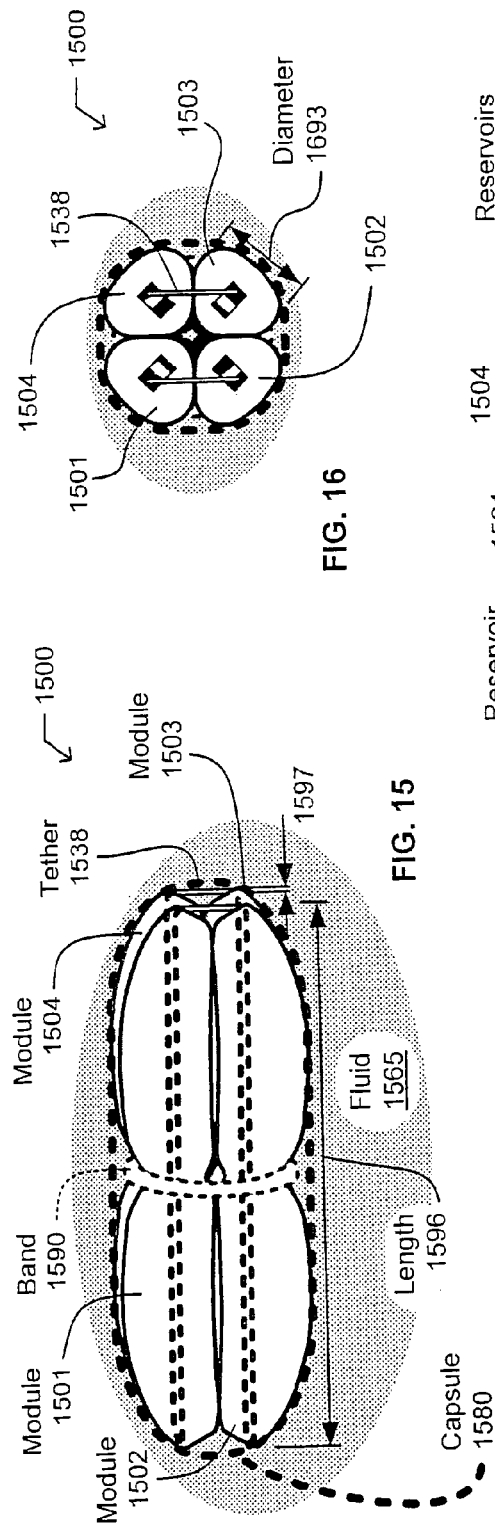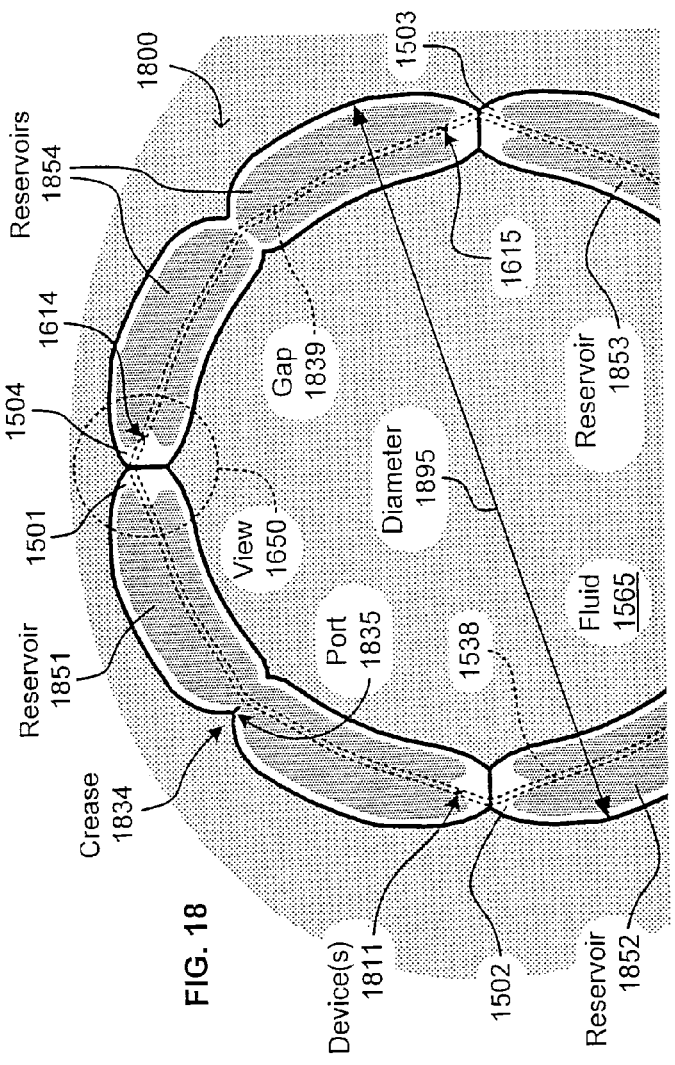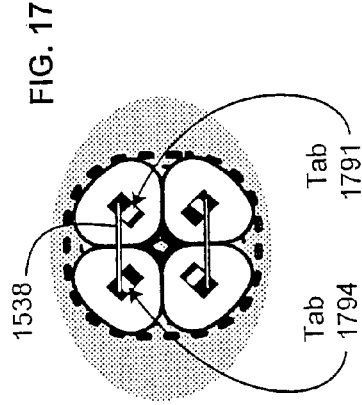

MEDICAL OR VETERINARY DIGESTIVE TRACT UTILIZATION SYSTEMS AND METHODS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 12/001,983, entitled MEDICAL OR VETERINARY DIGESTIVE TRACT UTILIZATION SYSTEMS AND METHODS, naming Edward S. Boyden, Roderick A.; Hyde, Muriel Y. Ishikawa, Jordin T. Kare, Robert Langer, Eric C. Leuthardt, Dennis J. Rivet, Michael A. Smith, Charles Whitmer, Lowell L. Wood, Jr. and Victoria Y. H. Wood as inventors, filed 12 Dec. 2007, which is currently co-pending, or is an application of which a currently co-pending application is entitled to the benefit of the filing date.

For purposes of the USPTO extra-statutory requirements, the present application constitutes a continuation-in-part of U.S. patent application No. 11/982,448, entitled MEDICAL OR VETERINARY DIGESTIVE TRACT UTILIZATION SYSTEMS AND METHODS, naming Edward S. Boyden, Roderick A. Hyde, Muriel Y. Ishikawa, Jordin T. Kare, Robert Langer, Eric C. Leuthardt, Dennis J. Rivet, Michael A. Smith, Charles Whitmer, Lowell L. Wood, Jr. and Victoria Y. H. Wood as inventors, filed 31 Oct. 2007, which is currently co-pending, or is an application of which a currently co-pending application is entitled to the benefit of the filing date. The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

In one aspect, a system includes but is not limited to a first module operable in a digestive or respiratory tract to engage a second module at least magnetically; and one or more magnetic-flux-generating elements operable to diminish a disengagement force between the first module and the second module by removing at least 0.1% of a magnetic flux passing from the first module into the second module. In addition to the foregoing, other system aspects are described in the claims, drawings, and text forming a part of the present disclosure.

In one aspect, a system includes but is not limited to a magnetically manipulable module operable to remain within a digestive or respiratory tract of a subject for more than a day and to permit a therapeutic material dispensation therein from the magnetically manipulable module. In addition to the foregoing, other system aspects are described in the claims, drawings, and text forming a part of the present disclosure.

In one aspect, a system includes but is not limited to a module operable to remain in a digestive or respiratory tract of a subject for more than a day and to dispense a first therapeutic material responsive to a first device state and a second therapeutic material responsive to a second device state. In addition to the foregoing, other system aspects are described in the claims, drawings, and text forming a part of the present disclosure.

In one aspect, a system includes but is not limited to a first module operable to contain a first therapeutic material within a digestive or respiratory tract; and one or more artificial conduits operable to guide the first therapeutic material in a first flow from the first module at least into a throat of the digestive or respiratory tract. In addition to the foregoing, other system aspects are described in the claims, drawings, and text forming a part of the present disclosure.

In one aspect, a system includes but is not limited to one or more sensor-containing modules each small enough to pass through a digestive tract; a mooring module operable to remain in the digestive tract for more than a day; and one or more tethers configured to establish an effective range of motion of the one or more sensor-containing modules relative to the mooring module within the digestive tract. In addition to the foregoing, other system aspects are described in the claims, drawings, and text forming a part of the present disclosure.

In one or more various aspects, related systems include but are not limited to circuitry and/or programming for effecting herein-referenced method aspects; the circuitry and/or programming can be virtually any combination of hardware, software, and/or firmware configured to effect the herein-referenced method aspects depending upon the design choices of the system designer. In addition to the foregoing, various other method and/or system aspects are set forth and described in the teachings such as text (e.g., claims and/or detailed description) and/or drawings of the present disclosure.

The foregoing is a summary and thus contains, by necessity, simplifications, generalizations and omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE FIGURES

FIGS. 3-28 depict respective contexts in which one or more medical or veterinary technologies as described herein may be implemented.

DETAILED DESCRIPTION

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In the following detailed description, reference is made to the accompanying drawings, which form a part hereof. The use of the same symbols in different drawings typically indicates similar or identical items. The illustrative embodiments described in the detailed description, drawings, and claims are not meant to be limiting. Other embodiments may be utilized, and other changes may be made, without departing from the spirit or scope of the subject matter presented here.

Figure 1:
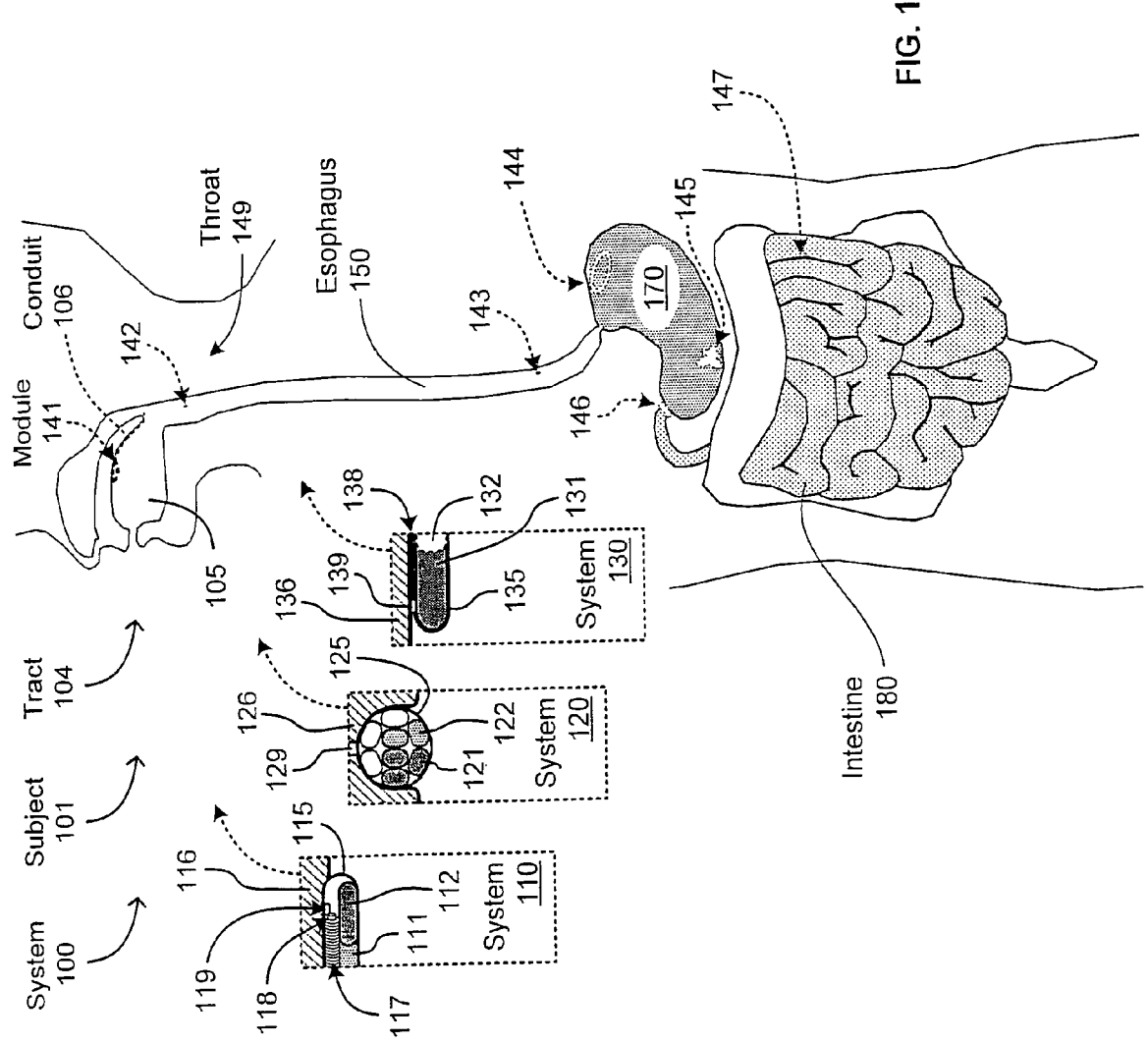
FIG. 1 depicts an exemplary environment in which one or more technologies may be implemented.

With reference now to FIG. 1, shown is a system 100 in which one or more technologies may be implemented. System 100 may include one or more local modules 141, 142, 143, 144, 145, 146, 147 positioned along a digestive/respiratory tract 104. In some contexts, such local modules 141-146 may comprise or otherwise be supported by one or more surgical staples, helical anchors, other piercing anchors, bioadhesives, or other such durable modes of attachment for controllable and/or extended functionality. Such bioadhesives, in some embodiments, may comprise a mixture of poloxamer 407 with polycarbophil, or some similar gel-forming liquid. Other such liquid-based bioadhesives may include, for example, polycarbophil or polyacrylic acid secreted via one or more ports of a local or other utility module as described herein.

Figure 9:
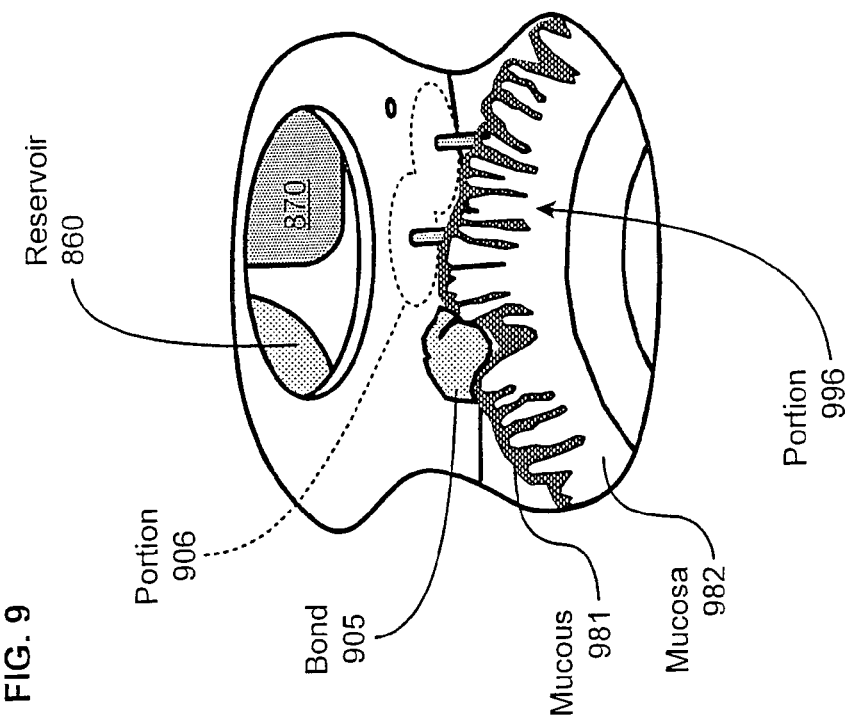

In some embodiments, one or more such local modules 141-147 are small enough to pass through tract 104 per vias naturales, and include at least a wireless-control component responsive to a received signal. Alternatively or additionally, any such local modules 141-147 may, in some variants, include a body with a protruding surface narrow enough to be positioned adjacent to a mucous membrane. See, e.g., FIG. 5. Alternatively or additionally, any such local modules 141-147 and/or utility modules may, in some variants, be configured with more than one adhesive or other attachment feature so as to facilitate sequential or otherwise redundant modes of attachment. See, e.g., FIGS. 7-9. Alternatively or additionally, any such local modules 141-147 may, in some variants, be configured to facilitate a "primary" material supply deployable within gastric compartment 170 for an extended and/or controllable period, but operable for dispensing elsewhere. See, e.g., FIG. 10. Alternatively or additionally, any such local modules may comprise adaptable extender module at least partly supported by a subject's head or neck, for facilitating an extended or controllable placement of one or more such local modules 141-147. Alternatively or additionally, one or more such sensor-containing utility modules 141-147 may be tethered or otherwise moored so as to remain in a specific portion of a subject's mouth 105, throat 149, esophagus 150, gastric compartment 170, or intestine 180 for up to a day or more. In some variants, moreover, any of the herein-described modules may likewise be configured to include one or more wireless-control components for use in response to or otherwise in cooperation with a received wireless signal. See, e.g., U.S. patent application Ser. No. 10/536,126, titled "Adaptive Dispensation in a Tract," filed 23 Oct. 2007, also by Boyden et al., incorporated by reference to the extent not inconsistent herewith.

Alternatively or additionally, system 100 may include one or more instances of system 110, comprising one or more therapeutic materials 111, 112 borne in one or more modules 115 operable to be magnetically or otherwise supported by another module 116 such as the local module(s) 141-147. An instance of system 110 may, for example, comprise one or more modules 115 operable to contain a composition or other therapeutic material 111 within mouth 105 and one or more artificial conduits 106 operable to guide the therapeutic material 111 in a flow from the module(s) 115 through or otherwise into throat 149. In some instances, alternatively or additionally, module 115 may be operable to engage module 116 at least magnetically in a context in which one or more magnetized elements of ferromagnetic material 118 are operable to diminish a disengagement force between them by removing at least about 0.1% or a majority of a magnetic flux passing from module 115 into (at least a flux-guiding portion of) module 116. Alternatively or additionally, system 110 may be configured so that module 115 includes ferromagnetic material 118, a conductive coil 117, or other elements configured so that module 115 (a) is magnetically manipulable, (b) operable to remain within a tract of a subject for more than a day, and (c) operable to permit a dispensation of one or more therapeutic materials 111, 112. Any of these variants may occur, for example, in a context in which module 116 is implemented as a dental prosthetic (e.g. as module 141), between a subject's gums and cheeks, within a subject's nasal passages or throat, or at some other directly accessible portion of tract 104. In some variants, for example, control circuitry 119 within module 115 is operable to sense physical parameters, to apply one or more logical criteria, and/or to supply current through conductive coil 117 as described herein or known by those skilled in the art.

Alternatively or additionally, system 100 may include one or more instances of system 120, comprising one or more therapeutic materials 121, 122 borne in one or more modules 125 operable to be friction-fit (e.g. gripped) or otherwise supported by another module 126 such as local modules 141-147. In some embodiments in which local module 142 implements module 126 in throat 149, for example, an instance of system 120 may comprise module 125 operable to remain in a tract of a subject for more than a day and to dispense a first therapeutic material 121 responsive to a first device state and another therapeutic material 122 responsive to another device state. Control circuitry 129 may contain digital logic operable for dispensing therapeutic materials selectively, for example, responsive to sensor signals, timing logic, wireless signals, or other functional inputs as described herein. See, e.g., FIGS. 22-23 below. In embodiments in which local module 141 implements module 126, alternatively or additionally, system 100 may comprise module 125 operable to contain one or more therapeutic materials 121 within a subject's mouth and one or more artificial conduits 106 operable to guide the therapeutic material(s) in one or more flows from module 125 at least into throat 149.

Alternatively or additionally, system 100 may include one or more instances of system 130, comprising one or more therapeutic materials 131, 132 borne in one or more modules 135 operable to be adhesed or otherwise supported by another module 136 such as local modules 141-147. In some embodiments in which module 136 resides on a mucous membrane of mouth 105, for example, an instance of system 130 may comprise module 135 operable to remain in a tract 104 of a subject for more than a day and to dispense a first therapeutic material 131 responsive to a first device state and a second therapeutic material 132 responsive to a second device state. Control circuitry 139 may contain digital logic operable for dispensing therapeutic materials selectively, for example, responsive to sensor signals, timing logic, wireless signals, or other functional inputs as described herein. See, e.g., FIGS. 22-23 below. Alternatively or additionally, an instance of system 130 may comprise module 135 supported by module 136 via a magnetic coupling or adhesive 138, operable to remain within tract 104 of a human or other subject for more than a day and to permit at least a dispensation of therapeutic material 131 therein. In some contexts, module 135 may comprise a permanent magnet or other magnetically manipulable module configured to be attracted to one or more local modules 144, 145 resident within gastric compartment 170 or elsewhere within tract 104. In others, module 135 may attract itself to a module 146 adjacent tract 104. In many such variants, system 130 may (optionally) comprise module 135 operable in tract 104 to engage another module 141-147 at least magnetically and one or more magnetic-flux-generating element operable to remove at least 0.1% of magnetic flux passing from module 135 to module 136. Many existing electromagnets are powerful enough and safe for serving this function outside the subject, for example, causing or otherwise facilitating a disengagement.

Figure 2:
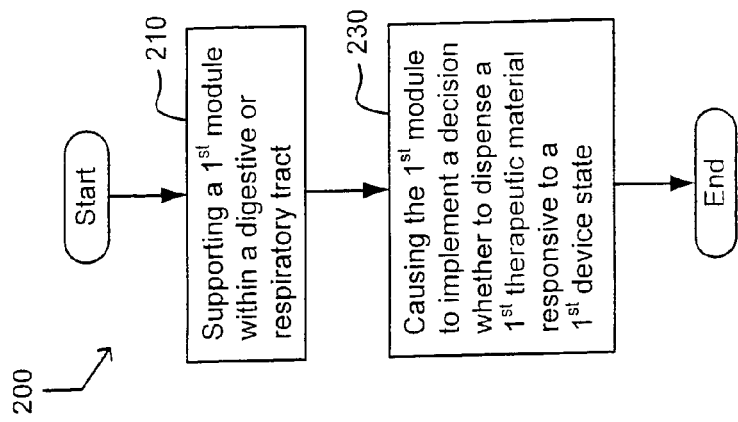
FIG. 2 depicts a high-level logic flow of an operational process.

With reference now to FIG. 2, shown is a flow 200 comprising operation 210—supporting a first module within a digestive or respiratory tract—and operation 230—causing the first module to implement a decision whether to dispense a first therapeutic material responsive to a first device state. In some embodiments that include one or more therapeutic materials, for example, a utility module and/or local modules 141-147 as described herein may (optionally) be configured to perform flow 200. In the context of system 130, for example, control circuitry 139 may perform operation 230 so that a therapeutic composition or other material 131 is dispensed according to an original regimen so long as module 136 remains in a "normal" mode. In some contexts, however, a second regimen may be used in response to a wireless signal or other indication to control circuitry 139, for example, that an increased dosage should be used. Alternatively or additionally, system 100 may be implemented so that a therapeutic-material-containing module 115, 125, 135 is configured to remain adjacent a local module 142-147 until prompted to depart per vias naturales by corresponding control circuitry 119, 129, 139. In some variants, such control circuitry may likewise be configured to cause an introduction of one or more other therapeutic materials 112, 122 or otherwise to update a subject's regimen of the first therapeutic material.

With reference now to FIG. 3, shown is portion 305 of a digestive or respiratory tract 301 of a mammal or other subject 304 in a vicinity of which one or more technologies may be implemented. System 300 may comprise one or more instances of modules 310 operable to remain within tract 301 for more than a day and to permit a first therapeutic material dispensation therein from the magnetically manipulable module 310. Alternatively or additionally, in various implementations, module 310 may be configured to be operable to remain in a throat 149 or other local portion 305 of tract 104 for more than an hour, a day, or a week.

In some variants, for example, module 310 can have a spherical or elongate form 308 small enough to pass through a digestive tract per vias naturales. Altenatively or additionally, module 310 may include one or more reservoirs 331 containing more than one therapeutically effective dose 337 of one or more of an anti-inflammatory agent 351, an antimicrobial agent 352, or some other therapeutic material 350 (optionally with one or more other ingredients 353).

Module 310 may also include one or more other reservoirs 332 containing more than one dispensation of an artificial marker 360. Material 360 may include a type and concentration of a dye or other marking agent 364 (optionally with one or more other therapeutic or other useful ingredients 365 as described herein) in a sufficient concentration to permit optical detection via one or more sensors in tract 301. In some variants, alternatively or additionally, reservoir 332 may comprise a gaseous material 366 at a higher-than-ambient pressure or other suitable energy source. Module 310 may likewise include one or more reservoirs 333 containing another (liquid and/or gaseous) fluid-containing propellant 377, optionally with one or more other ingredients 378 with medical utility as described herein. This can occur, for example, in a context in which control logic 388 causes actuator 328 to withdraw (rightward as shown) enough so that material 350 advances into portion 305 of tract 301.

As shown, module 310 may include one or more dispensing chambers 390 operable for combining fluid-containing propellant 377 at a higher-than-ambient pressure with one or more of a portion 341 of the therapeutic material 350 from the first reservoir 331 or (b) a portion 342 of the artificial marker 360. This can occur, for example, in a context in which control logic 385 causes actuator 321 to withdraw (upward as shown) enough so that at least portion 341 of material 350 advances into chamber 390. Alternatively or additionally, control logic 389 may be configured to cause actuator 322 to withdraw (downward as shown) enough so that at least portion 342 of material 360 advances into chamber 390. Alternatively or additionally, control logic 388 may be configured to signal actuator 323 to withdraw (leftward as shown) enough so that some of material 360 advances into chamber 390. In some contexts, such configurations of control logic 388, 389 define respective states of logic components therein and/or valves or other structures as described herein.

In some variants, control logic 388, 389 may be implemented integrally with control logic 385, for example, which may also control the position or magnetic configuration of one or more magnetic-flux-generating elements 346. Alternatively or additionally, control logic 385 may control an actuator 327 operable for initiating or regulating dispensations from dispensing chamber 390 via conduit 392.

Alternatively or additionally, module 310 may be configured to be magnetically manipulable, such as by the inclusion of one or more magnetic-flux-generating elements 347 operable for holding module 310 in an intestine or other portion 305 of the digestive or respiratory tract 301. In some such variants, module 310 may further include one or more electrically conductive coils or other opposing elements 346 operable for opposing at least some magnetic flux from magnetic-flux-generating element 347. In some contexts described herein, system 300 may further include one or more other modules 340 including at least some ferromagnetic material so that element 347 is effectively supported thereby within portion 305, optionally through a mucous membrane or other tissue 345 of subject 304. System 300 may further comprise two or more artificial conduits 391, 392 each operable to guide a material flow in the digestive or respiratory tract 301 as shown, one or more of the conduits 391, 392 optionally exceeding 10 centimeters.

In some variants, for example, module 395 includes a conduit segment 393 local to module 310 and extends to a conduit segment 394 distal to module 310. In embodiments shown at FIGS. 14, 20, 27, for example, such extension reaches into (and sometimes through) a throat of the digestive or respiratory tract. In embodiments like those of FIGS. 20, 27, such conduits likewise reach at least into an esophagus 150 of a digestive or respiratory tract 104. In embodiments like those of FIGS. 10, 20, 21, 27, such conduits likewise extend at least out of a gastric compartment (from reservoirs resident in an oral cavity or gastric compartment, for example) and/or into an intestine of a digestive tract.

Figure 4:
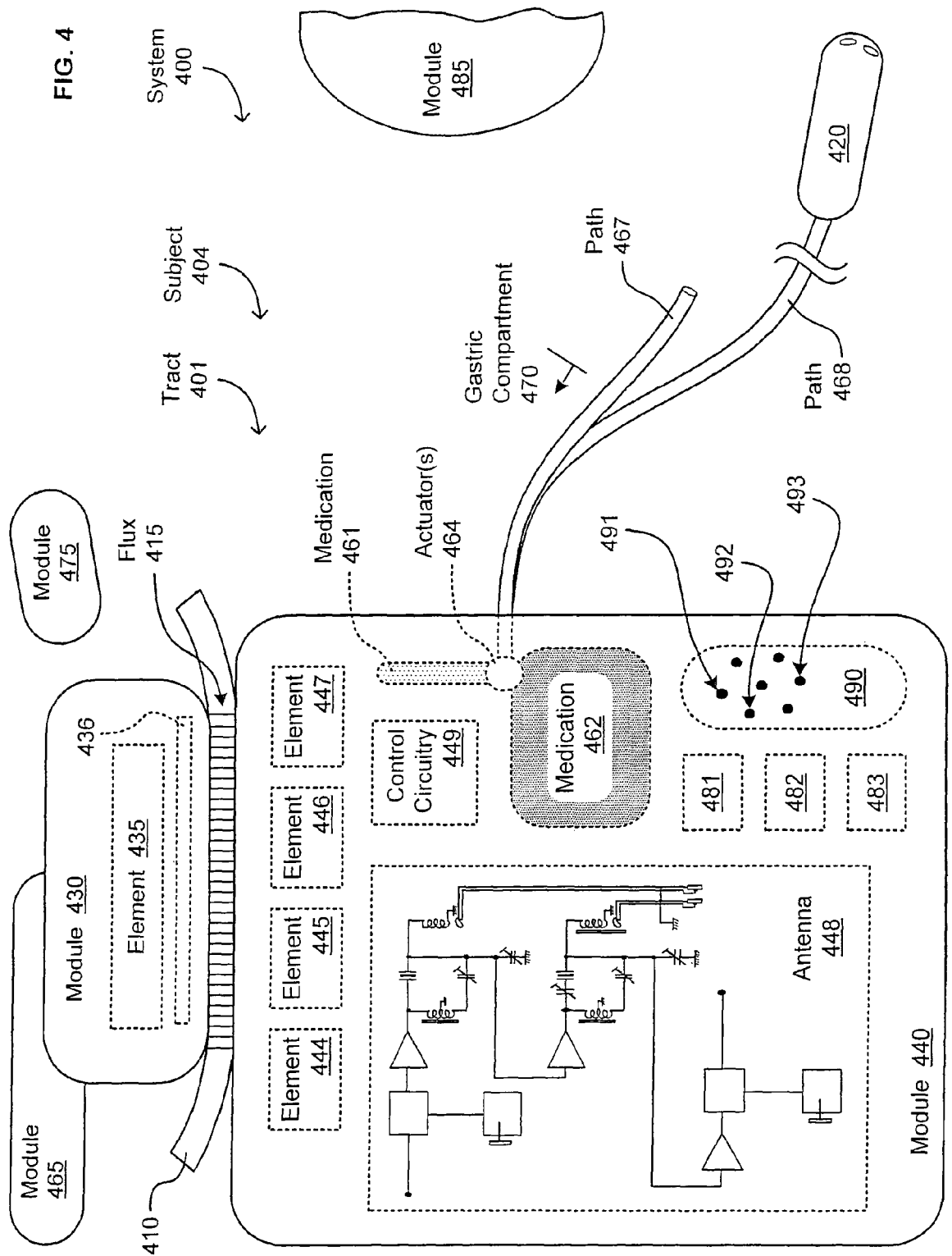

With reference now to FIG. 4, shown is a mammal or other subject 404 in a vicinity of which one or more technologies may be implemented. System 400 may comprise one or more instances of modules 440 operable in a digestive or respiratory tract 401 to engage another module 430 at least magnetically, within or adjacent tract 401 and/or subject 404. System 400 may further comprise one or more instances of magnetic-flux-generating elements 436 operable to diminish a disengagement force between the modules 430, 440 by removing at least 0.1% of a magnetic flux 415 passing from module 440 (optionally via layer 410) into module 430. Alternatively or additionally, module 440 may include one or more (magnetic-flux-generating) elements 445, 446 or other flux-guiding elements 444, 447 likewise operable for such a removal. This can be accomplished, for example, by moving such elements 444, 445 or modifying an electrical current through one or more of them so as to change their magnetic configuration. In some variants, for example, one or more such elements 436, 446 may be operable for bearing a current pulse of sufficient magnitude to demagnetize other such elements 435, 445 at least partially, as described herein.

Alternatively or additionally, module 440 may include one or more instances of antennas 448; anti-hyperglycemic-medications 461 or other medications 462 (optionally including a polymer-containing binding agent or other ingredients as well); material flow paths 467 of about one centimeter or longer, sufficiently long to bear such anti-hyperglycemic-medications 461 or other medications 462 through or otherwise out of gastric compartment 470; one or more actuator(s) 464 operable for releasing such medications selectively into one or more paths 467, 468; one or more sensors 491, 492 or dispensers 493 optionally comprising one or more modules 490; measurement data 481, dispensation-status-indicative data 482, or other data 483.

Alternatively or additionally, system 400 may further comprise control circuitry 449 for selectively activating at least one of the one or more actuators 464 operable for one or more of (a) releasing the anti-hyperglycemic-medication 461 into material flow path 467, (b) releasing an antimicrobial agent, adhesive, hormone, or other material into material flow path 467, (c) releasing medication 462 into a material flow path 468 (of another module 420) extending out of gastric compartment 470, or other timely dispensation operations defined in a physician-defined regimen profile or other data 483. System 400 may likewise comprise a remote module 485 operable for receiving dispensation-status-indicative data 482 from module 440 and/or one or more other modules 465, 475 (optionally) operable to support the second module 430 indirectly for more than a month in tract 401.

Figure 5:
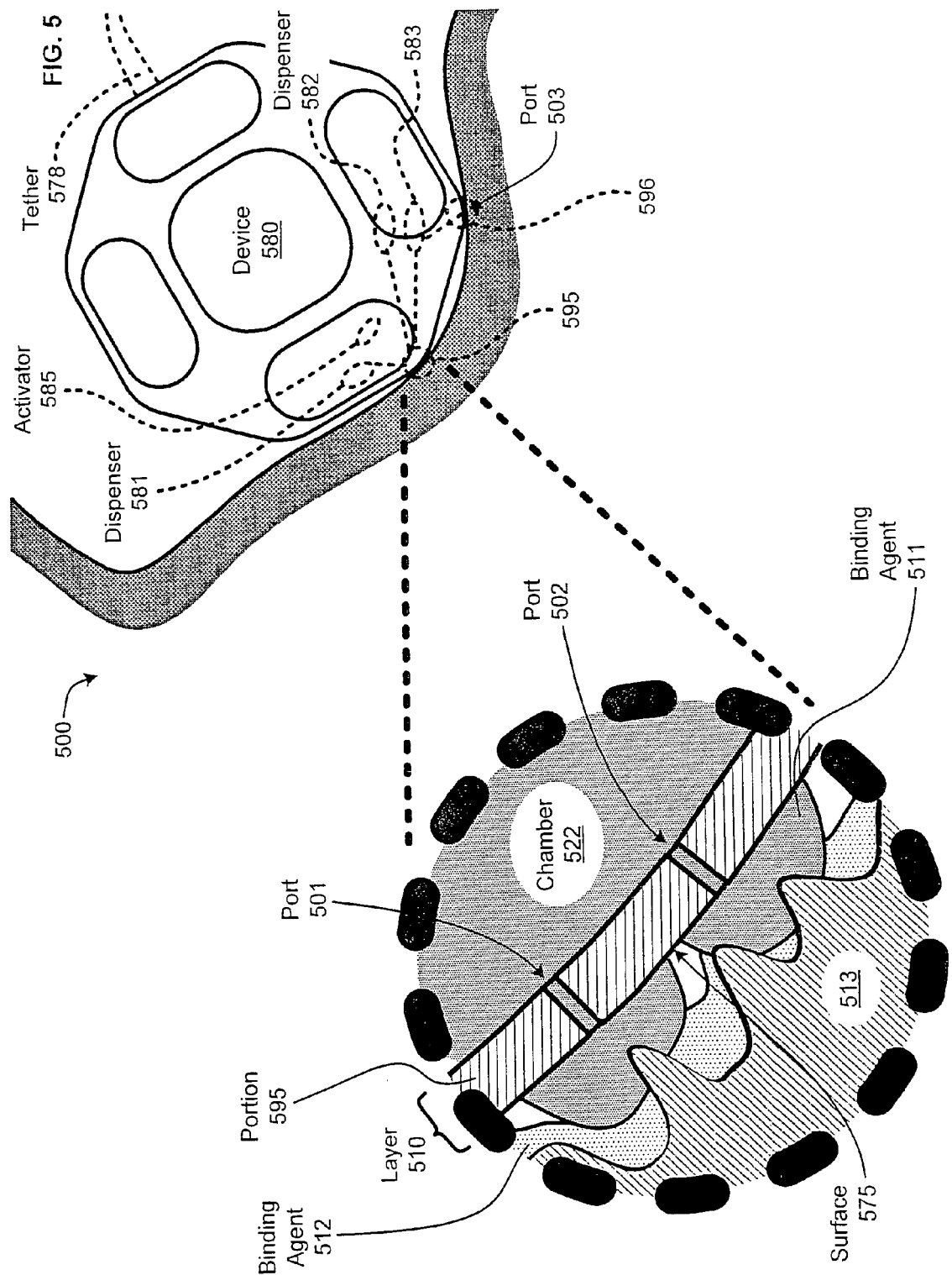

With reference now to FIG. 5, shown is a medical or veterinary system 500 in which one or more technologies may be implemented. System 500 may include one or more local modules or other devices 580 having a protruding surface 575 narrow enough to be positioned adjacent to a portion 595 of a mucous membrane 513, a first secretion port 501 (from dispenser 581, for example) operable for binding at least to a portion 595 of the protruding surface 575 of layer 510 as shown; and at least one other secretion port 502 (at least from dispenser 583 via chamber 522, for example) operable for binding at least to the adjacent portion 595 of the mucous membrane 513. In some variants, as shown, one or more binding agents 512 secreted via at least the second secretion port 502 also bind to another binding agent 511, directly to mucosa, or to other structures described herein. Alternatively or additionally, device 580 may include one or more other dispensers 582, magnetic or other flux-guiding elements, one or more activators 585 (using heat or light to activate a binding agent, for example), or tethers 578 or other supported structures as described herein. In some variants, device 580 may likewise include one or more other protruding surfaces 575 narrow enough to be positioned adjacent to another portion 596 of the mucous membrane 513, optionally having one or more other ports 503 operable for facilitating adhesion therebetween. Such adhesives may include surgical adhesive such as cyanoacrylates or their derivatives, or any other sufficiently adhesive compound (with sufficiently low toxicity to intra-luminal cells) for a specified observational and/or therapeutic interval. Other suitable binding agents may include fibrin glues, any number of glues based on collagen or gelatin, or other such biologically mediated binding agents. Still others may comprise one or more erodible polymers selected from the group consisting of soluble cellulosic materials, ethylene vinyl alcohol, ethylene maleic anhydride copolymer, polyacrylates, polycaprolactones, inorganic glass based on polyphosphates and fused salts, polyanhydrides, poly (ortho)esters, biodegradable polyurethanes, polyvinyl pyrrolidone, polyactones, polyamides and polypeptides, gelatin and derivatives, polyacrylonitriles, polyesters, and combinations thereof.

Figure 6:
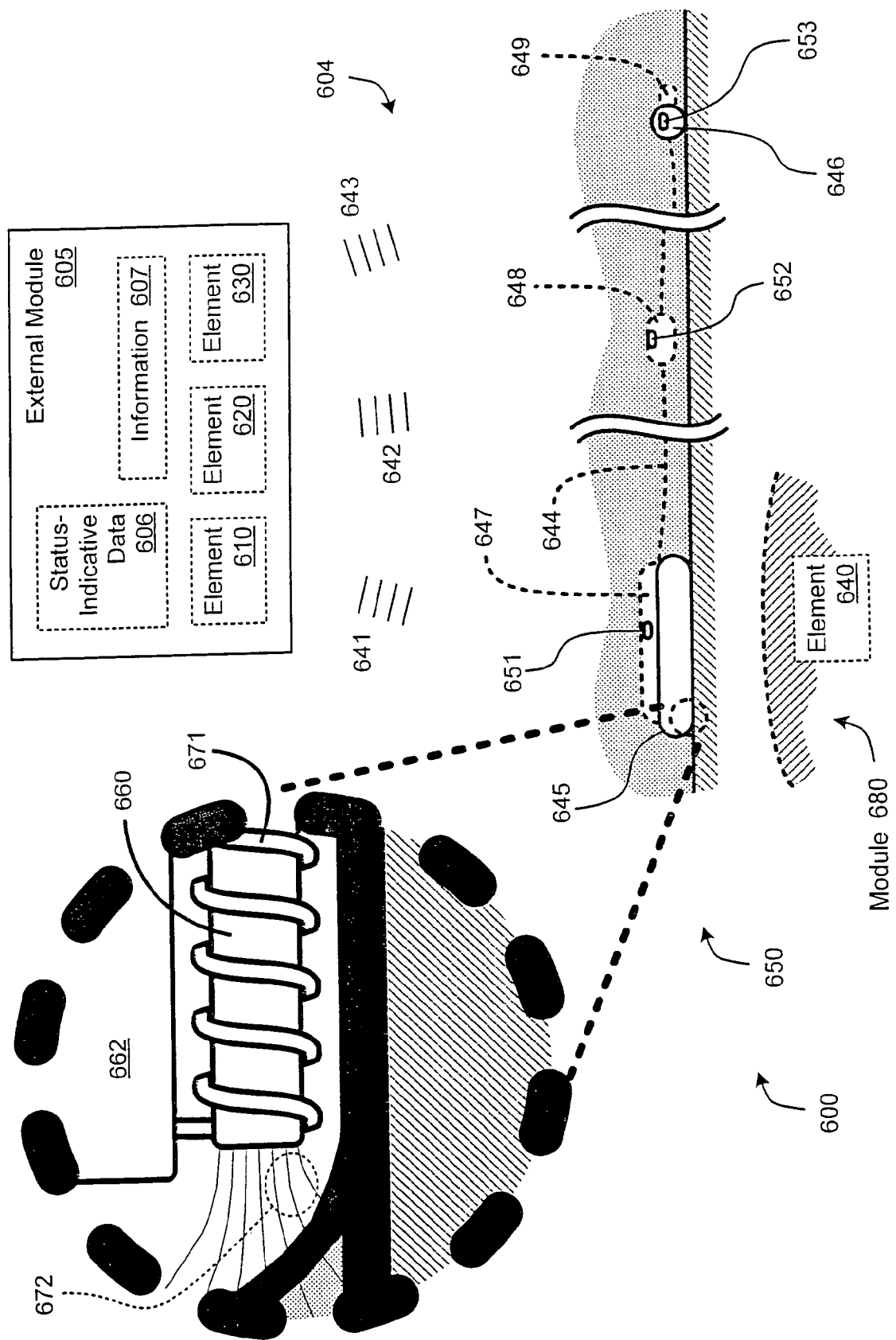

With reference now to FIG. 6, shown is a system 600 in which one or more technologies may be implemented. A tract portion 604 is shown with medical or veterinary utility modules 647, 648, 649, 650 (individually or collectively) small enough to pass through the tract safely per vias naturales. Such modules 647-650 may each include one or more wireless-control components 651, 652, 653. At least one such component has one or more engaging states and one or more disengaging states. The engaging state(s) cause(s) the medical or veterinary utility module to remain stationary, or at least to remain within tract portion 604 for a controllable and/or extended period, using one or more techniques as described herein. The disengaging state(s) allow(s) the medical or veterinary utility module to exit the tract per vias naturales.

In some variants one or more instances of external modules 605 (outside the tract) may be used for monitoring or guiding the behavior of one or more such utility modules 647-650. External module 605 may include one or more instances of optical communication elements 610, radio frequency communication elements 620, magnetic-field-generating elements 630, or magnetic materials or other such components that may be effective for interacting with the utility module(s) 647-650.

In some contexts, one or more optical communication elements 610 may be operable to transmit one or more wireless signals 641 comprising instructions and/or other information to component 651, for example, via a subject's mouth or other optically accessible site. Alternatively or additionally, component 651 may likewise be configured to transmit status-indicative data 606 or other such information 607 wirelessly to external module 605. In some contexts, one or more radio frequency communication elements 620 may likewise be operable to transmit one or more wireless signals 642 comprising instructions and/or other information to component 652, for example. Alternatively or additionally, component 651 may likewise be configured to transmit status-indicative data 606 or other such information 607 as wireless signals 642 to external module 605. In some contexts, one or more magnetic-field-generating or other elements 630 may likewise be operable to transmit one or more wireless signals 643 comprising instructions and/or other information to component 653, for example. Alternatively or additionally, component 653 may likewise be configured to transmit status-indicative data 606 or other such information 607 as wireless signals 643 to external module 605.

In some variants, (component or other) local modules 645, 646 may be adhesively, magnetically, buoyantly, spatially, or otherwise operable to remain in tract portion 604 for a month, a year, or longer. Such local modules may provide a convenient site for supporting one or more utility modules 647-650 directly and/or by an interstitial structure such as one or more tethers 644. Such support may be appropriate, in some contexts, for a day, a week, or more, as described herein.

One or more utility modules 647-650, for example, may be magnetically or otherwise supported by one or more mooring component modules 651 having a length more than four times greater than its median width. Such a magnetic configuration may, for example, include one or more ferromagnetic elements 660 operable for magnetic coupling with a high power electromagnet or other external flux-guiding structure adjacent tract portion 604, a ferromagnet worn on a belt, an implanted implanted material surrounding the pylorus, or some other nearby structure outside the tract. Removing such a belt may, for example, permit a user to cause ferromagnetic element 660 to be released per vias naturales, for example. Alternatively or additionally, local module 645 and/or one or more utility modules 647-650 may be released by current source 662 generating a current in one or more conductive coils 671 at least partly in opposition to the magnetic field generated by the ferromagnetic element(s) 660. A similar effect can be achieved by various flux-manipulation techniques, in lieu of or in addition to such current, such by moving oppositely-oriented ferromagnets (down as shown) into proximity with the depicted wall of tract portion 604. Alternatively or additionally, inflation or other modes of actuation may be used to achieve a disengagement of the utility module(s) 647-650. For examples of releasable tethering implementations, for example, see FIGS. 10-11 & 13-18 and their descriptions below.

Some variants of system 600 may be characterized as a medical or veterinary system comprising one or more sensor-containing modules, one or more local modules 645, 646 operable to remain within portion 604 for more than a day; and one or more tethers 644 configured to establish an effective range of motion of the one or more sensor-containing modules relative to the mooring module(s) within the tract comprising portion 604. This can occur, for example, in a context in which the contained sensor(s) implement one or more features described below with reference to FIG. 23 and in which the sensor-containing module(s) are implemented as one or more instances of utility modules 648 small enough to pass (safely) through a tract. Alternatively or additionally, one or more local modules 645 may likewise include one or more physical measurement components used by or with such sensors.

Figure 7:
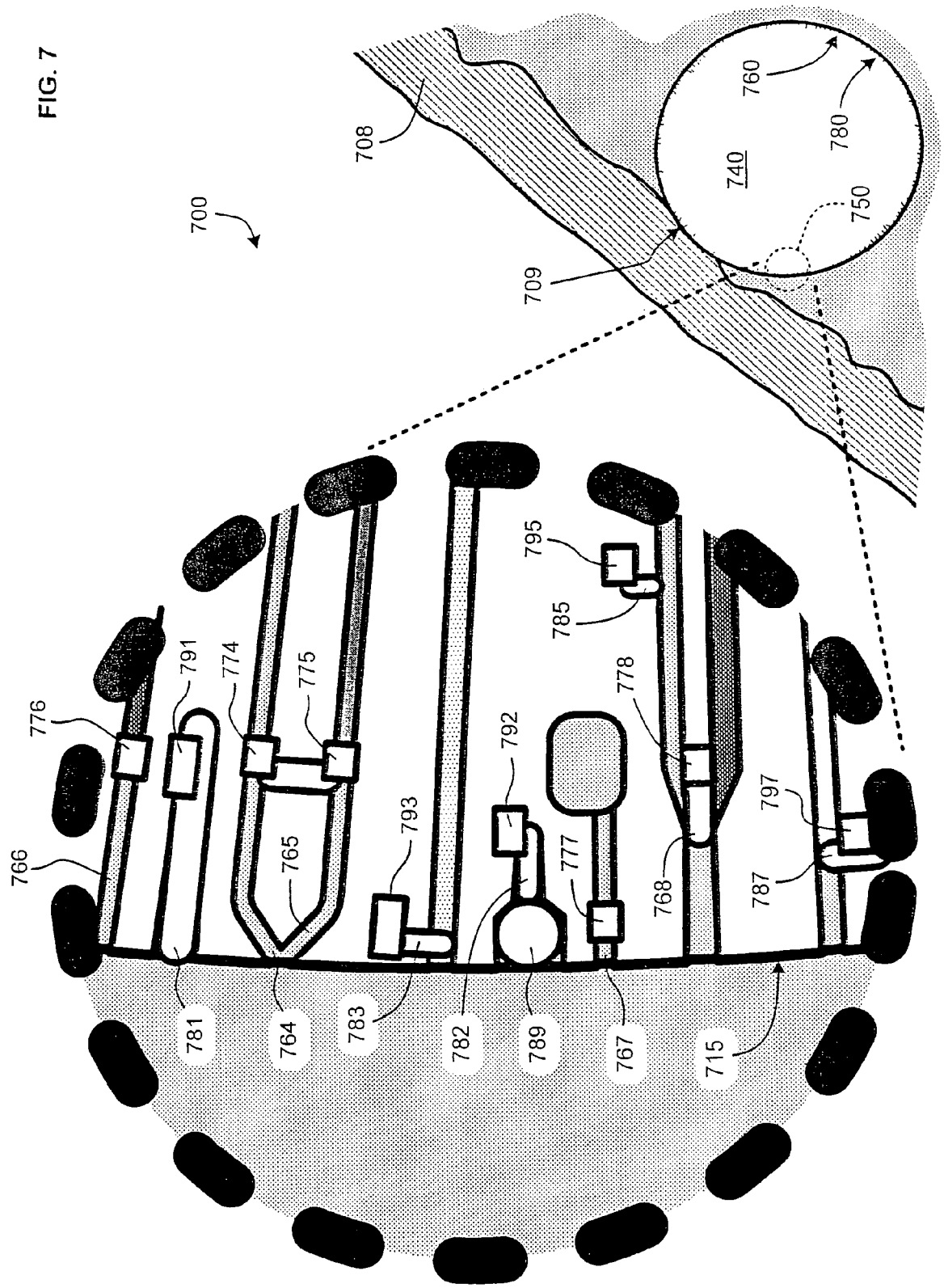

With reference now to FIG. 7, shown is another system 700 operable for retaining one or more medical or veterinary utility modules in a tract for an extended and/or controlled period. System 700 may comprise one or more instances of a mooring and/or utility module 740 having a protruding surface 715 immersed so that a portion 709 thereof is adjacent an irregular mucous membrane 708 of a tract. System 700 may (optionally) comprise one or more control components 750 such as one or more instances of adhesive-containing dispensers 764 and control circuitry 774 therefor, adhesive-solvent-containing dispenser 765 and control circuitry 775 therefor, anticoagulant-agent-containing dispenser 766 and control circuitry 776 therefor, antibiotic-containing dispenser 767 and control circuitry 777 therefor, or hybrid dispenser 768 and control circuitry 778 therefor. Alternatively or additionally, the control component(s) 750 may likewise comprise one or more instances of disengagement-inducing actuator 781 and control circuitry 791 therefor, releasable dispenser 789, dispenser-releasing actuator 782 and control circuitry 792 therefor, reservoir-opening actuator 783 and control circuitry 793 therefor, dosage-adjustment actuator 785 and control circuitry 795 therefor, or hybrid actuator 787 and control circuitry 797 therefor. Alternatively or additionally, the control component(s) 750 may be similarly configured to control one or more selected dispensers 760 or other actuators 780. Alternatively or additionally, the control component(s) 750 may likewise be configured to perform one or more other functions wirelessly, such as those described with reference to utility module 650 of FIG. 6 or elsewhere herein. Hybrid dispenser 768 and dosage-adjustment actuator 785 may likewise be configured for access to any of the materials or reservoirs described with reference to FIG. 21 herein, for example. In some variants, moreover, external module 605 may be operative for updating such control circuitry 791-795 wirelessly or otherwise as described herein, optionally commencing or altering one or more criteria for module 740 the tract per vias naturales.

In light of these teachings, numerous existing techniques may be applied for using biologically compatible binding agents as described herein without undue experimentation. See, e.g., U.S. Pat. No. 7,265,098 ("Polyacid/polyalkylene oxide gels and methods for their delivery"); U.S. Pat. No. 7,255,874 ("Biocompatible polymers and adhesives: compositions, methods of making and uses related thereto"); U.S. Pat. No. 7,097,851 ("Oral formulation for gastrointestinal drug delivery"); U.S. Pat. No. 7,056,550 ("Medical devices, drug coatings and methods for maintaining the drug coatings thereon"); U.S. Pat. No. 6,800,296 ("Modification of surfaces using biological recognition events"); U.S. Pat. No. 6,764,696 ("Effervescent drug delivery system for oral administration"); U.S. Pat. No. 6,689,380 ("Remote and local controlled delivery of pharmaceutical compounds using electromagnetic energy"); U.S. Pat. No. 6,582,720 ("Medicinal compositions adhering to stomach/duodenum"); U.S. Pat. No. 6,576,712 ("Preparation of hydrophilic pressure sensitive adhesives having optimized adhesive properties"); U.S. Pat. No. 6,428,813 ("Gastrointestinal mucosa-adherent pharmaceutical composition"). Those skilled in the art will also recognize how to apply numerous existing techniques for taking provisional, alternate, overlapping, or completion actions relating to such applications as exemplified herein without undue experimentation, in light of these teachings. Binding agents may likewise be used for coupling modules as described herein, before or during deployment.

Figure 8:
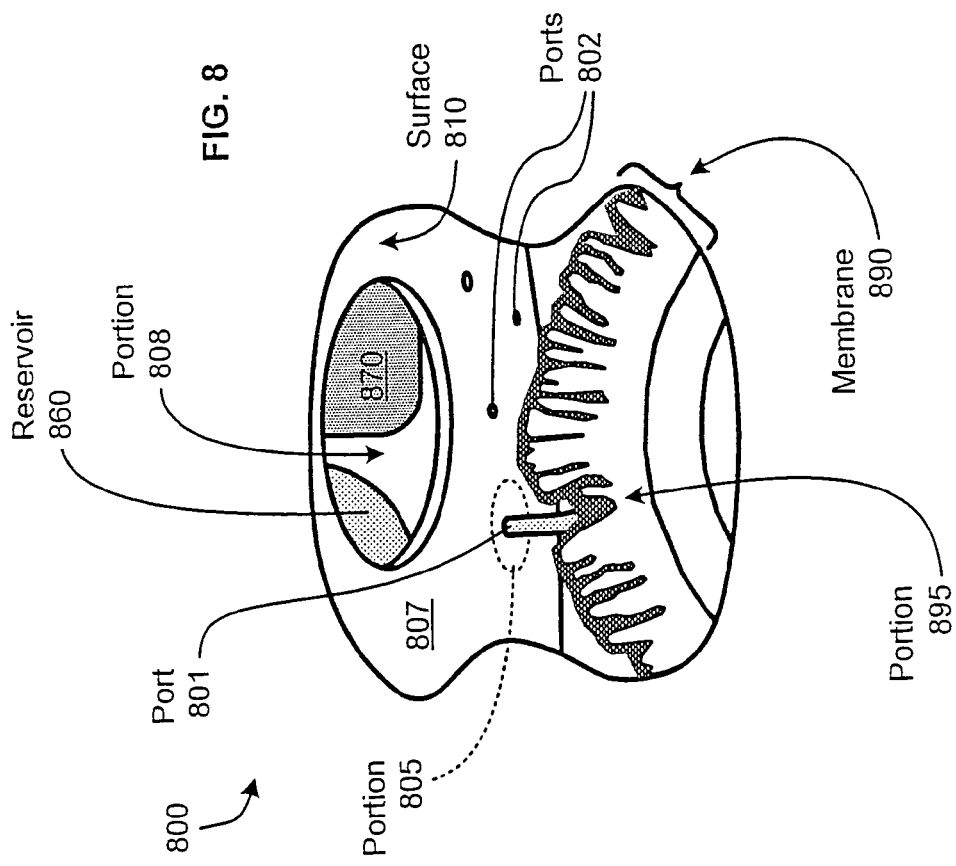

With reference now to FIG. 8, shown is another context in which one or more technologies may be implemented. A medical or veterinary system 800 shown there comprises at least one module body 807 small enough for a person or other subject to swallow. System 800 further comprises one or more (earlier-acting) ports 801 operable for dispensing adhesive-containing material from reservoir 860 and/or otherwise coupling at least portion 805 of module body 807 to a portion 895 mucous membrane 890. (As shown, surface 810 includes a portion 808 cut away to reveal a plurality of adhesive-containing reservoirs 860, 870.)

Some time later—such as an hour or a day, in some contexts—one or more other (ports 802 or other) attachment features may be invoked for coupling at least the module body 807 to another part of the mucous membrane 890. In a context in which bond 905 is formed within a minute at portion 805, for example, another application of adhesive may be dispensed (from reservoir 870 via ports 802, for example), bonding another portion 906 of module body 807 to another portion 996 of the mucous membrane 890. In some variants, for example, such sequential attachment operations may permit improved coupling with mucous 981 and/or mucosa 982.

Various modes of sequential attachment may be practiced, for example, in the context of FIG. 7. In a context in which module 740 is small enough to swallow, for example, it may initially attach to a mucous membrane 708 of an esophagus, gastric compartment, or intestine as shown. This can be accomplished by hooks or ligation components, for example, or by an activation of one or more adhesive-containing dispensers 764 (at least adjacent mucous membrane 708) by corresponding control circuitry 774. In some variants, for example, control circuitry 791 responsive to one or more sensors (optionally a piezoelectric transducer or other proximity- or contact-sense-enabled component, for example) may trigger one or more adjacent or successive dispensers to dispense an adhesive, for example.

Some time later, perhaps on the order of 10 minutes or 10 hours, one or more "next" adhesive or other attachment features are likewise invoked to attach (a) at a deeper level of mucous membrane 708 and/or (b) to a next vertical or lateral portion of mucous membrane 708. In the latter case, for example, module 740 may advance very slowly along mucous membrane 708, such as by rolling. In response to detecting a (wireless or other) disengagement-indicative condition, in some embodiments, module 740 may be configured to respond by ceasing such attachment operations, by invoking control circuitry 775 to activate adhesive-solvent-containing dispenser 765, by invoking control circuitry 791 to activate disengagement-inducing actuator 781 to push mucous membrane 708 away from module 740, or otherwise by facilitating detachment. Alternatively or additionally, such modes may include separating tether portions, adjusting buoyancy, activating a pressurized or other mode of propulsion, exerting tension along a moored tether, or other actions as described herein.

Figure 10:
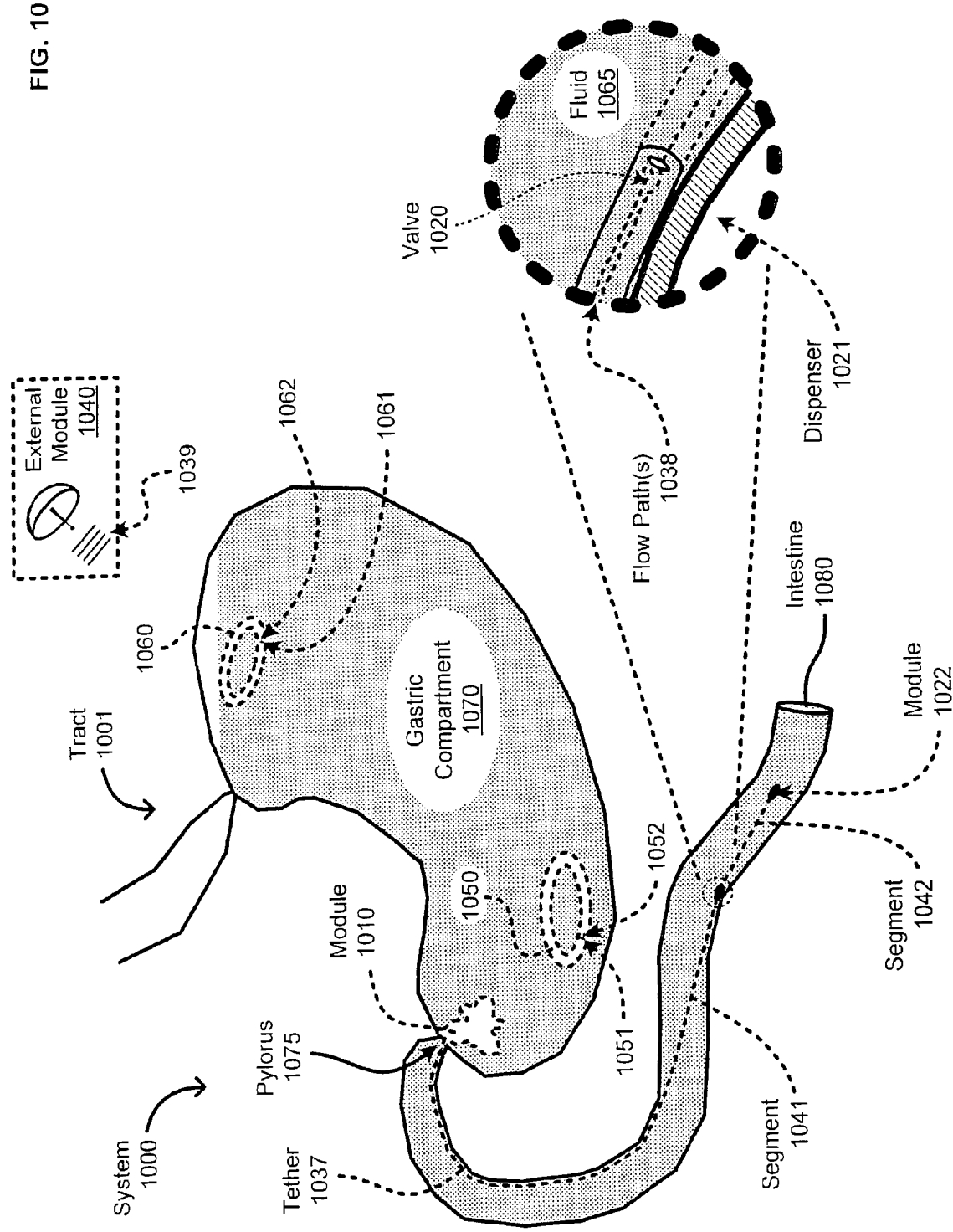

With reference now to FIG. 10, shown is a vicinity of a gastric compartment 1070 in a tract 1001 of a subject (human or otherwise) that may serve as a context for introducing one or more processes and/or devices described herein. As shown system 1000 may (optionally) include one or more instances of module 1010 each having one or more tethers 1037 or other portions extending through some of intestine 1080 and configured to anchor at pylorus 1075. System 1000 may likewise include one or more instances of modules 1050 dense enough to rest near the bottom of gastric compartment 1070 and/or modules 1060 buoyant enough to float within gastric compartment 1070, any or all of which may be configured with one or more dispensers 1051, 1061 and/or control modules 1052, 1062. Many suitable structures are described herein and in U.S. patent application Ser. No. 11/975,371, titled "Disintegrating Tract Interaction System," filed 17 Oct. 2007], also by Boyden et al., incorporated by reference to the extent not inconsistent herewith. In some such embodiments, each tether 1037 of interest may comprise one or more segments 1041 directly or indirectly coupling a reservoir-containing module (such as module 1010 or module 1050) with one or more of its dispensers 1021. In some variants, moreover, such modules 1010, 1050, 1060 may comprise control modules 1052, 1062 or other circuitry operable for handling one or more wireless signals 1039 passing to or from external module 1040. Alternatively or additionally, each tether 1037 of interest may comprise one or more segments 1042 directly or indirectly coupling a reservoir-containing module with one or more of its sense modules 1022. In various embodiments described herein, such dispensers, sensor modules, and support structures therefore may each be inside, outside, or spanning the gastric compartment or, in some cases, extending outside the tract. In some variants, one or more such segments 1041, 1042 configured to support such devices in intestine 1080 comprise structures of a (positive) solubility in a gastric compartment low enough to remain in situ for more than a day (or month or year), as described herein. Alternatively or additionally one or more such modules 1010, 1050, 1060 may include two or more (component) modules similarly tethered together as described herein.

In some embodiments, one or more such modules 1010, 1050, 1060 or other fluid-exposed structures depicted herein may comprise at least an external layer primarily made of one or more water insoluble polymers such as cellulose derivatives (i.e., ethylcellulose), polyvinyl acetate, neutral copolymers based on ethyl acrylate and methylmethacrylate, copolymers of acrylic and methacrylic acid esters with quaternary ammonium groups, or the like. In some embodiments, polymers used in forming such low-solubility elements may be plasticized. Examples of plasticizers that may be used for this purpose include, but are not limited to, triacetin, tributyl citrate, triethyl citrate, acetyl tri-n-butyl citrate diethyl phthalate, castor oil, dibutyl sebacate, acetylated monoglycerides, or the like and/or substantially any combination thereof. In some embodiments, one or more such plasticizers may be present at about 5 to 50 weight percent and more typically about 10 to 25 weight percent based on the polymer to which the plasticizer is added. The type of plasticizer and its content depends on the polymer or polymers and/or the nature of the coating system.

In some embodiments, water-soluble nonionic polysaccharide derivatives may be used to wrap one or more therapeutic agents or other soluble structures for rapid release. For example, hydroxypropylmethylcellulose, hydroxypropylcellulose, and/or sodium carboxymethylcellulose may be used. Such polymers form coatings that quickly dissolve in digestive fluids or water and have a high permeability. Accordingly, in some embodiments, such polymers may be used for rapid release responsive to ingestion.

In some embodiments, one or more therapeutic agents or other structures may be wrapped in a wrapper that provides for sustained release of the one or more therapeutic agents. For example, one or more therapeutic agents may be released continuously over twelve hours through use of wrappers constructed from ethyl cellulose and an ethyl acrylate-methyl methacrylate-ethyl trimethylammoniumchloride methacrylate copolymer as the release controlling wrapper. Existing methods and materials that may be used to prepare such wrappers are known by those skilled in the art and are commercially available (i.e., Rohm Pharma, Piscataway, N.J.; U.S. Pat. Nos. 6,656,507; 7,048,945; 7,056,951; hereby incorporated by reference to the extent not inconsistent herewith).

Some variants of system 1000 may be characterized as medical or veterinary systems comprising one or more material supplies in module 1010 operable for placement within a stomach (gastric compartment 1070) and operably coupled with one or more conduits in tether 1037 to guide material from the module 1010 out of the stomach. Many reservoir-containing structures described herein are well suited for such trans-gastric dispensations of therapeutic or other agents. In light of teachings herein, numerous existing techniques may be applied for preparing appropriate such drug delivery formulations, as described herein, without undue experimentation. See, e.g., U.S. Pat. No. 7,189,414 ("Controlled release oral drug delivery system"); U.S. Pat. No. 7,125,566 ("Particulate drug-containing products and method of manufacture"); U.S. Pat. No. 7,097,851 ("Oral formulation for gastrointestinal drug delivery"); U.S. Pat. No. 6,960,356 ("Orally administered drug delivery system providing temporal and spatial control"); U.S. Pat. No. 6,699,503 ("Hydrogel-forming sustained-release preparation"); U.S. Pat. No. 6,644,517 ("Stem configuration to reduce seal abrasion in metered dose aerosol valves"); U.S. Pat. No. 6,638,534 ("Preparation capable of releasing drug at target site in intestine"); U.S. Pat. No. 6,582,720 ("Medicinal compositions adhering to stomach/duodenum"); U.S. Pat. No. 6,475,521 ("Biphasic controlled release delivery system for high solubility pharmaceuticals and method"); U.S. Pat. No. 6,399,086 ("Pharmaceutical preparations for the controlled release of beta-lactam antibiotics"); U.S. Pat. No. 6,240,917 ("Aerosol holding chamber for a metered-dose inhaler"); U.S. Pat. No. 6,116,237 ("Methods of dry powder inhalation"); U.S. Pat. No. 6,060,069 ("Pulmonary delivery of pharmaceuticals"); U.S. Pat. No. 5,989,217 ("Medicine administering device for nasal cavities"); U.S. Pat. No. 5,906,587 ("Apparatus and method for the treatment of esophageal varices and mucosal neoplasms"); U.S. Pat. No. 5,837,261 ("Viral vaccines"); U.S. Pat. No. 5,823,180 ("Methods for treating pulmonary vasoconstriction and asthma"); U.S. Pat. No. 5,645,051 ("Unit dose dry powder inhaler"). Those skilled in the art will also recognize how to apply numerous existing techniques for taking provisional, alternate, overlapping, or completion actions relating to such applications as exemplified herein without undue experimentation, in light of these teachings. One or more wireless signals 1039 may be used directly to control some or all aspects of activating one or more such dispensers 1021, 1061 on a selective basis, for example. Sense module 1022 may be configured to signal one or more dispensers 1021, 1051 to reduce, postpone, or forego an output of a bioactive material, for example, in response to a high level of such materials (or metabolites or other indicators thereof) being detected. Alternatively or additionally, such functionality may be configured to depend on whether one or more modules 1010, 1050, 1060 are depleted, not yet deployed, disintegrated, or in some other condition that may prevent effective operation.

In some cases, such functionality may likewise depend upon one or more other determinants in substantially any desired combination: upon whether excessive acidity or some other symptom has been detected directly, upon whether an a priori attribute of a subject makes a bioactive material unnecessary and/or unsafe for a potential dispensation, upon whether the subject has contemporaneously requested or otherwise authorized a pain reliever, upon how long a time has elapsed since a prior dispensation, upon other state or timing factors as described herein, upon how much remains of a reservoir or other bioactive material supply, upon whether a subject has taken alcohol or any other controlled substance, or upon other determinants such as are known in the art. Such combinations may each be effectuated by comparative, arithmetic, conjunctive, or other operators relating each pairing of determinants described herein, for example.

In light of these teachings, numerous existing techniques may be applied for performing appropriate telemetry or otherwise handling wireless signals as described herein without undue experimentation. See, e.g., U.S. Pat. No. 7,262,020 ("Methods for comparing relative flux rates of two or more biological molecules in vivo through a single protocol"); U.S. Pat. No. 7,214,182 ("Wireless in-vivo information acquiring system, body-insertable device, and external device"); U.S. Pat. No. 7,160,258 ("Capsule and method for treating or diagnosing the intestinal tract"); U.S. Pat. No. 7,146,216 ("Implantable muscle stimulation device for treating gastrointestinal reflux disease"); U.S. Pat. No. 7,118,529 ("Method and apparatus for transmitting non-image information via an image sensor in an in vivo imaging system"); U.S. Pat. No. 6,929,636 ("Internal drug dispenser capsule medical device"); U.S. Pat. No. 6,632,655 ("Manipulation of microparticles in microfluidic systems"); U.S. Pat. No. 6,503,504 ("Delivery of bioactive compounds to an organism"); U.S. Pat. No. 6,411,842 ("Implant device for internal-external electromyographic recording, particularly for the in vivo study of electromotor activity of the digestive system"); U.S. Pat. No. 6,285,897 ("Remote physiological monitoring system"); U.S. Pat. No. 6,403,647 ("Pulsed administration of compositions for the treatment of blood disorders"); U.S. Pat. No. 6,360,123 ("Apparatus and method for determining a mechanical property of an organ or body cavity by impedance determination"); U.S. Pat. No. 6,329,153 ("Method for evaluating immunosuppressive regimens"); U.S. Pat. No. 5,985,129 ("Method for increasing the service life of an implantable sensor"); U.S. Pat. No. 5,779,631 ("Spectrophotometer for measuring the metabolic condition of a subject"); U.S. Pat. No. 5,569,186 ("Closed loop infusion pump system with removable glucose sensor"). Those skilled in the art will also recognize how to apply numerous existing techniques for taking provisional, alternate, overlapping, or completion actions relating to such applications as exemplified herein without undue experimentation, in light of these teachings. Sense module 1022 may be configured to transmit one or more selection indications wirelessly, for example, or to communicate such information via a signal conduit to module 1010, which subsequently transmits an audible or other wireless signal. In some variants, for example, module 1010 includes a signal bearing conduit to a speaker in a subject's jaw or ear to notify the subject of a dispensation.

An enlarged view is shown of a portion of tether 1037 comprising a segment 1041 having one or more flow path(s) 1038 for a fluid material to be released into digestive fluid 1065 through dispenser 1021 (when valve 1020 is open). Valve 1020 may actuate as a mechanical response to the fluid material exceeding a threshold pressure and/or as an electro-mechanical or other response to other information passing through the flow path(s) 1038. Tether 1037 may likewise include segment 1042 to other dispensers and/or sense modules, optionally coupled via extensions of one or more of the flow paths 1038 as shown. Segment 1042 may optionally comprise optical fiber, for example, providing mechanical support for and an image data flow path from one or more lenses or other sensors.

Figure 11:
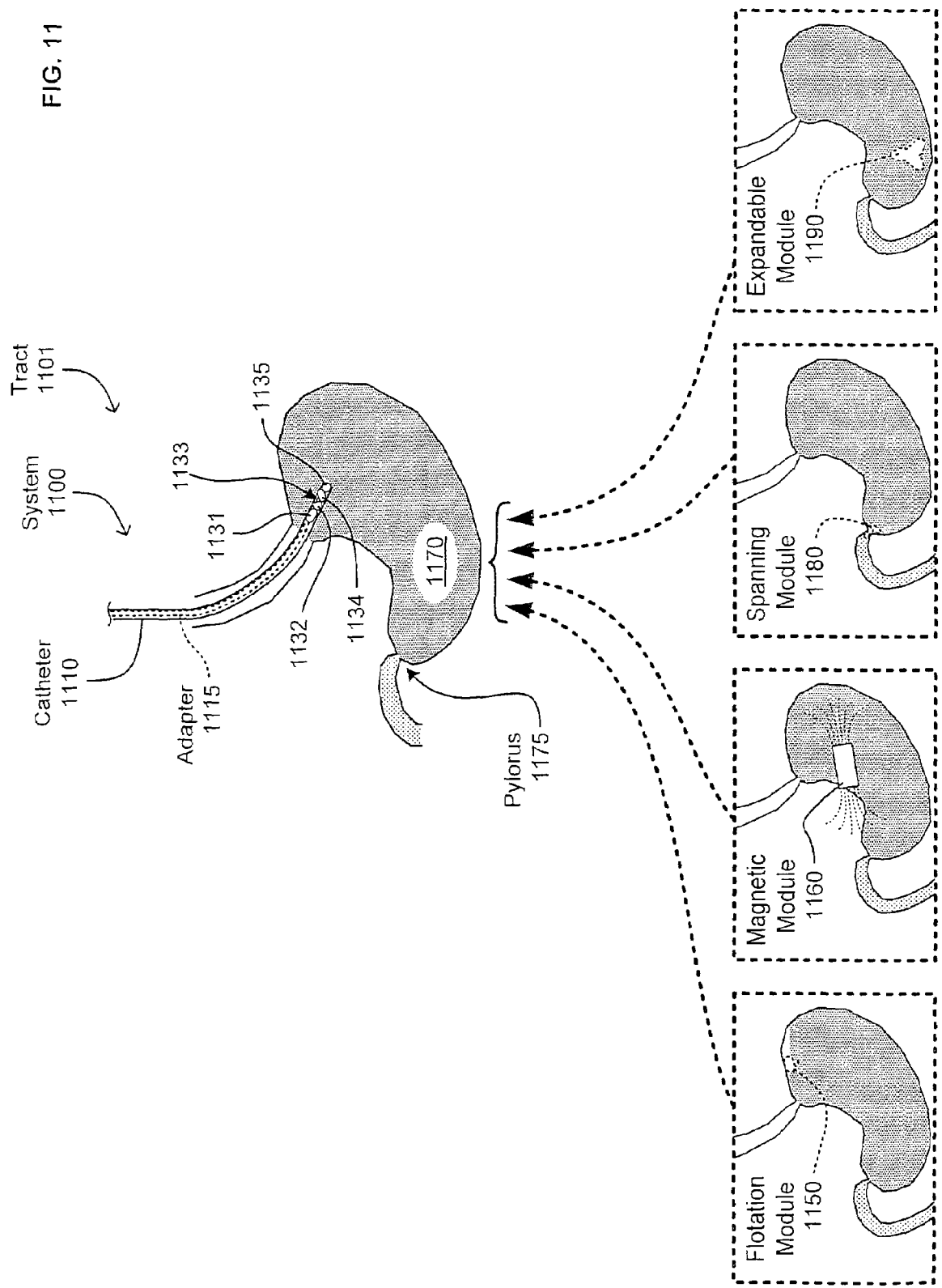

With reference now to FIG. 11, shown is an example of a system that may serve as a context for introducing one or more processes and/or devices described herein. As shown system 1100 may (optionally) include a catheter 1110 containing several modules 1131, 1132, 1134, 1135 each within gastric compartment 1170 and small enough to pass through tract 1101 individually. In some variants, catheter 1110 may be small enough to pass through a nasal passage, for example. Alternatively or additionally, catheter 1110 may comprise one or more inner sleeves or other adapters 1115 configured for use in manipulating one or more modules in situ, such as by urging module 1131 outward, by applying an adhesive, by cutting a tether, or for other operations as described herein in various implementations. As shown, most or all of such modules 1131, 1132, 1134, 1135 are strung onto a common tether 1133, preferably in a configuration that is dosed, sequenced, or otherwise tailored for administration to a specific patient, and optionally within a soluble capsule. In some variants, the tether is strung through a non-axial portion of one or more intermediate modules 1132, 1134 so that tension in the tether tends to urge the grouping of modules to become less coaxial. Such tension can be preloaded in an elastic length of tether 1133, for example, so that a shape change occurs immediately in response to an expulsion from catheter 1110 or a capsule, or later in response to detectable environmental changes. Such shape changes may be configured to occur in response a sufficiently-long exposure to an acidic and/or aqueous environment, a body-temperature environment, an electrically conductive environment, or other such environmental circumstances indicative of entry into a specific portion of a tract of a given subject. Such shape changes in gastric compartment 1170 may cause a grouping of several modules 1131, 1132, 1134, 1135 to become too large to pass through pylorus 1175 and too irregular for them to become a problematic blockage. For example, some or all of the modules 1131, 1132, 1134, 1135 may be configured to swell or otherwise remove slack from and/or introduce tension into tether 1133. If tether 1133 is configured in a loop, for example, such swelling will tend to cause the modules to become less collinear, and thus less likely for pylorus 1175 to be blocked.

In most contexts, a single module is "small enough to pass through a tract" if a physician, veterinarian, or other skilled care provider would consider it safe for an inert item of that size to pass through the tract without becoming an obstruction. For most human beings and other mammals this corresponds with a module that is narrower than an eyeball (e.g., at most about 2 centimeters wide) and at most a few times as long as the eyeball (e.g., up to several centimeters long), and a slightly larger size for highly pliable modules. An unobstructed, normal tract in a human adult of typical size, for example, may reasonably be expected to pass an inert module as large as a penny or AAA battery but not one as large as a typical pen or golf ball.

In most contexts, a module may be described as "at least 10% as large" as an item if the module is at least 10% as long as the item. The module is likewise "at least 10% as large" as the item if the module is at least 10% as voluminous as the item, taking the volume of each to include the volume of any bores or other regions of concavity therein. In an embodiment in which module 1132 is "at least 10% as large" as module 1131, for example, either of these module may accordingly be larger than the other in terms of length or volume.

In most contexts, a tether is "operable for coupling" modules via a gap if the tether helps to maintain the modules in a vicinity of each other by extending at least partly into the gap. One or more such tethers may wrap around several such modules, for example, securing them at least partly within one or more recesses of a ring, spool, or cup.

In some variants, system 1100 is initially configured so that catheter 1110 contains several modules 1131, 1132, 1134, 1135 each small enough to pass (safely) through tract 1101. As shown, "second" module 1135 may be sized within an order of magnitude of "first" module 1131, at least in terms of length, and/or with "second" module 1135 somewhat shorter than "first" module 1131. Alternatively or additionally, "third" module 1134 may (optionally) be at least half as voluminous as "first" and/or "second" modules 1131, 1135. One or more instances of intermediate modules 1132, 1134 may (optionally) each comprise a unitary body having an overall average density smaller than 0.9 grams per milliliter, such modules tending to remain in gastric compartment 1170 for a time even after tether 1133 no longer operates.

Various modes of surgery-optional and/or catheter-optional deployment are described herein for maintaining mooring and/or utility modules in a gastric compartment for a controllable and/or extended periods—4 hours, a day, a week, a month, or more—in various contexts. Such prolonged durations may be achieved, for example, by including one or more flotation modules 1150, one or more magnetic modules 1160, one or more (pylorus-)spanning modules 1180, one or more expandable modules 1190, suitable adhesion or piercing features, or other modes as described herein. For example, various configurations of magnetic-flux-generating or other magnetic-flux-guiding modules may be implanted or otherwise positioned adjacent pylorus 1175, on a removable belt worn by a subject, or otherwise in a vicinity of tract 1101.

Figure 12:
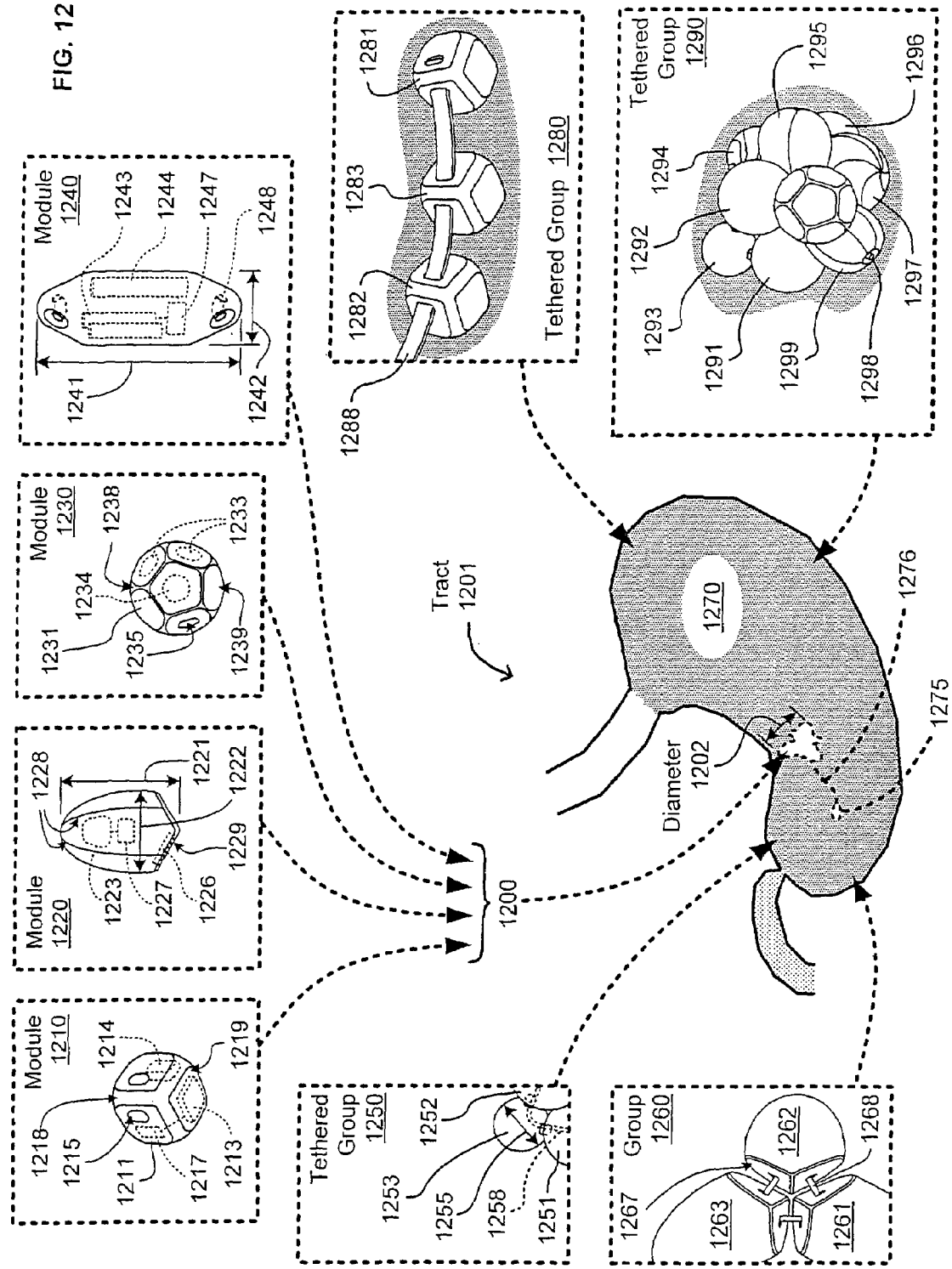

With reference now to FIG. 12, shown is an example of a system that may serve as a context for introducing one or more processes and/or devices described herein. As shown tract 1201 may include gastric compartment 1270 containing one or more systems 1200 such as tethered groups 1250, 1260, 1280, 1290. Each such system 1200 may include one or more instances of modules 1210, 1220, 1230, 1240 as shown, for example, in a sufficient number so that system 1200 has an effective cross-sectional diameter 1202 too large to permit exit from gastric compartment 1270 in any orientation. Some embodiments of system 1200 may further comprise one or more additional modules 1275 coupled with such a group by surgical thread or a similarly flexible tether 1276 about 1 centimeter or more in length.

System 1200 may include one or more modules 1210 each comprising a cube-like unitary body 1211 with six primary external surfaces 1219 all bounded by a substantially convex external surface 1218. Module 1210 may further include one or more instances of bores 1215 or other gaps configured to facilitate passage or other guidance of one or more tethers as described herein. Module 1210 may also include one or more instances of (incremental) dispensers 1213, 1214, fluidic access to at least some of which may be controlled by circuitry 1217 as described herein.

Alternatively or additionally, system 1200 may (optionally) include one or more modules 1220, an instance of which is shown at a somewhat magnified scale similar to that of module 1210. Module 1220 may comprise an oblong unitary body having a length 1221 of about 1 millimeter or larger, and at least 10% greater than its cross-sectional diameter 1222. The body is bounded by an upper surface having (at least somewhat) longitudinal ribs 1228 as well as a plurality of other faces 1229. At least one such face 1229 may be situated adjacent one or more flux-guiding elements 1226 operable for responding to a magnetic field within a portion of the tract. Such an instance may thus tend to align (or resist misalignment) with one or more other modules of system 1200, for example, if either is implemented as a permanent magnet or electromagnet. This can be particularly useful for controlling a mode of expansion in embodiments like that of group 1260 in which opposite ends of the tether are situated in different modules, for example. While in the tract, moreover, such flux-guiding elements may be safely and reliably drawn to a tract wall, for example, by providing a strong magnetic field from outside the tract. Module 1220 may likewise include one or more instances of dispensers 1223, fluidic access to at least some of which may be controlled by circuitry 1227 as described herein.

Alternatively or additionally, system 1200 may (optionally) include one or more modules 1230, an instance of which is shown at a somewhat magnified scale similar to those of other modules 1210, 1220 described above. Module 1230 as shown has a unitary, substantially polyhedral body 1231 with one or more convex external surfaces 1238 and several other surfaces 1239. (In some embodiments, such other surfaces 1239 may each comprise saddle regions, recesses, or otherwise structured surfaces as described herein.) Module 1230 may include one or more instances of passive dispensers 1233 each containing 1-15 grams of medicinal material configured to dissolve somewhat uniformly in gastric compartment 1270 over one or more days, weeks, or months. Module 1230 may likewise include one or more instances of dispensers 1233, 1234 and/or rotationally asymmetric gaps 1235 for accommodating various tether configurations as described herein.

Alternatively or additionally, system 1200 may (optionally) include one or more modules 1240, an instance of which is shown at a somewhat magnified scale similar to those of other modules 1210, 1220, 1230 described above. Module 1240 may (optionally) comprise a unitary body having an overall average density smaller than 0.9 grams per milliliter and/or a cross-sectional diameter 1242 larger than one millimeter. Alternatively or additionally, module 1240 may include one or more passages 1248 or other gaps collectively sufficient for receiving more than one tether or tether winding. Module 1240 may likewise include one or more instances of dispensers 1243, 1244, fluidic access to at least some of which may be controlled by circuitry 1247 as described herein.

In some embodiments, system 1200 may be configured so that the "first" module comprises module 1210, so that the "second" module comprises module 1220, and so that the "third" module comprises module 1230, all coupled by a single common tether. In some such embodiments, the relative scaling of modules 1210, 1220, 1230 is such that "second" module 1220 (i.e. at length 1221) is at least half as long and/or voluminous as "first" module 1210. Alternatively or additionally, "third" module 1230 may (optionally) be made larger so that it is more voluminous than "first" module 1210 and/or "second" module 1220. In some variants, moreover, system 1200 may further comprise one or more instances of module 1240 as shown, a "fourth" module having a length 1241 more than twice the width thereof. Alternatively or additionally, tract 1201 may (optionally) contain tethered group 1250 comprising several modules 1251, 1252, 1253 bound together by a single common tether 1258. Tethered group 1250 may likewise include other modules, some or all of which may optionally be bound by other tethers (not shown) to create a desired configuration. In some embodiments, module 1253 may have a cross-sectional diameter 1255 larger than one millimeter, optionally 2-5 millimeters or larger.

Alternatively or additionally, tract 1201 may (optionally) contain group 1260 comprising several modules 1261, 1262, 1263 bound together by a single, primarily elastic tether 1268. (Group 1260 is shown in tension to expose a plurality of substantially flat faces 1267 on each module.) In some embodiments, group 1260 is configured so that the "first" module comprises module 1261 and so that the "third" module comprises module 1263, and so that one or both of these implement module 1220. Module 1261 may (optionally) comprise one or more instances of dispenser 1223 containing a total of 1-15 grams of medicinal material, for example, such as an antibiotic or statin. Moreover in some variants "third" module 1263 may be more than half as voluminous as, or may be more voluminous than, "first" module 1261 and/or "second" module 1262. Alternatively or additionally, "third" module 1263 may be at least half as long as, or may be longer than, "first" module 1261 and/or "second" module 1262.

Alternatively or additionally, tract 1201 may (optionally) contain tethered group 1280 comprising several modules 1281, 1282, 1283 (each small enough to pass through tract 1201 individually but prevented from such passage by virtue of being) bound together by a single common tether 1288. Any or all of modules 1281, 1282, 1283 may be configured as instances of module 1210, each optionally implementing circuitry 1217, dispenser 1213, or other attributes of module 1210 as described herein. As shown, modules 1281-1283 may be supported along at least a rotationally asymmetric portion of tether 1288. Alternatively or additionally, the "third" module 1283 may be at least half as voluminous as the "second" module 1282.

Alternatively or additionally, tract 1201 may (optionally) contain tethered group 1290 comprising several modules 1291, 1292, 1293, 1294, 1295, 1296, 1297, 1299, at least some of which are small enough to pass through tract 1201 individually but prevented from such passage by virtue of being bound together in tethered group 1290. Any or all of modules 1291-1297 and 1299 may be configured as instances of other modules described herein. Tether 1298 binds together at least a "first" module 1299 and some of the other modules 1291-1297. Alternatively or additionally, as shown, "first" and/or "second" ones of modules 1294-1297 may each be more than twice as long as each respective width thereof.

Figure 13:
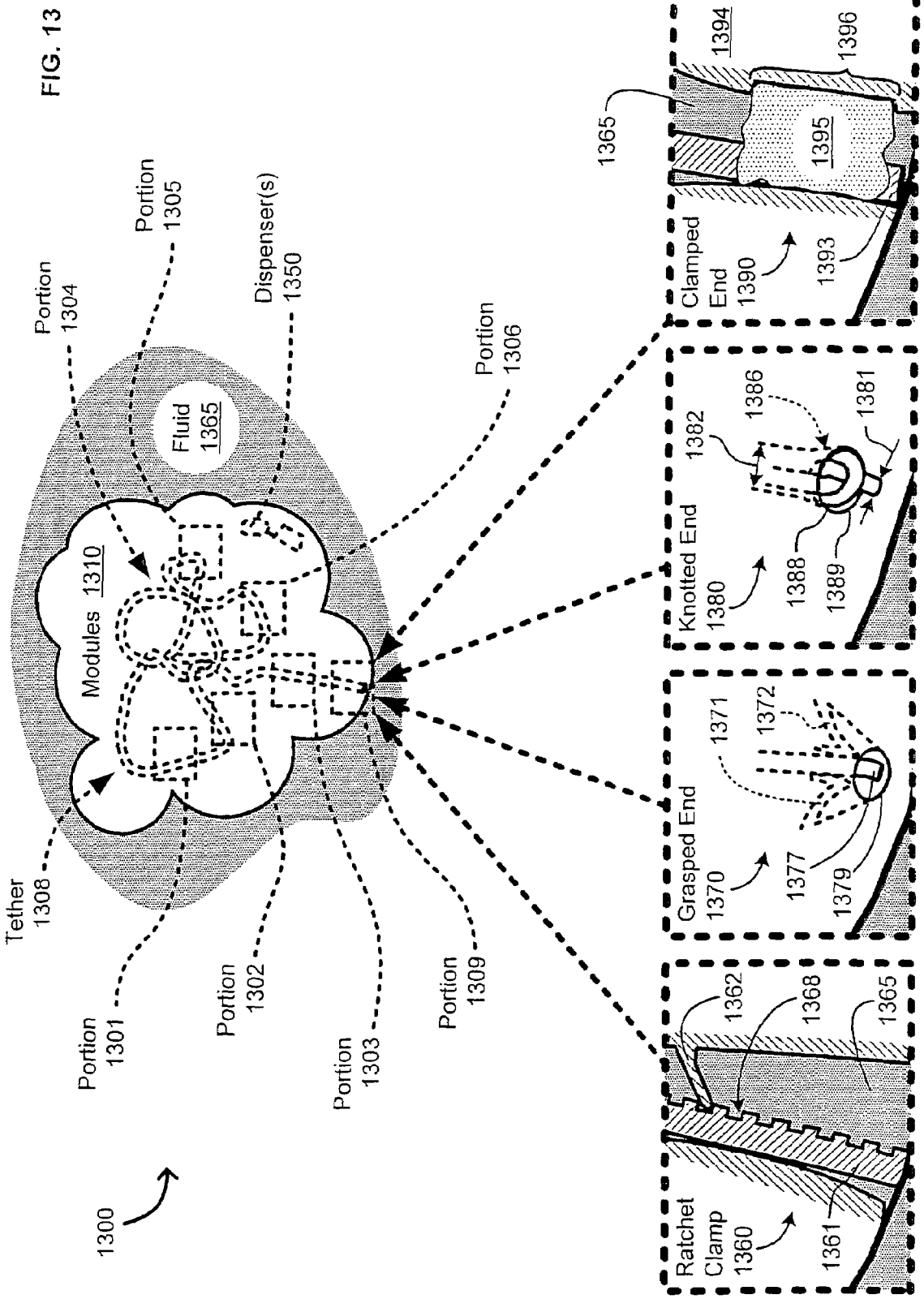

With reference now to FIG. 13, shown is an example of a system that may serve as a context for introducing one or more processes and/or devices described herein. As shown system 1300 may include at least one tether 1308 binding several non-aligned modules 1310 within fluid 1365. Tether 1308 may comprise one or more distal portions 1309 bounding a "middle" portion 1304 containing or otherwise overlapping one or more other portions 1301, 1302, 1303, 1305, 1306. Each of modules 1310 is roughly of similar size and small enough to pass through an entire tract containing fluid 1365 (at least after an appropriate deflation). Tether 1308 effectively couples a "first" and "second" ones of modules 1310 via a gap in (at least) a "third" module, tether 1308 having at least a middle portion 1304 configured to slip free from the "third" module responsive to the tether breaking or being released.

In some embodiments, any "first" or "second" module as described herein may comprise a ratchet clamp 1360 comprising one or more flexible members 1362 extending into one or more corresponding recesses 1368 of tether 1361 so that tether 1361 can be pulled outward (downward as shown) from the module but resists retraction. In some variants of system 1100 (of FIG. 11), for example, such a mechanism can be used by adapter 1115 to remove slack from (and optionally place static tension into) at least a middle portion of tether 1133. Excess length of tether 1133 can then be pulled free (if notched or perforated, for example) or cut off (with a cutting device of adapter 1115, for example, not shown).

Alternatively or additionally, any "first" or "second" module as described herein may comprise a grasped (tether) end 1370 comprising one or more flexible members 1371, 1372 gripping a rotationally symmetric portion of an end of tether 1377 at an orifice 1379 (such as may implement distal portion 1309 of tether 1308). In some variants, such flexible members 1371 may be calibrated so that they will release tether 1377 in response to a predetermined tensile force (upward as shown) urging tether 1377 to be released by the module. In some variants, a tether 1377 includes a smooth distal portion 1309, facilitating the release of such modules from the "second" module, for example.

Alternatively or additionally, any "second" or "third" module as described herein may comprise a knotted (tether) end 1380 in which a stopper or other suitable knot 1388 is used in conjunction with a bore 1389 having a cross-sectional diameter 1382 larger than a cross-sectional diameter 1381 of the tether but smaller than that of the knot 1388. The bore may (optionally) have a tapered portion 1386 so that part of the bore is large enough to accommodate a portion of the knot.

Alternatively or additionally, any module as described herein may comprise a clamped end 1390 in which an adhesive and/or expansive element 1395 expands or otherwise emerges when exposed to fluid 1365 (from one or more recessed portions 1396 of module 1394, for example) to secure a distal portion of a tether 1393. Such clamping may result from adhesive activation and/or from a compression fit, for example, resulting from element 1395 reacting to water in fluid 1365.

In some embodiments, system 1300 comprises several ("first," "second," and "other") modules 1310 bound by tether 1308, optionally for deployment via a flexible catheter or soft gelatin capsule into an animal needing treatments over an extended period (of several days or months, for example). Any or all such modules 1310 may each comprise one or more instances of circuitry for controlling one or more dispensers 1350 and/or a unitary body having an overall average density smaller than 0.9 grams per milliliter. In some embodiments, for example, enough buoyant modules may be included so that the overall average density of system 1300 is smaller than that of fluid 1365.

In some embodiments, a therapeutic agent may be placed into one or more dispensers 1350 described herein, optionally packaged with one or more solid or gel phase carriers or excipients. Examples of such carriers or excipients include, but are not limited to, croscarmellose sodium, povidone, microcrystalline cellulose, calcium carbonate, calcium phosphate, various sugars, starches, cellulose derivatives, pregelatinized starch, polymers such as polyethylene glycols, lactose, lactose monohydrate, sucrose, talc, gelatin, agar, pectin, acacia, magnesium stearate, stearic acid and substantially any combination thereof.

In some embodiments, therapeutic agents that are hydrophobic may be packaged through use of a cosolvent system comprising benzyl alcohol, a nonpolar surfactant, a water-miscible organic polymer, and an aqueous phase. The cosolvent system may be the VPD co-solvent system. VPD is a solution of 5 percent weight/volume benzyl alcohol, 8 percent weight/volume of the nonpolar surfactant polysorbate 80, and 65 percent weight/volumen polyethylene glycol 500, made up to volume in absolute ethanol. The VPD co-solvent system (VPD:5W) consists of VPD diluted 1:1 with a 7 percent dextrose in water solution. This co-solvent system dissolves hydrophobic therapeutic agents well, and itself produces low toxicity upon systemic administration. The proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol (i.e., polyvinyl pyrrolidone; and other sugars or polysaccharides may substitute for dextrose). Many other delivery systems may be used to administer hydrophobic therapeutic agents as well. For example, liposomes and emulsions are well known examples of delivery vehicles or carriers for hydrophobic drugs. Certain organic solvents such as dimethysulfoxide also may be employed, although usually at the cost of greater toxicity.

Some therapeutic agents may be packaged as salts with pharmaceutically compatible counter ions. Pharmaceutically compatible salts may be formed with many acids, including hydrochloric, sulfuric, acetic, lactic, tartaric, malic, succinic, etc. Salts of therapeutic agents tend to be more soluble in aqueous or other protonic solvents than are the corresponding free-base forms.

Numerous carriers and excipients are known and are commercially available (i.e., The Merck Index, 13th Edition, An Encyclopedia of Chemicals, Drugs, and Biologicals, Merck & Co. Inc., Whitehouse Station, N.J. 2001; Mosby's Drug Guide, Mosby, Inc., St. Louis, Mo. 2004; Remington: The Science and Practice of Pharmacy, 20th Edition, Lippincott Williams & Wilkins, Philadelphia, Pa. 2000; Physicians' Desk Reference, Thompson, PDR, Montvale, N.J. 2004; U.S. Pat. Nos. 6,773,721; 7,053,107; 7,049,312 and Published U.S. Patent Application No. 20040224916; herein incorporated by reference to the extent not inconsistent herewith). In some embodiments, such methods may be used with regard to one or more dietary or other regimen compliance objectives and/or combinations of one or more pharmaceutical or nutraceutical agents with one or more aspects of diet, or other subject attributes.

One or more instances of tethers 1308 among modules 1310 may (optionally) include one or more elastic (length) portions 1301 each operable for a nominally elastic deformation of at least 10%. (Middle portion 1304 contains or otherwise at least overlaps elastic portion 1301.) In some variants system 1300 is configured with one or more such elastic portions 1301 totaling at least half of (an entire length of) tether 1308. Alternatively or additionally, tethers described herein may comprise one or more inelastic portions 1302 (of middle portion 1304) optionally including a notch or other configured breakage mechanism. In some contexts, nominally "inelastic" length portions normally deform permanently or break if stretched by 10% or more.

In some embodiments, a "semi-soluble" element is one that is configured to break down in more than an hour but less than a week, and a "substantially insoluble" element is less soluble than this. Numerous water insoluble polymers may be used to reduce a compound's solubility, for example, such as cellulose derivatives (i.e., ethylcellulose), polyvinyl acetate, neutral copolymers based on ethyl acrylate and methylmethacrylate, copolymers of acrylic and methacrylic acid esters with quaternary ammonium groups, or the like. In some embodiments, polymers used in forming such less-soluble elements may be plasticized. Examples of plasticizers that may be used for this purpose include, but are not limited to, triacetin, tributyl citrate, triethyl citrate, acetyl tri-n-butyl citrate diethyl phthalate, castor oil, dibutyl sebacate, acetylated monoglycerides, or the like and/or substantially any combination thereof. In some embodiments, one or more such plasticizers may be present at about 5 to 50 weight percent and more typically about 10 to 25 weight percent based on the polymer to which the plasticizer is added. The type of plasticizer and its content depends on the polymer or polymers and/or the nature of the coating system.

In some embodiments, water-soluble nonionic polysaccharide derivatives may be used to wrap one or more therapeutic agents for rapid release. For example, hydroxypropylmethylcellulose, hydroxypropylcellulose, and/or sodium carboxymethylcellulose may be used. Such polymers form coatings that quickly dissolve in digestive fluids or water and have a high permeability. Accordingly, in some embodiments, such polymers may be used for rapid release of one or more therapeutic agents that are wrapped in such a wrapper following administration to an individual.

In some embodiments, one or more therapeutic agents may be wrapped in a wrapper that provides for sustained release of the one or more therapeutic agents. For example, one or more therapeutic agents may be released continuously over twelve hours through use of wrappers constructed from ethyl cellulose and an ethyl acrylate-methyl methacrylate-ethyl trimethylammoniumchloride methacrylate copolymer as the release controlling wrapper. Existing methods and materials that may be used to prepare such wrappers are known by those skilled in the art and are commercially available (i.e., Rohm Pharma, Piscataway, N.J.; U.S. Pat. Nos. 6,656,507; 7,048, 945; 7,056,951; hereby incorporated by reference to the extent not inconsistent herewith).

In some embodiments, tethers described herein may be made integrally with one or more modules and/or include one or more strands of surgical thread, polymer, or other materials of suitable elasticity and strand structure. In many contexts, tether 1308 may be implemented to include one or more other instances of soluble portions 1305, dispensers 1350 or inelastic portions 1306 (of middle portion 1304). In some variants, for example, inelastic portion 1306 may be configured to separate when loaded with more than a calibrated tension T, where T is at least 1-10 pounds and/or at most 10-100 pounds. Tether 1308 may, for example, be configured as a compound structure that includes one or more modules joining two or more tether segments end-to-end. Tether 1268 may likewise be formed as a loop, for example, by module 1261 grasping both ends of a simple tether passing through other modules 1262, 1263.

Figure 14:
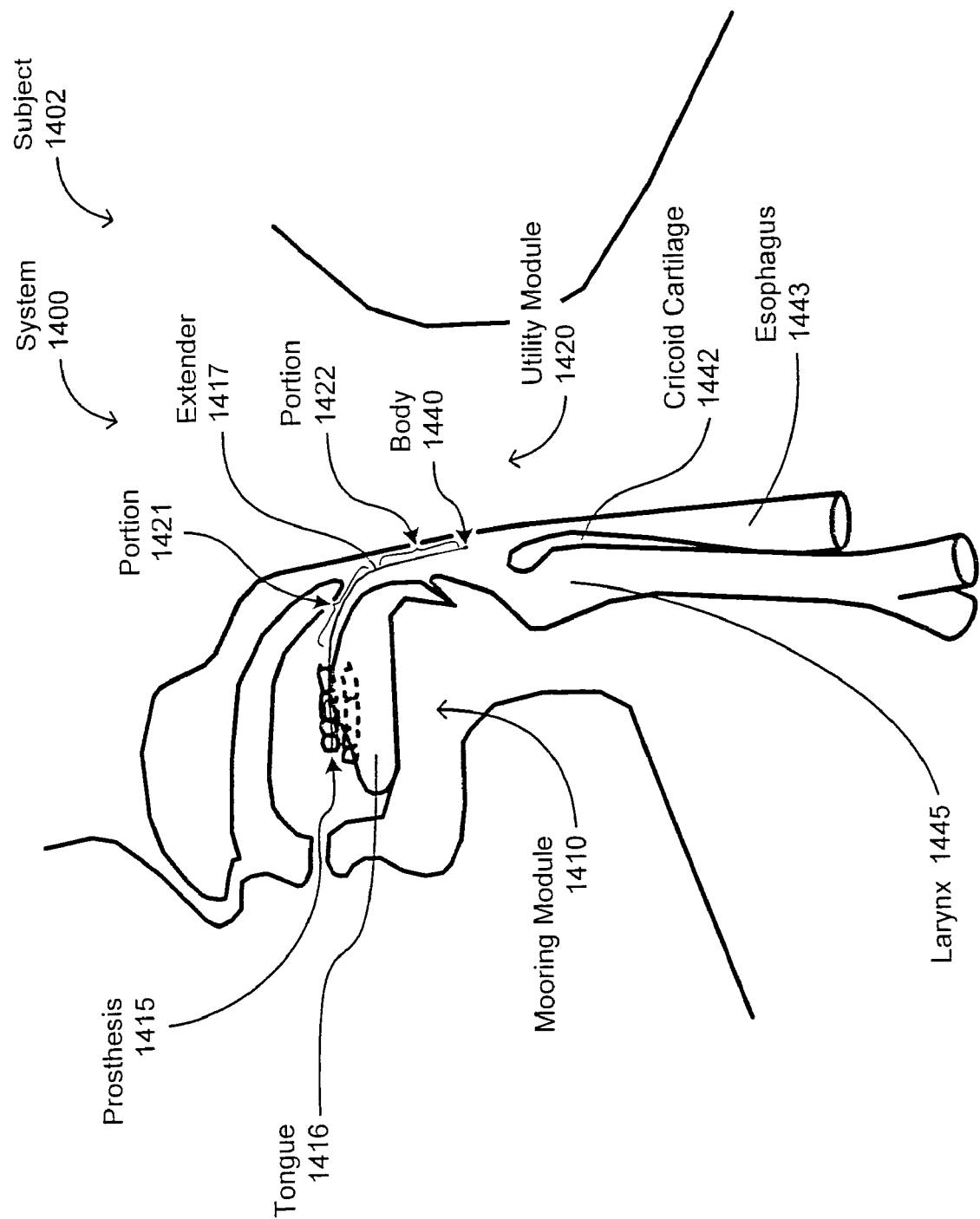

With reference now to FIG. 14, shown is a system positioned at least in a vicinity subject 1402 in which one or more technologies may be implemented. System 1400 may comprise one or more medical or veterinary utility modules 1420 comprising one or more bodies 1440 supported via one or more adaptable extender modules comprising a (rigid or other) prostheses 1415 or other support within the head and/ or neck position and one or more supple extenders 1417 therefrom. Alternatively or additionally, such extenders or their portions 1421, 1422 may likewise be supported nasal stents, surgical staples in cranial or throat positions (such as the hard palate, nasal cartilage, or cricoid cartilage 1442, for example), nasal stents, or other such local modules 1410. Exemplary structures and modes of operation may be found, for example, in U.S. patent application Ser. No. 11/417,898 ("Controllable release nasal system"), having overlapping inventors herewith, incorporated by reference herein. See also U.S. patent application Ser. No. 11/716,645 ("Orthonostric device and method of forming the same"). In some variants, extender 1417 may pass beside tongue 1416 and optionally into a side of the throat of subject 1402 with minimal interaction with the soft palate. Alternatively or additionally, a tether or other portions 1421, 1422 of one or more extenders 1417 may be coated along at least some of their length with an anesthetic-containing material.

Such tethers or other such supple structures may extend into esophagus 1443 or other parts of subject 1402, as described further below. Body 1440 may comprise one or more auditory or other sensors as described herein. Body 1440 may likewise comprise one or more dispensers, particularly those having a flow path from reservoir positions at oral and/or gastric modules 141, 144 (as shown in FIG. 1). In some variants, an upper portion 1421 of extender 1417 has a flexural modulus of at least about 10 megapascals. Alternatively or additionally, a lower portion 1422 has a flexural modulus of at most about 20 megapascals. Such extenders may likewise include one or more active components (not shown) operable to bend one or more coupling to keep mucous membrane irritation at an acceptably low level.

With reference now to FIG. 15, shown is an example of a system 1500 immersed in digestive fluid 1565. System 1500 comprises several modules 1501, 1502, 1503, 1504 strung onto a single common tether 1538 having an average diameter 1597 less than 10% of length 1596. The modules 1501-1504 may be held together by one or more capsules 1580 and/or bands 1590 to facilitate ingestion. As shown, system 1500 may (optionally) include one or more longest modules 1503, 1504 having a length 1596 about 1-2 times that of an eyeball of the subject). For a typical human adult, for example, such a length 1596 may be longer than 5 centimeters and/or less than 6 centimeters.

With reference now to FIG. 16, shown is an end view of system 1500 (as viewed from the right, relative to FIG. 15). Each of modules 1501-1504 has roughly the same diameter 1693 as one another, as shown, within a factor of 2. Alternatively or additionally, one or more of modules 1501-1504 may likewise have roughly the same length as length 1596, within a factor of 2.

With reference now to FIG. 17, shown is an end view of system 1500 (as viewed from the left, relative to FIG. 15). Unlike the view in FIG. 16, tether 1538 appears roughly horizontal, stretched between respective tabs 1791, 1794. Each of modules 1501-1504 has one or more tabs 1791, 1794 at each end as shown.

With reference now to FIG. 18, shown is an example of a medical or veterinary system 1800 comprising the modules 1501-1504 of FIGS. 15-17 in a fully expanded configuration. Tether 1538 may be configured as a taut loop in this configuration, effectively coupling each pair of these modules 1501-1504 via a bore or other gap 1839 in each of the modules. In a variant in which one or more device(s) 1811, 1815 is configured to sever or otherwise release respective ends of tether 1538 within gap 1839 of module 1501, for example, the gaps 1839 of one or more other modules 1502-1504 are large enough to permit tether 1538 to slip free so that all of the modules 1501-1504 may pass separately and safely per vias naturales. Such device(s) 1811, 1815 may (optionally) be configured to effect such a release in response to one or more of a temperature change indicating entry into a stomach, a pH change of more than 2 points or some other indication of a sensed position, a remote control signal, an excessive tension in tether 1538, or some other indication that system 1800 should or should not be fully expanded in a subject's current circumstances. Such device(s) 1811 may be configured to permit a clinical care provider to prevent or abort a deployment in the event that system 1800 has apparently begun to deploy in an esophagus or small intestine, for example. In some variants, such a ring-type module may support a tube or other tether extending out of a gastric compartment as described herein.

For a typical human adult, a deployed diameter 1895 may (optionally) be longer than 6 centimeters and/or less than 8 centimeters. As shown, modules 1501-1504 each has a nominal module length more than twice as long as its (respective) average cross-sectional diameter 1693. At least one of the modules 1503 may (optionally) have exactly one reservoir 1853. In some variants, each such reservoir 1852, 1853 may contain a respective therapeutic agent or a partial dosage of a common therapeutic agent. Alternatively or additionally, each such reservoir 1852, 1853 may be configured for dispensation under respectively different conditions. In some variants, for example, one or more other reservoirs 1851, 1854 may comprise a dispenser containing one or more of an antiviral or other antimicrobial agent, or some other component of a complex therapeutic regimen. In some variants, one or more such reservoirs 1851-1854 may comprise one or more of an anti-seizure medication, warfarin or other anticoagulant medications, insulin or other hormones, or other dosage-sensitive therapeutic agents.

To achieve the expanded configuration of system 1800 conveniently, at least some of tether 1538 may (optionally) be constructed of a sufficiently elastic material able to be stretched by at least about 5-10% with negligible damage. Alternatively or additionally, some or all of tether 1538 may be constructed to contract in an aqueous and/or acidic environment. Alternatively or additionally, one or more modules 1501-1504 may advantageously comprise an initially compressed body (especially as shown in FIG. 15), a body that swells in an aqueous and/or acidic environment, a shape memory element, and/or some other suitable uptake mechanism. Many such existing uptake mechanisms may be effectively implemented for this purpose (in device 1814, for example) without undue experimentation, as exemplified in U.S. patent application Ser. No. 11/975,371, titled "Disintegrating Tract Interaction System," filed 17 Oct. 2007], also by Boyden et al. Such an active uptake mechanism may be triggered by a disengagement of band 1590, a significant increase of ambient conductivity (and/or pressure or temperature, e.g.), or some other deployment-indicative condition. Other changes can occur as a mechanical or automatic response to such changes, such as a relaxation in crease 1834 causing port 1835 to open.

Figure 19:
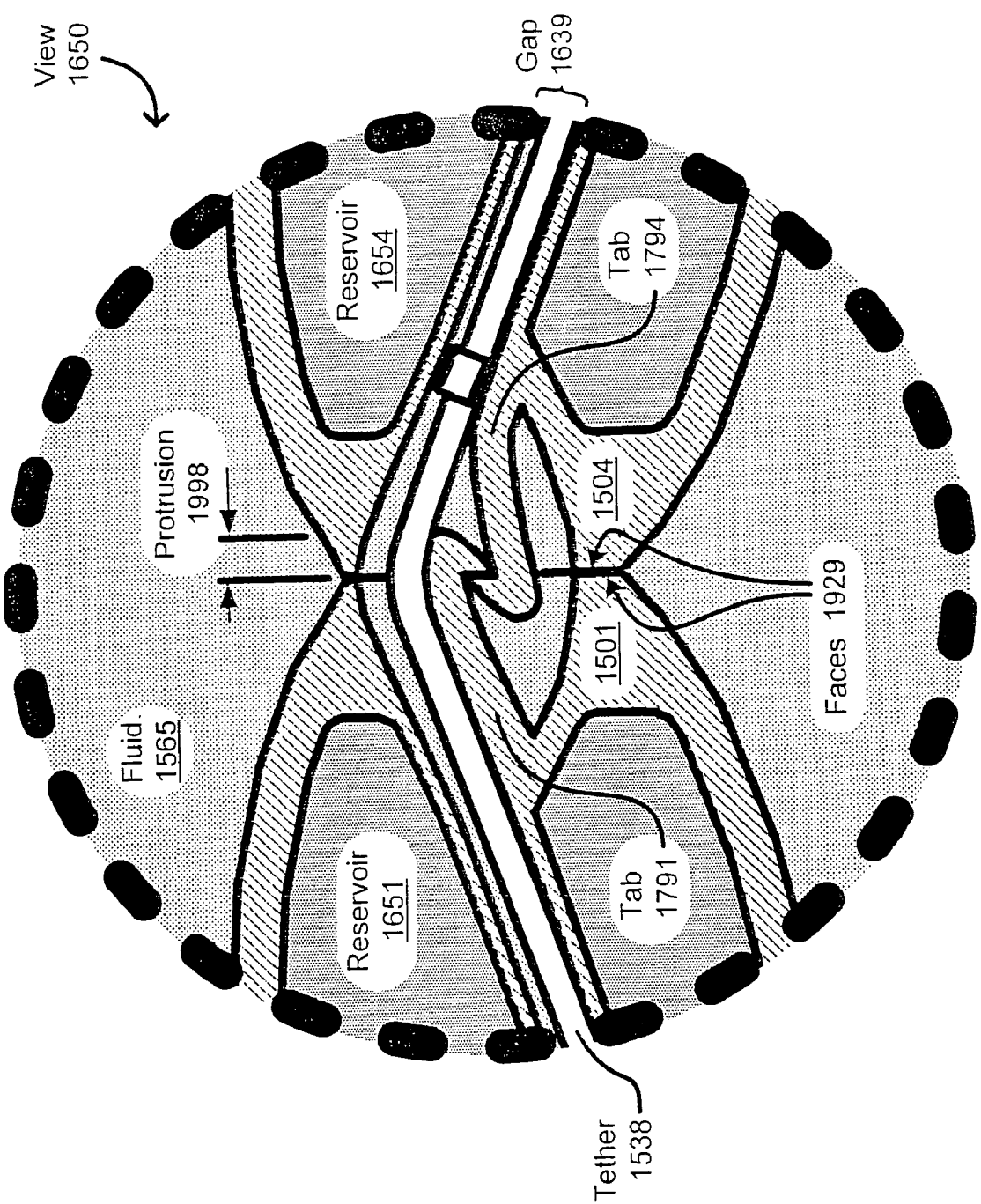

With reference now to FIG. 19, shown is a partial view 1850 of the expanded medical or veterinary system 1800 of FIG. 18, magnified and in cross-section. Here it is apparent that module 1501 comprises reservoir 1851 and a sleeve or other gap 1839 through which tether 1538 passes. Module 1504 likewise comprises reservoir 1854 and a sleeve or other gap 1839 through which tether 1538 also passes. Tether 1538 effectively couples module 1501 with module 1504 through gap 1839 as shown. Tether 1538 also has a "middle portion" (in FIG. 18) configured to slip free from modules 1502, 1503 responsive to tether 1538 dissolving, breaking, or otherwise decoupling module 1501 from module 1504.

To maintain an expanded configuration like system 1800 in a gastric compartment, in some variants, each adjacent pair of modules may advantageously include a magnetic, adhesive, mechanical, or other latching feature such as tabs 1791, 1794 operable to extend into an adjacent module, for example. Such tabs 1791, 1794 may latch together (as shown in FIG. 19) or otherwise engage as respective faces 1929 thereof are drawn adjacent one another by tension in tether 1538 (in response to immersion in fluid 1565, for example). The protrusion 1998 of tab 1791 into module 1504 may (optionally) be about one millimeter or less, as shown. In some variants, moreover, such an engagement mechanism may release or relax in response to a slackening of tether 1538. This can occur, for example, in a configuration in which tab 1791 bears (upward as shown) against tether 1538, optionally enough to release tab 1794 in response to an absence of force (downward as shown) exerted by tether 1538.

Figure 20:
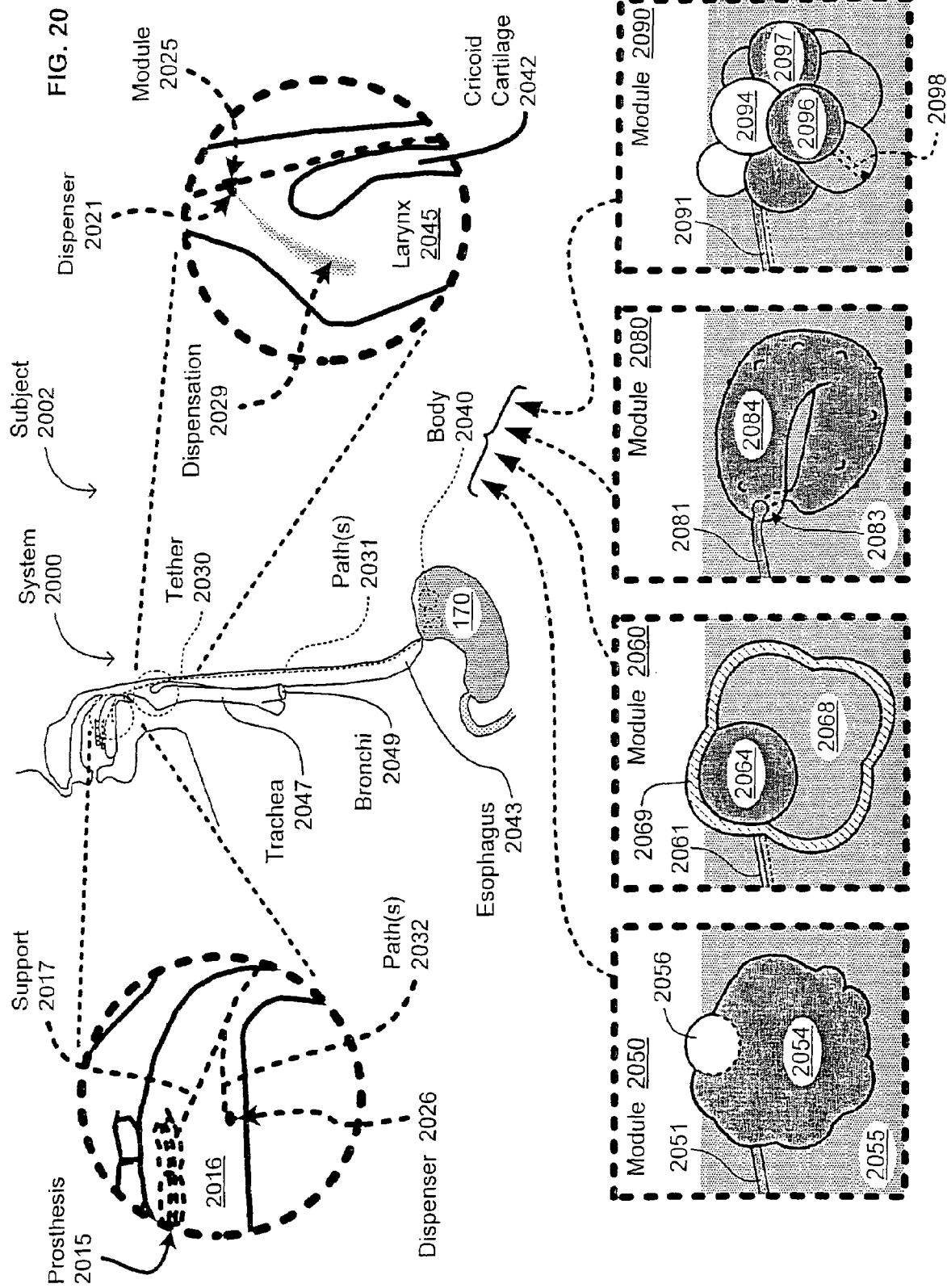

With reference now to FIG. 20, shown is a tract portion and adjacent anatomical structures of a subject 2002 in a vicinity of which one or more technologies may be implemented. System 2000 may comprise one or more bodies 2040 respectively or collectively coupled with or via one or more tethers 2030 extending within or outside gastric compartment. In some variants, such tethers may extend downward (see FIG. 1) or upward into or through esophagus 2043. Tether 2030 may (optionally) extend to one or more dispensers 2021 and/or other modules 2025 in a vicinity of larynx 2045 or trachea 2047, for example, optionally permitting one or more therapeutic material dispensations 2029 (e.g. in pulmonary administrations via bronchi 2049). In various embodiments, such dispensations may comprise a mist, aerosol or other suspension, mixture, or other material combination as described herein. Such tethers may be supported by one or more dental prosthetheses 2015 via one or more supports 2017, or by simply being tied around a tooth. In some variants, support 2017 passes beside tongue 2016 and optionally into a side of the throat of subject 2002 with minimal interaction with the subject's soft palate. Alternatively or additionally, tether 2030 may be supported by being coated along its length with an anesthetic-infused adhesive, by being supported by a surgical staple or other implanted structure (e.g. at cricoid cartilage 2042), and/or by being fastened to one or more nasal stents or other such anatomical interface structures suitable for use in the present context. See, e.g., U.S. patent application Ser. No. 11/716,645 ("Orthonostric device and method of forming the same").

For insulin or other hormones, or hormone mimics, or for many other bioactive substances described herein, a formulation may be provided in a sufficiently concentrated form so that about 1 to 50 milligrams per day (or per dispensation) thereof is therapeutically effective. Such volumes are sufficient for treating a variety of pathologies according to existing inhaler regimens, for example, or for compliance with other physician-specified regimens, or for more appropriate responses to emergency situations. For a liquid formulation of this type, for example, dispenser 2021 may include a porous membrane through which a liquid formulation passes for aerosolization. A variety other suitable forms of dispenser 2021 are also readily implemented in light of teachings herein. See, e.g., U.S. Pat. No. 7,066,029 ("System and method for improved volume measurement"); U.S. Pat. No. 7,028,686 ("Inhaled insulin dosage control delivery enhanced by controlling total inhaled volume"); U.S. Pat. No. 6,889,690 ("Dry powder inhalers, related blister devices, and associated methods of dispensing dry powder substances and fabricating blister packages"); U.S. Pat. No. 6,655,379 ("Aerosolized active agent delivery").

In some variants, system 2000 may include one or more signal or other flow path(s) 2031 through or along tethers as described herein. One or more such paths 2031, 2032 may extend to a sublingual dispenser 2026, for example, or to or from a location in the throat, nasal passage, intestine 1080 (of FIG. 10), or other site in a vicinity of tract 1001 and/or subject 2002. In some variants, for example, a signal flow path responsive to a nutrient level detected at sense module 1022 may (optionally) travel up tether 1037 to one or more modules in gastric chamber 1070 implementing one or more of modules 1010, 1050 comprising body 2040, for example. Such detectable nutrients may comprise one or more instances of proteins, fats, vitamins, minerals, trace elements, carbohydrates, or substantially any ratio or other combination thereof. Such detection may comprise a determination whether one or more measurements indicative of one or more such nutrients (or a determinant derived from them) are within a nominal range derived from empirical data, for example, or at a lower-than-nominal level or a non-ideal level.

Such signal flow may then undergo a programmatic aggregation or delay and/or change form (from optical or electrical to a pressure or other mechanical manifestation, for example) before triggering dispensation via one or more dispensers 1021, 2021, 2026 optionally provided in systems 1000, 2000 described herein. In some variants, moreover, such dispensation may be administered to other sites, such as by routing a small flow tube into a blood vessel or other location in the abdominal cavity through an incision in the esophagus.

In some variants, body 2040 may have an annular configuration of a general type exemplified in U.S. Pat. No. 4,758,436 ("Drug delivery device which may be retained in the stomach for a controlled period of time"). Alternatively or additionally, body 2040 may have attributes of one or more other instances of modules 2050, 2060, 2080, 2090 described next.

In an instance in which body 2040 includes one or more attributes of module 2050, for example, body 2040 may comprise a single reservoir 2054 and/or a single-reservoir port 2051 for dispensing one or more therapeutic materials as described herein. Module 2056 further comprises a bladder or other such lower-density internal structure so that module 2050 is at least somewhat buoyant relative to fluid 2055 as shown.

In an instance in which body 2040 includes one or more attributes of module 2060, for example, body 2040 may comprise a primary reservoir 2064 and one or more other reservoirs 2068 in respective chambers of a common container 2069, optionally having higher-than-ambient pressure (by at least 1%, for example, in absolute terms). In a variant in which primary reservoir 2064 contains one or more bioactive agents, reservoir 2068 may comprise a carrier, for example, or a pressure-maintaining reservoir. In some contexts it may be preferable that container 2069 itself have a density larger than 1.1 g/ml. This may permit reservoir 2068 to contain a gaseous component for example, even without bringing the overall density of module 2060 below 0.8 g/ml. Alternatively or additionally, module 2060 may adjoin one or more conduits or other ports 2061 configured for permitting a valve elsewhere to release bioactive substances therein.

In an instance in which body 2040 includes one or more attributes of module 2080, for example, body 2040 may comprise a reservoir 2084 with an irregular outer surface and/or one or more gaps 2083, actuators, or other features for facilitating a change in a configuration thereof in situ. To further understand the operation of such features, see, e.g., U.S. patent application Ser. No. 11/702,888 ("Gastro-intestinal device and method for treating addiction") or U.S. Pat. No. 6,994,095 ("Pyloric valve corking device and method"). By drawing tether 2081 through gap 2083 with a catheter or other manipulation device, for example, pressure one on or more fluids inside reservoir 2084 may be increased in situ.

In an instance in which body 2040 includes one or more attributes of module 2090, for example, body 2040 may comprise a plurality of reservoirs 2094, 2096 having respectively different therapeutic substances therein, one or more of which may be directly releasable through their openings 2098. Tether 2091 may likewise include flow paths in either direction (for inflating or dispensing from reservoir 2094, for example, or for bearing electrical signals in either or both directions). Module 2090 may, in particular, combine two or more respective features of reservoir-containing modules 2050, 2060, 2080 described above, in each of the (component) reservoirs 2094, 2096, 2097 shown. In some variants, moreover, one or more such reservoirs 2097 is configured for selective release as exemplified in relation to FIG. 22.

Figure 22:
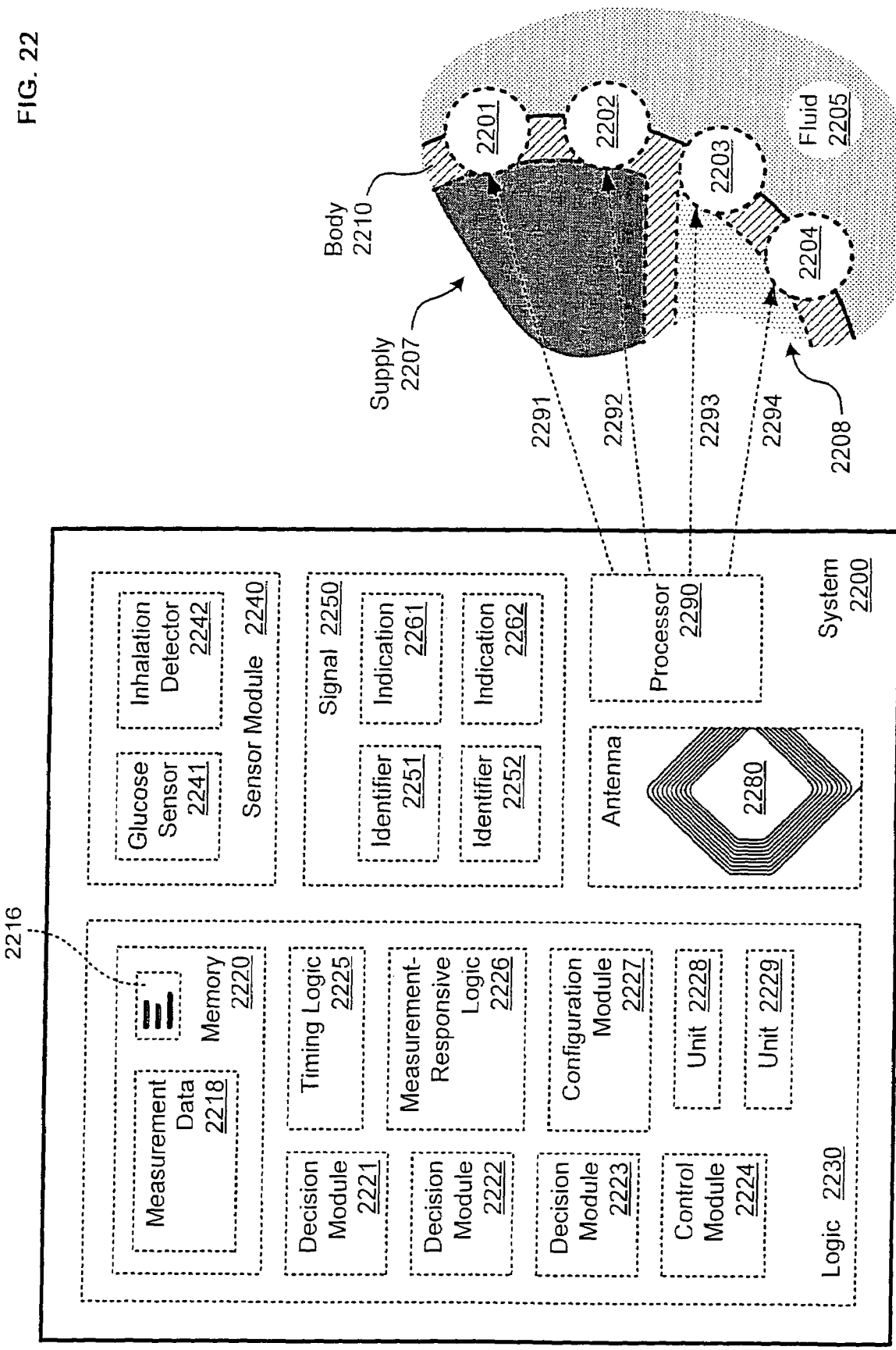

With reference now to FIG. 22, shown is system 2200 for use in or with body 2210 immersed adjacent fluid 2205 in which one or more technologies may be implemented. System 2200 may comprise one or more instances of instruction sequences 2216, measurement data 2218 and/or other logic 2230, some or all of which may reside in static or dynamic memory 2220. Such logic 2230 may comprise one or more instances of decision modules 2221, 2222, 2223 or other control modules 2224; timing logic 2225; measurement-responsive logic 2226; configuration modules 2227; or other logic units 2228, 2229. Alternatively or additionally, system 2200 may comprise one or more instances of glucose sensors 2241, inhalation detectors 2242, in situ sense modules, or other sensor modules 2240 as described herein. These and other components of system 2200 may be configured to bear one or more instances of identifiers 2251, 2252 or indications 2261, 2262, such as one or more antennas 2280 or processors 2290 optionally provided therein. In addition to one or more instances of system 2200, body 2210 may comprise one or more ports or other continuous dispensers 2201 (or one or more releasable capsules or other discrete dispensers 2202) configured for dispensing from a bioactive material supply 2207. Body 2210 may likewise comprise one or more ports or other continuous dispensers 2203 (or one or more releasable capsules or other discrete dispensers 2204) configured for dispensing from at least one other bioactive-material-containing supply 2208. As shown, one or more processors may implement a bioactive material selection directly or indirectly, in respective embodiments, by selectively outputting one or more actuator driver outputs 2291, 2292, 2293, 2294 respectively operable for initiating or otherwise controlling dispensation from dispensers 2201-2204 as shown.

In some variants, system 2200 is configured for performing one or more variants of flow 200 (of FIG. 2) described herein. In an embodiment in which antenna 2280 is configured to perform operation 220, for example, antenna 2280 may likewise receive a wireless signal (as signal 2250) indicative of one or more ports, supplies, or other dispensers inside tract 1001, for example. In response, one or more decisions module 2221-2223 may (optionally) be configured to signal a decision of which actuator or other dispenser control of a module to activate in response to a received wireless signal.

In light of these teachings, numerous existing techniques may be applied for constructing capsules or other ingestible or releasable structures as described herein without undue experimentation. See, e.g., U.S. Pat. No. 7,182,959 ("Rapidly dissolving dosage form and process for making same"); U.S. Pat. No. 6,962,715 ("Method and dosage form for dispensing a bioactive substance"); U.S. Pat. No. 6,960,356 ("Orally administered drug delivery system providing temporal and spatial control"); U.S. Pat. No. 6,929,636 ("Internal drug dispenser capsule medical device"); U.S. Pat. No. 6,936,279 ("Microcrystalline zeaxanthin with high bioavailability in oily carrier formulations"); U.S. Pat. No. 6,866,863 ("Ingestibles possessing intrinsic color change"); U.S. Pat. No. 6,767,567 ("Ingestible elements"); U.S. Pat. No. 6,703,013 ("Polystyrene sulfonate-containing gel preparation"); U.S. Pat. No. 6,677,313 ("Method for gene therapy using nucleic acid loaded polymeric microparticles"); U.S. Pat. No. 6,475,521 ("Biphasic controlled release delivery system for high solubility pharmaceuticals and method"); U.S. Pat. No. 6,638,533 ("Pulse dosage formulations of methylphenidate and method to prepare same"). Those skilled in the art will also recognize how to apply numerous existing techniques for taking provisional, alternate, overlapping, or completion actions relating to such applications as exemplified herein without undue experimentation, in light of these teachings. Substantially any of these structures or techniques may be used in some form for constructing modules, flow paths, dispensers, or other feature described herein without undue experimentation.

Figure 21:
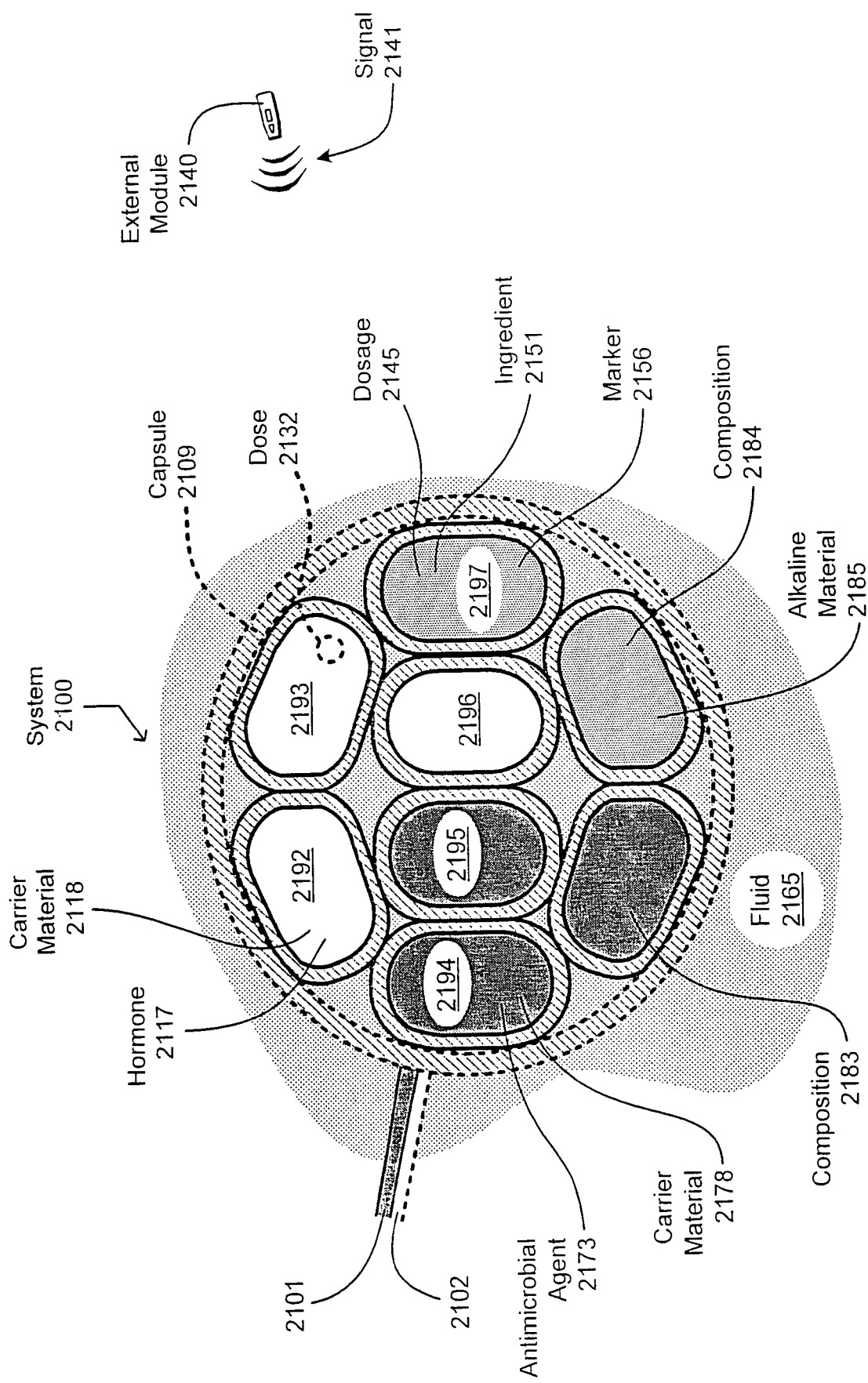

With reference now to FIG. 21, shown is an implantable or ingestible system 2100 suitable for exposure to digestive or other bodily fluid 2165 in which one or more technologies may be implemented. System 2100 may comprise two or more reservoirs 2192, 2193, 2194, 2195, 2196, 2197 operating in a cooperative fashion according to an a priori regimen and/or sensor input or other signals 2141. Such signals may originate from a remote care provider or other external module 2140, for example, optionally after being received locally via a wireless medium. External module 2140 may comprise a wireless router, a radio-frequency identification (RFID) device, and/or a handheld device, for example. Alternatively or additionally, external module 2140 may comprise an article configured to function while worn by a subject, such as a belt or prosthetic device.

One or more such reservoirs 2192-2197 may be configured to separate from the others for dispensation during passage per vias naturales in some embodiments. Alternatively or additionally, one or more others may be configured for selective dispensation via one or more ports 2101, 2102 to respective flow paths as described herein, for example. Such flow paths may pass into an esophagus and/or an intestine, for example, as variously described herein.

As shown, reservoir 2192 may comprise one or more instances of hormones 2117 or other bioactive ingredients and/or carrier materials 2118. Reservoir 2193 may likewise comprise many doses 2132 of a bioactive powder, propellant, or other flowable material. Reservoir 2194 may comprise one or more instances of antimicrobial agents 2173 and/or other bioactive ingredients optionally comprising carrier materials 2178. Reservoir 2197 may comprise a selectable concentration or other mode of dosage 2145, optionally with one or more other instances of ingredients 2151 or other markers 2156.

System 2100 may further comprise one or more other compositions 2183, 2184, one or more of which may comprise one or more instances of alkaline materials 2185 or other materials useful for adjusting pH. Optionally some or all such reservoirs may be housed within one or more capsules 2109, optionally at a stable, higher-than-ambient pressure and near-neutral buoyancy. In other variants, however, creases or other hinging structures may be used for coupling respective ones of reservoirs 2192-2197 into one or more ring-like, H-shaped, tetrahedral, or other expanded forms useful for "loitering" for more than a day in a gastric chamber, for example, as described herein.

Figure 23:
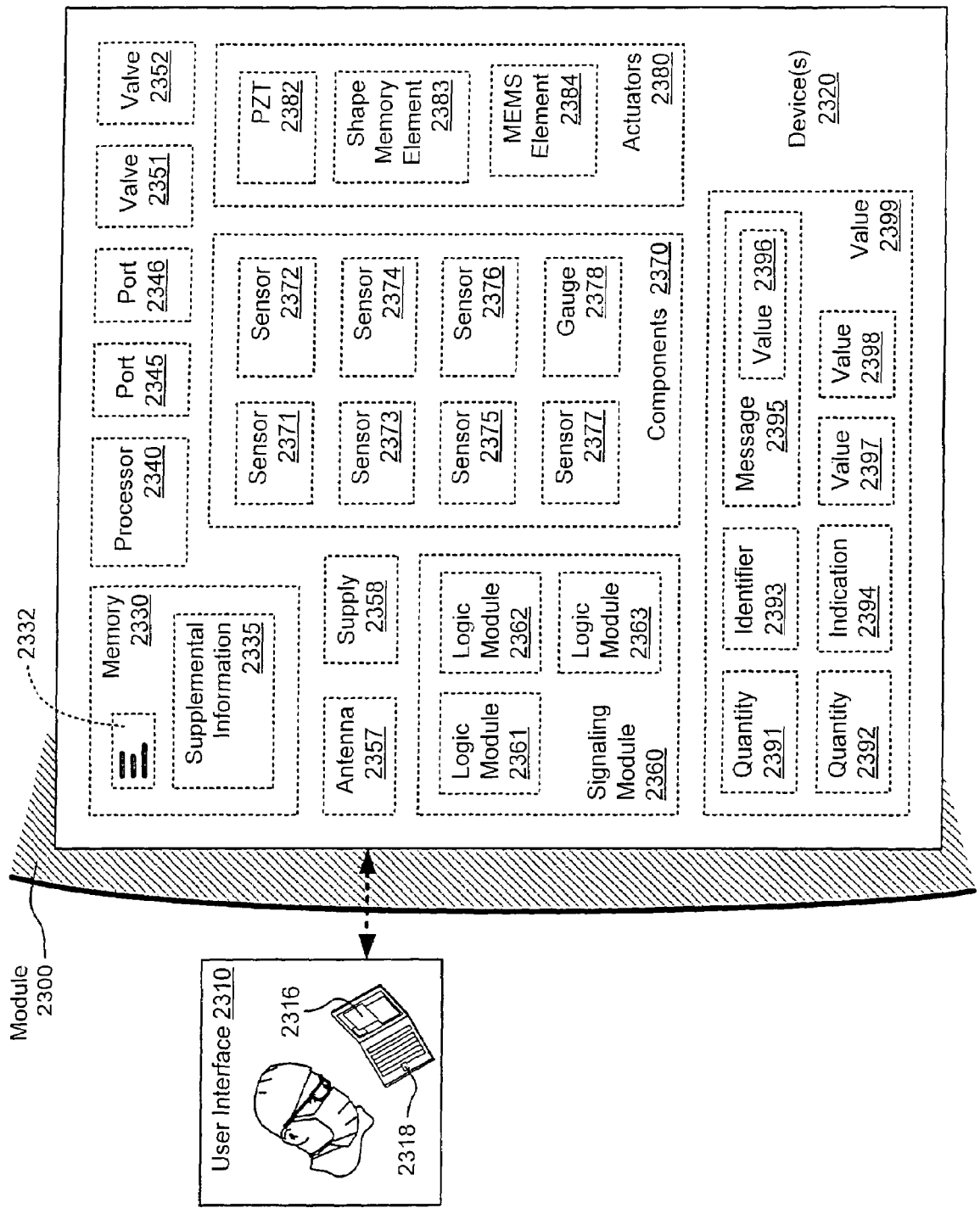

With reference now to FIG. 23, shown is a system in which one or more technologies may be implemented comprising one or more modules 2300 optionally operable for communication with one or more user interfaces 2310 operable for relaying user output 2316 and/or input 2318. Module 2300 comprises one or more instances of (electrical, electromechanical, software-implemented, firmware-implemented, or other control) devices 2320. Device 2320 may comprise one or more instances of memory 2330; processors 2340; ports 2345, 2346; valves 2351, 2352; antennas 2357; power or other supplies 2358; logic modules 2361, 2362, 2363 or other signaling modules 2360; gauges 2378 or other such active or passive detection components 2370; or piezoelectric transducers 2382, shape memory elements 2383, micro-electromechanical system (MEMS) elements 2384, or other actuators 2380. Such detection components 2370 may comprise one or more instances of sensors 2371 operable for measuring or otherwise detecting a higher-than-nominal concentration of alcohol or other controlled substances, sensors 2372 operable for accepting an indication of or otherwise responding to a proximity to an artificial device from within a portion of the tract, sensors 2373 for measuring or otherwise detecting a higher-than-nominal concentration of an artificial control marker, sensors 2374 operable for measuring or otherwise detecting a higher-than-nominal concentration of lipids, sensors 2375 operable for accepting an indication of or otherwise responding to a pH or other environmental attribute, sensors 2376 operable for measuring or otherwise detecting a higher-than-nominal concentration of carbohydrates or other nutrients, or sensors 2377 operable for accepting an indication of or otherwise responding to a departure of one or more artificial devices from within a specific portion of the tract. Many such devices may be implemented in software or otherwise in memory 2330, such as one or more executable instruction sequences 2332 or supplemental information 2335 as described herein. Alternatively or additionally, in various embodiments, any such devices 2320 may likewise (optionally) handle one or more instances of quantities 2391, 2392; one or more identifiers 2393 or other indications 2394; or other components of messages 2395 or other values 2396, 2397, 2398, 2399 as described herein.

In light of teachings herein, numerous existing techniques may be applied for acquiring or using measurements or other detectable phenomena relating to a tract for various functions as described herein without undue experimentation. See, e.g., U.S. Pat. No. 7,217,245 ("Noninvasive methods for detecting abnormalities in a subject such as disease or dysfunction"); U.S. Pat. No. 7,160,731 ("Examination method of buffer capacity of saliva and examination instrument of buffer capacity of saliva"); U.S. Pat. No. 7,155,269 ("Stress evaluation apparatus"); U.S. Pat. No. 7,062,306 ("Spectroscopy illuminator with improved delivery efficiency for high optical density and reduced thermal load"); U.S. Pat. No. 6,365,128 ("Monitoring gastrointestinal function to guide care of high risk patients"); U.S. Pat. No. 6,264,611 ("Monitor for interventional procedures"); U.S. Pat. No. 6,258,046 ("Method and device for assessing perfusion failure in a patient by measurement of blood flow"); U.S. Pat. No. 6,125,293 ("Method for determining the pH in the mucosa of the stomach or the gastrointestinal tract"); U.S. Pat. No. 5,833,625 ("Ambulatory reflux monitoring system"); U.S. Pat. No. 5,263,485 ("Combination esophageal catheter for the measurement of atrial pressure"). Many such variations may be implemented in special purpose instructions or code 2332 in memory 2330 or other such components 2370, for example, optionally implemented in special purpose circuitry comprising one or more sensors 2371-2377 or other components 2389 configured for automatic decision making. Combinations of these may each be effectuated by comparative, arithmetic, conjunctive, or other operators relating each pairing of input 2318 or other detectable determinants described with reference to FIG. 23, for example.

In light of teachings herein, numerous existing techniques may be applied for acquiring or using measurements or other detectable phenomena relating to a tract for various functions as described herein without undue experimentation. See, e.g., U.S. Pat. No. 7,217,245 ("Noninvasive methods for detecting abnormalities in a subject such as disease or dysfunction"); U.S. Pat. No. 7,160,731 ("Examination method of buffer capacity of saliva and examination instrument of buffer capacity of saliva"); U.S. Pat. No. 7,155,269 ("Stress evaluation apparatus"); U.S. Pat. No. 7,062,306 ("Spectroscopy illuminator with improved delivery efficiency for high optical density and reduced thermal load"); U.S. Pat. No. 6,365,128 ("Monitoring gastrointestinal function to guide care of high risk patients"); U.S. Pat. No. 6,264,611 ("Monitor for interventional procedures"); U.S. Pat. No. 6,258,046 ("Method and device for assessing perfusion failure in a patient by measurement of blood flow"); U.S. Pat. No. 6,125,293 ("Method for determining the pH in the mucosa of the stomach or the gastrointestinal tract"); U.S. Pat. No. 5,833,625 ("Ambulatory reflux monitoring system"); U.S. Pat. No. 5,263,485 ("Combination esophageal catheter for the measurement of atrial pressure"). Those skilled in the art will also recognize how to apply numerous existing techniques for taking provisional, alternate, overlapping, or completion actions relating to such decisions as exemplified herein without undue experimentation, in light of these teachings. Such variations may be implemented in instruction sequence 2332 or other implementations of special-purpose logic implementing one or more functions described herein.

In light of these teachings, numerous existing techniques may be applied for directly or indirectly affecting a pH of a local portion of a tract as described herein without undue experimentation. See, e.g., U.S. Pat. No. 7,276,252 ("Method and form of a drug delivery device, such as encapsulating a toxic core within a non-toxic region in an oral dosage form"); U.S. Pat. No. 7,144,877 ("Bile-acid derived compounds for enhancing oral absorption and systemic bioavailability of drugs"); U.S. Pat. No. 7,101,567 ("Controlled release preparations having multi-layer structure"); U.S. Pat. No. 6,926,909 ("Chrono delivery formulations and method of use thereof"); U.S. Pat. No. 6,875,793 ("Once-a-day controlled release sulfonylurea formulation"); U.S. Pat. No. 6,797,268 ("Pharmaceutical composition useful in the treatment of peptic ulcers"); U.S. Pat. No. 6,730,327 ("Polymer blends that swell in an acidic environment and deswell in a basic environment"); U.S. Pat. No. 6,726,924 ("Oral liposomal delivery system"); U.S. Pat. No. 6,764,696 ("Effervescent drug delivery system for oral administration"); U.S. Pat. No. 6,692,771 ("Emulsions as solid dosage forms for oral administration"); U.S. Pat. No. 6,600,950 ("Iontophoretic treatment system"). Those skilled in the art will also recognize how to apply numerous existing techniques for taking provisional, alternate, overlapping, or completion actions relating to such applications as exemplified herein without undue experimentation, in light of these teachings. In some variants, one or more reservoirs or dispensers described herein may comprise a pH-reducing or pH-increasing component in a liquid form, for example, optionally configured for release directly into gastric compartments 170, 1070 or other such environments described herein. Alternatively or additionally, such dispensation may be controlled or otherwise informed by one or more sensors 2375 or other components 2370 operable for detecting a pH, a pH change, or one or more other environmental circumstances as designated by a physician or other medical or veterinary professional.

In light of these teachings, numerous existing techniques may be applied for using artificial markers or other diagnostically useful indicator materials as described herein without undue experimentation. See, e.g., U.S. Pat. No. 7,256,398 ("Security markers for determining composition of a medium"); U.S. Pat. No. 7,252,932 ("Methods for the detection, analysis and isolation of nascent proteins"); U.S. Pat. No. 7,238,471 ("Method of diagnosing, monitoring, staging, imaging and treating breast cancer"); U.S. Pat. No. 7,228,159 ("Optical sensor containing particles for in situ measurement of analytes"); U.S. Pat. No. 7,202,045 ("Detection and treatment of cancers of the lung"); U.S. Pat. No. 7,198,756 ("Noninvasive measurement of pH"); U.S. Pat. No. 7,118,919 ("13C glucose breath test for the diagnosis of diabetic indications and monitoring glycemic control"); U.S. Pat. No. 7,118,912 ("Methods and compositions for categorizing patients"); U.S. Pat. No. 7,105,300 ("Sequencing by incorporation"); U.S. Pat. No. 7,070,937 ("Marker useful for detection and measurement of free radical damage and method"); U.S. Pat. No. 6,977,068 ("Method for detection of fibrin clots"); U.S. Pat. No. 6,905,884 ("Fluorescent cobalamins and uses thereof"); U.S. Pat. No. 6,703,045 ("Composition and method for maintaining blood glucose level"); U.S. Pat. No. 6,753,135 ("Biological markers for evaluating therapeutic treatment of inflammatory and autoimmune disorders"); U.S. Pat. No. 6,680,172 ("Treatments and markers for cancers of the central nervous system"); U.S. Pat. No. 6,628,982 ("Internal marker device for identification of biological substances"); U.S. Pat. No. 6,585,646 ("Screening test and procedure using skin patches"); U.S. Pat. No. 6,534,323 ("Compositions and methods for early detection of heart disease"); U.S. Pat. No. 6,500,625 ("Methods for diagnosing cancer or precancer based upon hnRNP protein expression"); U.S. Pat. No. 6,419,896 ("Non-invasive approach for assessing tumors in living animals"); U.S. Pat. No. 5,639,656 ("Antibodies reactive with biological markers of benign prostate hyperplasia"). Those skilled in the art will also recognize how to apply numerous existing techniques for taking provisional, alternate, overlapping, or completion actions relating to such applications as exemplified herein without undue experimentation, in light of these teachings. One or more ports 2345, 2346, valves 2351, 2352, pumps, or other actuators may likewise be used for selecting among two or more bioactive mixtures or other materials, one or more of which may include such marking ingredients.

Referring again to FIG. 13, in some variants, tethers described herein may comprise one or more instances of soluble portions 1303 accessible by fluid 1365 only when exposed by an activation of one or more piezoelectric transducers 2382, shape-memory element 2383, springs, or other actuators 2380. One or more such actuators 2380 may open or otherwise control one or more valves 2351, 2352 selectively in response to components 2370 as described herein, for example. Alternatively or additionally, one or more instances of tethers 1308 may comprise middle portion 1304 at least some of which is semi-soluble or substantially insoluble in one or more digestive fluids 1365 in a typical stomach or other intended environments.

In an embodiment in which system 1300 comprises more than three modules 1310 each small enough to pass through a specific tract, a "fourth" one of modules 1310 may (optionally) engage at least one end (e.g. distal portion 1309) of tether 1308. Alternatively or additionally, in many applications, modules 1310 may be few enough, inert enough, or otherwise implemented on a small enough scale so that their one or more dispensers 1350 may be operable for dispensing a total of at most 15 grams of medicinal material. A fraction of modules 1310 may lack dispensers, for example, especially if configured for one or more other specialty functions. System 1300 may implement a version of tethered group 1290 as described herein, for example, in which module 1292 is inflatable, in which module 1293 comprises one or more implementations of device(s) 2320 operable for external communication, in which module 1294 includes one or more actuators 2380 operable for severing or otherwise manipulating tether 1298, in which module 1295 comprises one or more cameras or other components 2370 operable for data capture, and/or in which module 1296 performs one or more other resource-intensive specialty functions. Such systems 1300 may be assembled from inventories of diverse-looking modules 1210, 1220, 1230, 1240 within a local care facility, for example, based upon information available just before deployment into a tract.

Figure 25:
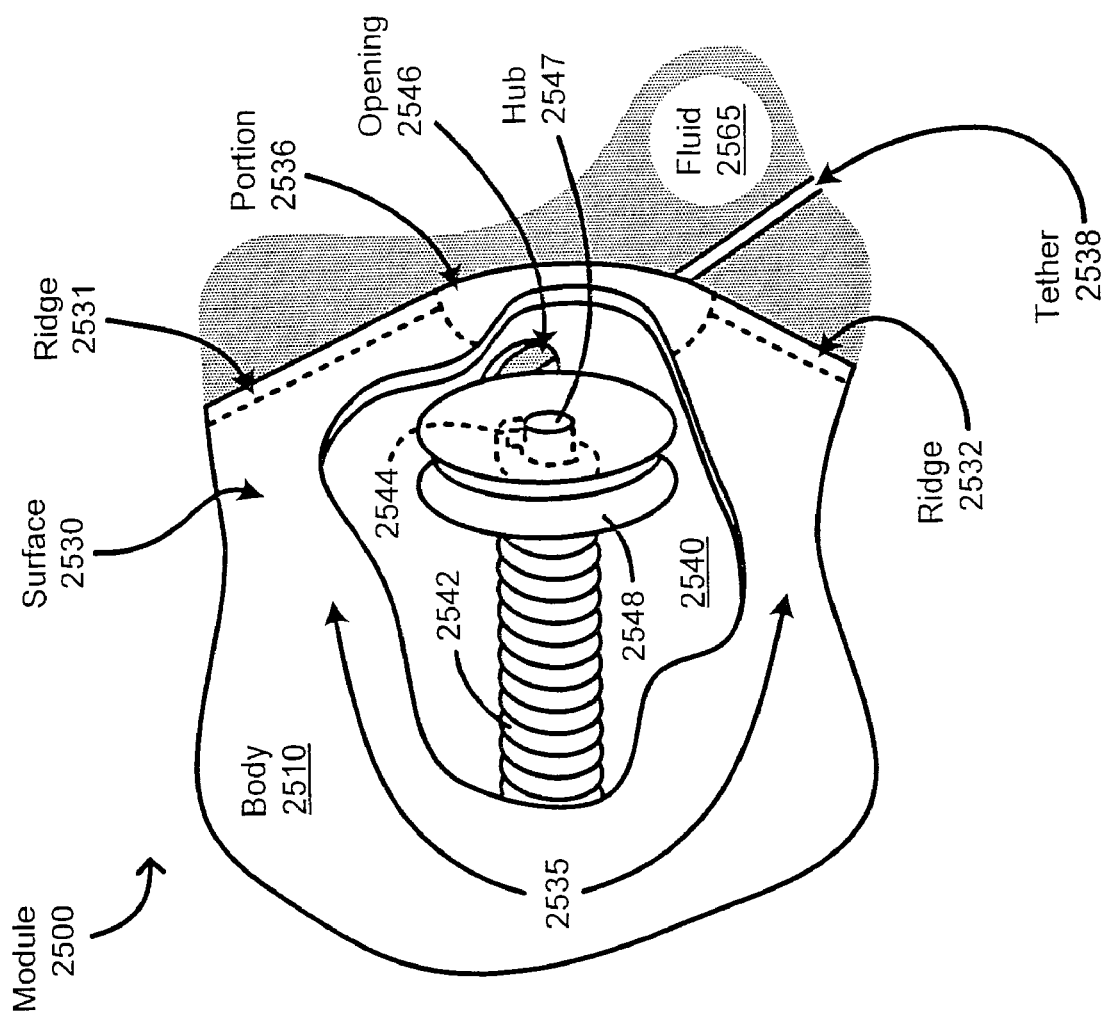

With reference now to FIG. 25, shown is an example of a system that may serve as a context for introducing one or more processes and/or devices described herein. As shown system module 2500 may include at least one unitary body 2510 having an external surface 2530 comprising at least one convex portion 2536, at least one saddle region 2535, at least two (at least partly convex) ridge regions 2531, 2532, and at least one opening 2546. A cutaway reveals chamber 2540 within module 2500 containing at least one spool 2548 operable to retract a (rotationally symmetric or asymmetric) portion of tether 2538 by rotating about hub 2547. Metallic or other deformable windings 2542 are pre-loaded (under tension, e.g.) so that spool 2548 is urged counter-clockwise (as shown), which torque is initially resisted by one or more soluble or semi-soluble latches 2544. When body 2510 is immersed enough so that suitable digestive or other fluid 2565 enters chamber 2540, however, fluid 2565 dissolves the latch(es) 2544, freeing spool 2548 to draw in 1% or more of (the length of) tether 2538.

Figure 26:
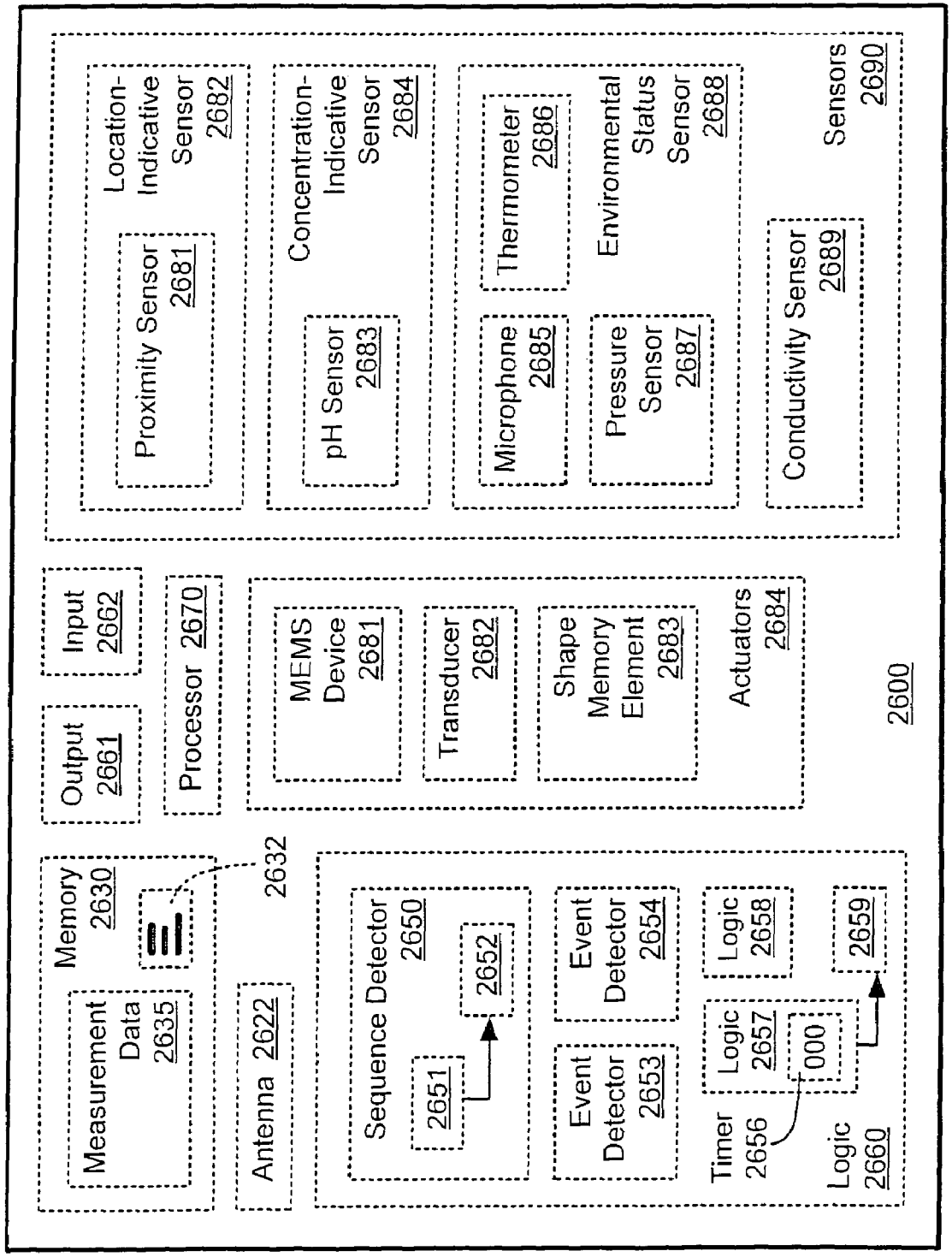

With reference now to FIG. 26, shown is an example of a system that may serve as a context for introducing one or more processes and/or devices described herein. As shown system 2600 may include one or more instances of antennas 2622, memory 2630, logic 2660, output 2661, input 2662, processors 2670, actuators 2684, or sensors 2690. Memory 2630 may comprise one or more instances of instruction sequences 2632 or measurement data 2635. Logic 2660 include one or more instances of sequential functions 2651, 2652 or other components of sequence detectors 2650; event detectors 2653, 2654; timers 2656 or other logic 2657, 2658, 2659 implemented in hardware or software, for example. Actuators 2684 may comprise one or more instances of MEMS devices 2681, transducers 2682, shape memory elements 2684, or other microfluidic or other components suitable for use in situ. See, e.g., FIG. 7. Sensors 2690 may comprise one or more instances of proximity sensors 2681 or other location-indicative sensors 2682; pH sensors 2683 or other concentration-indicative sensors 2684; microphones 2685, thermometers 2686, pressure sensors 2687, or other environmental status sensors 2688; conductivity sensors 2689; or other sensors as described herein or in documents identified above.

Figure 27:
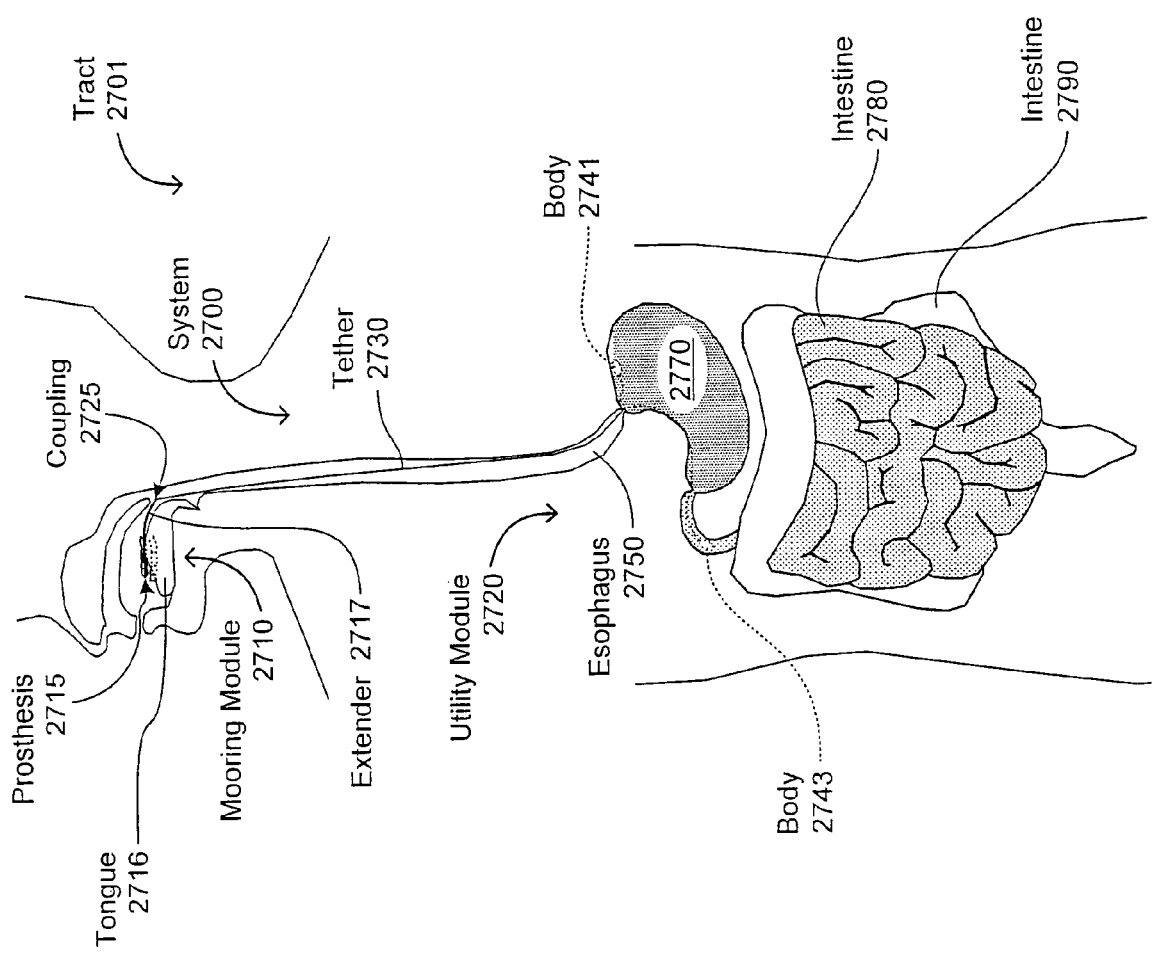

With reference now to FIG. 27, shown is a tract 2701 in a vicinity of which one or more technologies may be implemented. System 2700 may comprise one or more utility modules 2720 supported by one or more local modules 2710. Local module 2710 may, for example, comprise one or more prostheses 2715 supported at least partly by an upper portion of the subject's mouth, as shown, supporting at least an adaptable extender 2717 (over and/or beside tongue 2716, as shown) which supports one or more tethers 2730 via coupling 2725. The utility module(s) 2720 may, in various embodiments, comprise one or more bodies 2741, 2743 in esophagus 2750, gastric compartment 2770, or intestines 2780, 2790.

Body 2741 may comprise a primary material supply operable for placement within gastric compartment 2770, for example. Such bodies 2741 may occur, for example, in embodiments in which one or more tethers 2730 comprise conduits operable to guide material from the primary material supply out of the stomach. Alternatively or additionally, one or more such tethered or other bodies 2741, 2743 may comprise one or more sensors or other devices in substantially any of the variants described above.

In light of teachings herein, and referring again to FIGS. 1 & 5, those skilled in the art will recognize that any of the above-described dispensers may (optionally) be configured for use in or with a body having one or more protruding surfaces 575 overlapping one or more binding agent secretion ports 501, 502 as described herein (or as in documents identified above). Alternatively or additionally, one or more such secretion ports may likewise provide one or more therapeutic ingredients as described herein or in documents identified above.

Figure 28:
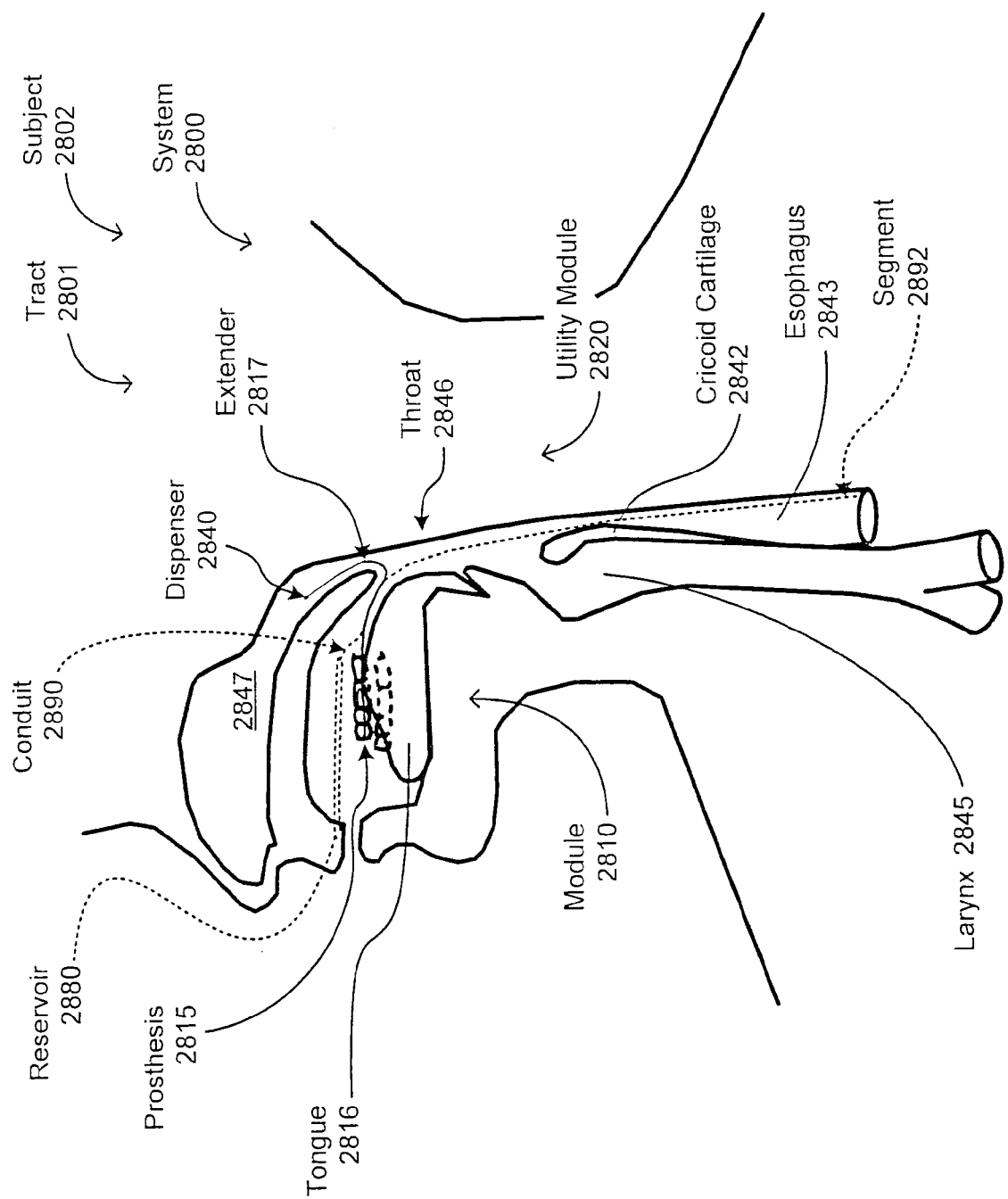

With reference now to FIG. 28, shown is a vicinity of a respiratory or digestive tract 2801 of a subject 2802 in which one or more technologies may be implemented. System 2800 may comprise one or more medical or veterinary utility modules 2820 comprising one or more dispensers 2840 or other features supported (in nasal passage 2847, for example) via one or more adaptable extender modules comprising a (rigid or other) prostheses 2815 or other support within the head and/or neck position and one or more supple extenders 2817 therefrom. Alternatively or additionally, such extenders may likewise be supported by nasal stents, surgical staples in cranial or throat positions (such as the hard palate, nasal cartilage, or cricoid cartilage 2842, for example), nasal stents, or other such local modules 2810. Exemplary structures and modes of operation may be found, for example, in U.S. patent application Ser. No. 11/417,898 ("Controllable release nasal system"), having overlapping inventors herewith, incorporated by reference herein. See also U.S. patent application Ser. No. 11/716,645 ("Orthonostric device and method of forming the same"). In some variants, extender 2817 may pass beside tongue 2816 and optionally into a side of the throat 2846 of subject 2802 with minimal interaction with the soft palate. In some variants, for example, segment 2892 may include a dispenser directed toward or extending into larynx 2845. See FIG. 20. Alternatively or additionally, one or more segments 2892 of one or more extenders 2817 may be coated along at least some of their length with an anesthetic-containing material. System 2800 may likewise comprise one or more instances of reservoirs 2880 or conduits 2890 as described below.

Such tethers or other such supple structures may extend into esophagus 2843 or other parts of subject 2802, as described further below. Dispenser 2840 may comprise one or more auditory or other sensors as described herein. Dispenser 2840 may likewise comprise one or more dispensers, particularly those having a flow path from reservoir positions at oral and/or gastric modules 141, 144 (as shown in FIG. 1). In some variants, a front portion of extender 2817 has a flexural modulus of at least about 10 megapascals. Alternatively or additionally, segment 2892 or other distal portions may have a flexural modulus of at most about 20 megapascals. Such extenders may likewise include one or more active components (not shown) operable to bend one or more coupling to keep mucous membrane irritation at an acceptably low level.

In some variants, system 2800 may include a reservoir 2880 operable to contain one or more of an antibiotic, insulin, estrogen, or some other therapeutic material within one or more reservoirs 2880 in an oral cavity of a digestive or respiratory tract 2801. Reservoir 2880 may be configured as a small tube, closed tube extending around the upper or lower gums as shown, for example, or may be positioned within the upper or lower teeth, such as above and/or below tongue 2816. Each such reservoir may include as much as 0.1-1.0 milliliters of therapeutic material or more. System 2800 may further one or more artificial conduits 2890 operable to guide the therapeutic material in one or more flows at least into a throat of tract 2801, and optionally from there into an esophagus 2843, larynx 2845, or nasal passage 2847 as shown.

In light of teachings herein, and referring again to FIG. 1, those skilled in the art will recognize that any of the above-described systems may (optionally) comprise a "first" or "second" module 125 operable to remain at least partly within a throat 149 of the digestive or respiratory tract 104 for more than a week. Any may likewise comprise such a "first" or "second" module 125, 135, operable to remain at least partly within an esophagus 150, gastric compartment 170, or intestine 180 of the digestive or respiratory tract for more than an hour. Any may likewise comprise module 144 as a "second" module operable to remain in an esophagus 150 or intestine 180 of the digestive or respiratory tract 104 for up to a week or more. Any may likewise comprise a module 144 operable to remain at least partly within an esophagus 150 or gastric compartment 170 of the digestive or respiratory tract 104 for up to a week, a month, or more as needed for a prescribed regimen.

Alternatively or additionally, any of the above-described systems may comprise a "first" and/or "second" module 125, 126 as described herein, operable to remain at least partly within a throat 149 of the digestive or respiratory tract 104 for more than a month. Any may likewise comprise such one or more such modules 125, 126 operable to engage one another by direct contact in situ and/or include one or more modules 146 comprising at least an annular structure (around a pylorus, for example).

Referring again to FIG. 3, those skilled in the art will recognize that any of the above-described systems may (optionally) include one or more actuators 321-323, 328 operable for releasing one or more therapeutic materials internally as described herein. In some variants, for example, a module 210 may include a reservoir 331 operable for releasing one or more therapeutic materials 350 into tract 301 via conduit 391, an actuator 328 operable for opening the reservoir 331, and control logic 388 configured for signaling the actuator 328 to open responsive to one or more reservoir-opening signals.

Any may likewise comprise magnetic-flux-generating elements 346 or other flux-guiding elements may (optionally) be configured to remove 2% to 20% or more of the magnetic flux passing from one module into another. Any may likewise comprise a ferromagnetic material, optionally incorporated into module 340. Any may likewise comprise such a liquid and/or gaseous propellant 377. Any may likewise have an external form 308 small enough to exit the digestive or respiratory tract 301 per vias naturales. Any of the above-described modules may (optionally) include two or more dispensers comprising respective conduits 391, 392 each operably coupled with one or more reservoirs 331, 332; and control logic 388, 389 or other circuitry operable for activating such dispensers controllably. Any of the above-described systems may comprise one or more instances of a "first" or "second" module 310 including at least a fluid-containing reservoir 333 at a higher-than-ambient pressure. Any may likewise comprise a second module 340 outside the digestive or respiratory tract 301. Any may likewise comprise a "first" or "second" module 310 operable to remain at least partly within a gastric compartment or intestine of tract 301 for more than a month and/or may comprise a material flow conduit 391 extending from module 310 at least into a throat of tract 301.

Alternatively or additionally, any of the above-described modules may include therapeutically effective amounts of an analgesic or other anti-inflammatory agent 351, an antibiotic or other antimicrobial agent 352, a hormone or other ingredients 378 as described herein. Alternatively or additionally, any of the above-described modules may include module 395 or other such adaptable extender modules. Some variants of the above-described systems may likewise comprise module 340 operable in the digestive or respiratory tract 301 to support a "first" or other module 310 as described herein directly or indirectly for a week, a month, or more in tract 301. Any may likewise include a fluid-containing reservoir 332, 333 at a higher-than-ambient pressure in situ. Any may likewise include more than one dose 337 of therapeutic material 350. Any may likewise include one or more reservoirs 332 containing one or more artificial marking agents 364 or other material 360 usable as a device-detectable marker. Any may likewise comprise a material flow conduit segment 393 extending from module 310 out of a gastric compartment of tract 301.

Alternatively or additionally, any of the above-described systems may comprise a "first" or "second" module 310, operable to remain at least partly within an esophagus, larynx, gastric compartment, or intestine of the digestive or respiratory tract 301 for more than an hour. Any may likewise comprise control logic 385 configured as a wireless-control component having at least an engaging state and a disengaging state. Any may likewise comprise a second module including one or more bioadhesives or other ingredients 365 operable for coupling with a mucous membrane as described herein. Any may likewise include one or more ingredients 353 containing a polymer and/or binding agent. Alternatively or additionally, any of the above-described modules may include a material flow path (e.g. via conduit 391) at least about one centimeter long, operable to guide material 350 more than one centimeter in a flow from one or more material reservoirs 331. Any such modules may likewise couple with or otherwise include a conduite, tether, or other material flow path (e.g. via conduit 392) of about 10 centimeters or longer, operable to guide one or more materials 350, 360, 370 selectively more than 10 centimeters in a flow from one or more reservoirs 331, 332, 333.

Referring again to FIG. 4, any of the above-described modules may (optionally) include one or more actuators 464 operable for releasing one or more therapeutic materials internally as described herein. Any of the above-described flux-guiding elements 436, 447 may be contained within (or partly within) one or more of the above-described modules. In some variants, any of the above-described modules may (optionally) be implemented as an instance of module 440: containing one or more flux-guiding elements 444-447 large enough so that the module 440 is magnetically manipulable, yet with module 440 small enough to pass through tract 104 per vias naturales. Any of the above-described modules may likewise include a medication 462 or other therapeutic material comprising at least a polymer-containing binding agent. Any may also include antenna 448 or other circuitry for transmitting measurement data 481. Substantially any of the above-described systems may (optionally) comprise module 430 operable in the digestive or respiratory tract 401 to engage at least module 440 indirectly for more than a week or month. Any may likewise comprise a "second" module 420 as described herein, including at least one material flow path 468 at least about one millimeter long.

Referring again to FIG. 5, those skilled in the art will recognize that any of the above-described modules may (optionally) include a dispenser 582, 583, optionally with circuitry for activating one or more such dispensers selectively. Any may likewise include one or more binding agents 511, 512 or other adhesives operable for coupling with a mucous membrane 513. Any of the above-described systems may comprise a "first" or "second" module (e.g. device 580) operable to engage at least a tether 578 of another module by direct contact in situ. Any may likewise include comprise a "first" or "second" module (e.g. device 580) operable to remain at least partly within the throat 149 of the digestive or respiratory tract for more than an hour. In some variants, such systems may be configured to include an adhesive, staple, ligature, or other earlier-acting attachment feature as described herein operable for coupling device 580 to mucous membrane 513; and another, later-acting attachment feature operable for initially coupling device 580 to mucous membrane 513 at least one minute after the earlier-acting attachment feature initially couples device 580 to mucous membrane 513. Alternatively or additionally, such systems may comprise a module or other device including at least binding agent 511 or some other biocompatible adhesive operable for coupling with a throat lining or other mucous membrane described herein.

Referring again to FIG. 6, any of the above-described systems may (optionally) comprise an external module 605 operable for communicating with one or more other modules 647, 648, 649 in situ. Any of the above-described modules may be adapted to include one or more sensors 652 suitable for internal use as described herein. Such modules may likewise include an electrically conductive coil 671 configured for magnetic field manipulation or other communication as described herein, either as an independent element or as a part of the above-described modules. Any such systems may further comprise a second module 680 outside the digestive or respiratory tract, such as for sending or receiving information as described herein. In some variants, such systems may comprise a second module 648 having a tethered structure.

In some contexts, implementations of the above-described systems may comprise one or more modules 647 operable to support a "first" or other module 648 as described herein directly or indirectly for more than a day in a portion 604 of a digestive or respiratory tract. Any such systems may comprise an external module 605 accessible to a caregiver operable for communicating with at least a medical or veterinary utility module 650 in situ. Any such systems may comprise a wireless-control component 651-652 (externally and/or in situ) having an engaging state, a disengaging state, and one or more other states. In some contexts, one or more of the above-described modules may be adapted to support or otherwise facilitate another module, for example, by the inclusion of one or more external modules 605, elements 640, or other devices in a proximity outside tract portion 604.

Referring again to FIG. 7, any of the above-described systems may (optionally) comprise a "first" or "second" module 740 including one or more adhesive-containing dispensers 766 operable for coupling with mucous membrane 708 by secreting an adhesive-containing material as described herein. Such a module may include sequential engagement features, sensors, dispensers, or other features as described herein also.

Referring again to FIG. 10, those skilled in the art will recognize that any of the above-described systems may (optionally) comprise one or more modules 1010, 1050 operable to remain in a gastric compartment 1070 or intestine 1080 of tract 1001 for more than a week. Any of the above-described modules may likewise include one or more dispensers 1021, module 1022, optical or other sensors, or circuitry for obtaining other measurement data. In some variants, moreover, such modules may support or otherwise facilitate another module, for example, by the inclusion of one or more external modules 1040 or other devices outside tract 1001.

Referring again to FIG. 11, any of the above-described systems may (optionally) comprise a "first" or "second" module (such as flotation module 1150, magnetic module 1160, spanning module 1180, or expandable module 1190) configured for implantation adjacent a lining of the digestive tract 1101. Any such module may likewise (optionally) implement first module 1131, small enough to pass through pylorus 1175 of a digestive tract 1101 per vias naturales. Alternatively or additionally, any of the above-described modules may comprise a belt, adhesive, or similarly supported structure for holding magnetic module 1160 adjacent the digestive or respiratory tract 1101 outside the subject. In effect, such an external configuration enables the subject to communicate with one or more modules 1131, 1135 in situ, such as by removing the structure.

Referring again to FIG. 12, any of the above-described systems may (optionally) comprise one or more modules 1220 operable to remain in a gastric compartment 1270 of tract 1201 for more than a week. Any such systems may likewise comprise one or more conduits (through or along tether 1276, for example) operable to guide nutrients or other therapeutic materials from one or more modules 1210, 1220, 1230, 1240 at least out of gastric compartment 1270 to be dispensed at another module 1275 (after settling into the intestine, for example).

Referring again to FIG. 13, any of the above-described systems may (optionally) comprise a group of modules 1310 configured for implantation in fluid 1365 adjacent a lining of the digestive or respiratory tract. Such structures may be configured to serve as a mooring module or dispenser, for example, operable to remain in the digestive tract for a month or more.

Referring again to FIG. 15, those skilled in the art will recognize that any of the above-described systems may (optionally) comprise one or more capsules 1580 or other modules 1501-1504 operable to remain in a gastric compartment (and optionally to extend into an esophagus or intestine, in some variants) for more than a week. Any such systems may likewise comprise a "first" and another module 1501, 1502 operable to engage one another by direct contact in situ.

Referring again to FIG. 20, any of the above-described systems may (optionally) comprise one or more artificial paths 2031 or other conduits operable to guide a material flow to one or more dispensers 2021, 2026 in a digestive or respiratory tract of subject 2002, at least one of which conduits exceeds 10 centimeters. Any such systems may, for example, comprise a module 2025 including at least a material flow path 2031 at least about 10 centimeters long. Such modules may include one or more sensors or a dispenser 2021, 2026 as variously described herein.

Referring again to FIG. 21, any of the above-described systems may (optionally) comprise a capsule 2109 or other module operable to remain in an esophagus or gastric compartment of the digestive or respiratory tract for more than a week. Any such module may likewise include one or more therapeutically effective doses 2132 of one or more materials 2193 as described herein. In some variants, one or more such systems may comprise a material flow conduit segment (e.g. one or more ports 2101, 2102) extending from a "first" or "second" module (e.g. capsule 2109) at least into an intestine of the digestive or respiratory tract. Alternatively or additionally, any of the above-described systems may implement system 2100 comprising a capsule 2109 or another module operable to remain in fluid 2165 of a gastric compartment or intestine for more than an hour.

In systems like those of FIGS. 3-10, any of the above-described modules may include a fluid-containing reservoir (e.g. capsule 2109) at a higher-than-ambient pressure. Alternatively or additionally, any of the above-described modules may include a material flow path (e.g. via port 2101) of about one millimeter or longer, operable to guide one or more therapeutic materials (e.g. antimicrobial agent 2173 and/or other composition 2183) more than one millimeter in a flow of one or more materials 2194, 2195 from local reservoirs.

Alternatively or additionally, any of the above-described modules may include a material flow path (e.g. via port 2102) of about one centimeter or longer, operable to guide hormone 2117 or other therapeutic material more than one centimeter in a flow from of materials 2192, 2193 from respective reservoirs. Alternatively or additionally, any of the above-described modules may include a hormone 2117, an antiviral or other antimicrobial agent 2173, an artificial marker 2156, or other materials as described herein or known to those skilled in the art.

Referring again to FIG. 22, any of the above-described modules may (optionally) include a first-therapeutic-material supply 2207 having one or more ports operable to release a therapeutic material in a first flow and a second-therapeutic-material supply 2208 having one or more ports operable to release another therapeutic material in a second, optionally simultaneous flow. This can occur, for example, in an implementation of system 2800 comprising two or more reservoir-containing modules such as is described above.

Alternatively or additionally, any of the above-described modules may be implemented in system 2200 so as to include logic 2230, antenna 2280, or other circuitry for transmitting measurement data 2218. Any such modules may likewise include a releasable dispenser 2201 or other dispensers 2202, optionally with logic 2230 or other circuitry for activating one or more such dispensers selectively. Any such modules may likewise include a releasable dispenser 2201. In some variants, moreover, such modules may include one or more antennas 2280, one or more of which may be operable for communication in a radio frequency range. Any such modules may likewise comprise one or more releasable dispensers 2201 or other releasable portions.

Referring again to FIG. 23, any of the above-described systems may (optionally) comprise a material flow conduit segment (e.g. port 2346) extending from a "first" or "second" module 2300 at least into an esophagus of the digestive or respiratory tract. Any of the above-described modules may likewise include one or more sensors 2373-2376 or other such circuitry for obtaining concentration-indicative measurement data.

Alternatively or additionally, any of the above-described systems may comprise one or more user interfaces 2310 or other remote modules operable for receiving values 2397, 2398 or other status-indicative data from sensor-containing or dispenser-containing modules 2300 in situ. Any such modules may further include one or more sensors 2371-2378 suitable for internal medical or veterinary use as described herein. In some embodiments, moreover, such modules may include one or more antennas 2357, one or more of which may be operable for communication wirelessly through living tissue. Alternatively or additionally, such modules may include one or more shape memory elements 2383 or other actuators 2380 operable for releasing one or more therapeutic materials internally as described herein as well as cameras or other components 2370 effective for obtaining auditory, colorimetric, or other measurement data.

Figure 24:
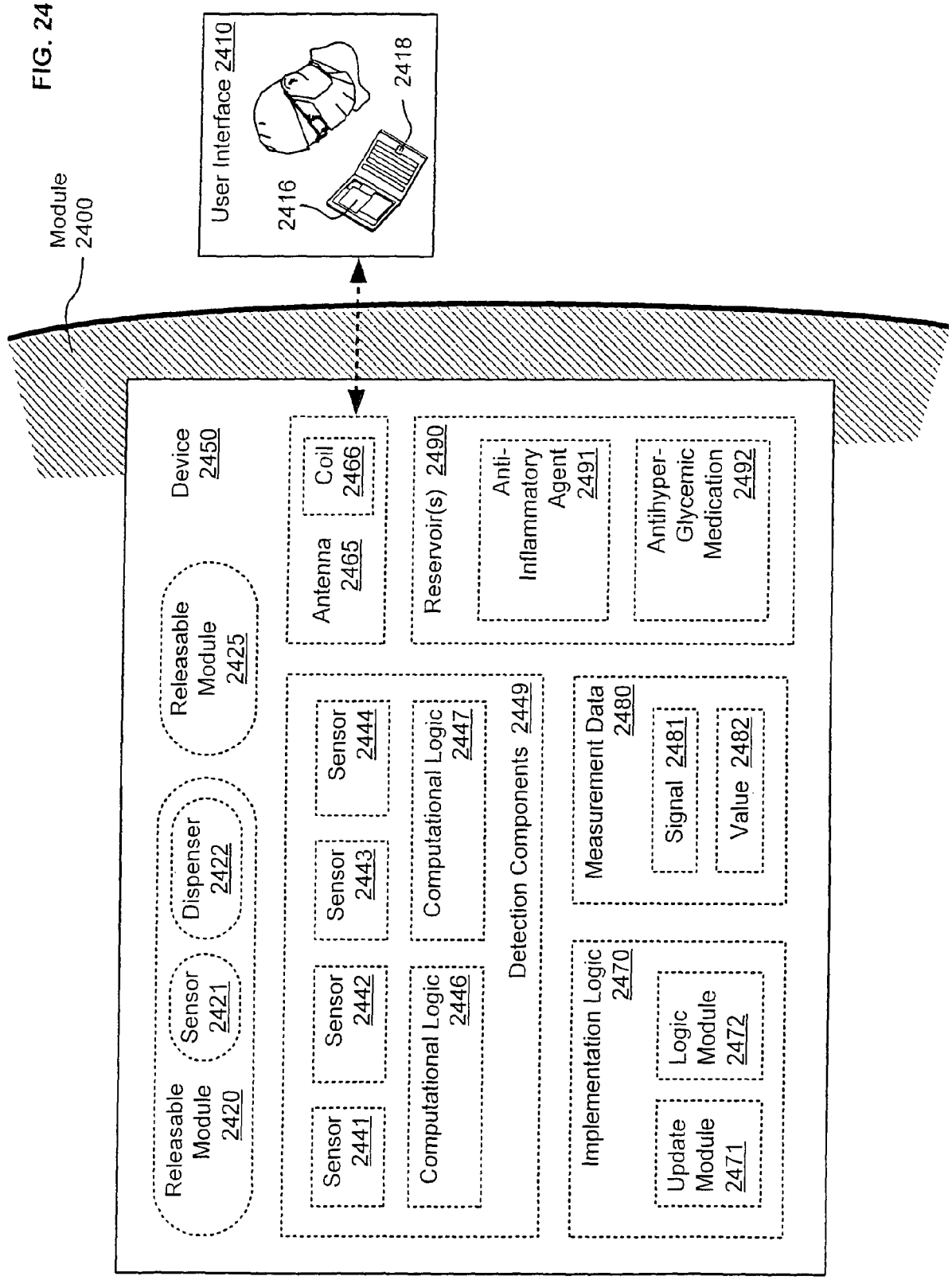

Referring again to FIG. 24, those skilled in the art will recognize that any of the above-described systems may (optionally) comprise a "first" or "second" module 2400, operable to remain at least partly within a gastric compartment or intestine of the digestive or respiratory tract for more than an hour. Such a module 2400 may (optionally) implement any of the above-described modules, and may include an electrically conductive coil 2466 configured for communication as described herein. In some variants, one or more of the above-described modules may include one or more releasable component modules 2420, 2425 or other releasable portions, one or more of which may include a sensor 2421.

Alternatively or additionally, any of the above-described systems may comprise a user interface 2410 or other external module accessible to a physician or other caregiver, such module being operable for communicating with at least one other module 2400 in situ. Such modules may include a releasable dispenser 2422 in some contexts. Alternatively or additionally, any of the above-described modules may enable or otherwise interact with other modules, for example, by the inclusion of one or more user interfaces 2410 or other devices outside a subject. In some variants, modules as described above may include therapeutically effective amounts of one or more steroids or other anti-inflammatory agents 2491, insulin and/or other antihyperglycemic medications 2492, or other useful materials as described herein. Such modules may further include one or more update modules 2471 or other update implementation circuitry responsive, for example, to medicinal regimen revisions or other remote configuration information received via user interface 2410.

Referring again to FIG. 26, any of the above-described systems may (optionally) comprise logic 2660 or other circuitry operable for activating one or more dispensers or other actuators 2684 selectively. Any such modules may likewise include extender 2717 or similarly adaptable extender modules.

Referring again to FIG. 27, any of the above-described systems may (optionally) comprise one or more bodies 2741, 2743 or some other "second" module operable to remain in a gastric compartment 2770 or intestine 2780 of the digestive tract 2701 for more than a week. In some cases, variants of the above-described modules or systems may comprise one or more conduits (through or along tether 2730, for example) operable to guide material from a utility module out of a gastric compartment. This may cause therapeutic materials as described herein to flow from one or more reservoirs in bodies 2743 upward at least into esophagus 2750, for example. In some cases, one or more of the above-described modules may likewise include a first portion containing therapeutic material in one or more bodies 2741, 2743 and a second portion (such as prosthesis 2715) supporting the first portion in an oral cavity indirectly (such as via tether 2730) for more than an hour.

Referring again to FIG. 28, any of the above-described systems may (optionally) comprise a utility module 2820 comprising segment 2892, operable to remain at least partly within an esophagus 2843 of the digestive or respiratory tract 2801 for more than an hour. Alternatively or additionally, any of the above-described modules may include a first portion containing therapeutic material in one or more reservoirs 2880 and a second portion (one or more clamps or adhesives, for example) operable supporting the first portion in an oral cavity for more than an hour.

In some variants, moreover, such systems may (optionally) comprise dispenser 2840 or other module operable to remain partly within throat 2846 and partly within nasal passage 2847 of the digestive or respiratory tract 2801 for up to a month or more. Alternatively or additionally, any of the above-described systems may comprise one or more artificial conduits 2890 operable to guide a fluid flow to dispenser 2840 or segment 2892 in tract 2801, one or more of which conduits exceeds one centimeter.

Alternatively or additionally, any of the above-described systems may comprise a dispenser 2840 or other module configured to receive at least some of a flow from one or more artificial conduits 2890. Such systems may likewise comprise one or more conduits (through or along conduit 2890, including segment 2892, for example) operable to guide one or more therapeutic materials from reservoir 2880 through gastric compartment (downward into intestine 180 via gastric compartment 170, for example). Any such systems may further include one or more self-supporting dental prostheses 2815 and/or other supportive modules.

Some or all of the embodiments described herein may generally comprise technologies for handling one or more bioactive agents and/or carriers in releasable module form, via a liquid-bearing conduit, in a mist or other spray form, in a pumped or other pressurized form, or otherwise according to technologies described herein. In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to describe devices and/or processes in the fashion set forth herein, and thereafter use engineering practices to integrate such described devices and/or processes into image processing systems. That is, at least a portion of the devices and/or processes described herein can be integrated into an image processing system via a reasonable amount of experimentation. Those having skill in the art will recognize that a typical image processing system generally includes one or more of a system unit housing, a video display device, a memory such as volatile and non-volatile memory, processors such as microprocessors and digital signal processors, computational entities such as operating systems, drivers, and applications programs, one or more interaction devices, such as a touch pad or screen, control systems including feedback loops and control motors (e.g., feedback for sensing lens position and/or velocity; control motors for moving/distorting lenses to give desired focuses. A typical image processing system may be implemented utilizing any suitable commercially available components, such as those typically found in digital still systems and/or digital motion systems.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

Those skilled in the art will recognize that it is common within the art to implement devices and/or processes and/or systems in the fashion(s) set forth herein, and thereafter use engineering and/or business practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, hovercraft, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Quest, Southwestern Bell, etc), or (g) a wired/wireless services entity such as Sprint, Cingular, Nextel, etc.), etc.

One skilled in the art will recognize that the herein described components (e.g., steps), devices, and objects and the discussion accompanying them are used as examples for the sake of conceptual clarity and that various configuration modifications are within the skill of those in the art. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, those skilled in the art will appreciate that recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A medical or veterinary system comprising:
   a first module comprising:
   at least one portion operable in a digestive or respiratory tract to engage a second module at least magnetically, the second module small enough to pass through the digestive or respiratory tract per vias naturales; and
   at least one other portion operable to support the at least one portion in an oral cavity directly or indirectly for more than a day;
   one or more artificial conduits operable to guide a therapeutic material and to extend from the first module to a digestive site or respiratory site other than the oral cavity; and
   one or more magnetic-flux-generating elements operable to diminish a disengagement force between the first module and the second module by removing at least 0.1% of a magnetic flux passing from the first module into the second module.

2. The medical or veterinary system of claim 1 in which the first module comprises:
   more than one dose of the therapeutic material.

3. The medical or veterinary system of claim 1 in which the first module further comprises:
a temperature sensor.

4. The medical or veterinary system of claim 1 in which the first module further comprises:
a material-concentration-indicative sensor.

5. The medical or veterinary system of claim 1 in which the first module further comprises:
a sensor.

6. The medical or veterinary system of claim 1 in which the first module further comprises:
an antenna.

7. The medical or veterinary system of claim 1 in which the first module further comprises:
an antihyperglycemic medication.

8. The medical or veterinary system of claim 1 in which the first module further comprises:
a polymer-containing binding agent.

9. The medical or veterinary system of claim 1 in which the first module further comprises:
an antimicrobial agent.

10. The medical or veterinary system of claim 1 in which the one or more magnetic-flux-generating elements operable to diminish the disengagement force between the first module and the second module comprise:
an electrically conductive coil.

11. The medical or veterinary system of claim 1, further comprising:
the second module, operable to remain in an esophagus, gastric compartment, or intestine of the digestive or respiratory tract for more than a day.

12. The medical or veterinary system of claim 1, further comprising:
the second module, including at least a fluid-containing reservoir at a higher-than-ambient pressure.

13. The medical or veterinary system of claim 1, further comprising:
the second module, operable to remain at least partly within a throat of the digestive or respiratory tract for more than a day.

14. The medical or veterinary system of claim 1, further comprising:
the second module, operable to engage the first module by indirect contact in situ.

15. The medical or veterinary system of claim 1, further comprising:
the second module, comprising at least a wearable and removable item.

16. The medical or veterinary system of claim 1, further comprising:
the second module, including at least an adhesive operable for coupling with a mucous membrane.

17. The medical or veterinary system of claim 1, further comprising:
circuitry for activating one or more dispensers selectively.

18. The medical or veterinary system of claim 1, further comprising:
a remote module operable for receiving status-indicative data from the first module.

19. The medical or veterinary system of claim 1, further comprising:
a ferromagnetic material.

20. The medical or veterinary system of claim 1 in which the first module further comprises:
a magnetic-flux-guiding element;
a sensor;
an antenna;
an antihyperglycemic medication including at least a polymer-containing binding agent; and
one or more actuators operable for releasing at least the antihyperglycemic medication into a material flow path at least about one millimeter long.

21. The medical or veterinary system of claim 20, further comprising:
circuitry for selectively activating at least one of the one or more actuators operable for releasing at least the antihyperglycemic medication into the material flow path extending out of a gastric compartment;
a remote module operable for receiving dispensation-status-indicative data from the first module; and
another module operable in the digestive or respiratory tract to support the second module indirectly for more than a day in the digestive or respiratory tract.

22. The medical or veterinary system of claim 1, further comprising:
circuitry for selectively activating one or more actuators operable for releasing at least an antihyperglycemic medication into a material flow path extending out of a gastric compartment;
a remote module operable for receiving dispensation-status-indicative data from the first module; and
another module operable in the digestive or respiratory tract to support the second module for more than a day in the digestive or respiratory tract.

23. The medical or veterinary system of claim 1 The medical or veterinary system of claim 1 in which the second module comprises:
at least a fluid-containing reservoir; and
a material flow path at least about one centimeter long operable to guide a material more than one centimeter in a flow from the fluid-containing reservoir.

* * * * *

UNITED STATES PATENT AND TRADEMARK OFFICE
CERTIFICATE OF CORRECTION

| | | |
|---|---|---|
| PATENT NO. | : 8,333,754 B2 | Page 1 of 1 |
| APPLICATION NO. | : 12/002777 | |
| DATED | : December 18, 2012 | |
| INVENTOR(S) | : Boyden et al. | |

It is certified that error appears in the above-identified patent and that said Letters Patent is hereby corrected as shown below:

In the Claims:

At Column 44, Line 43, following claim 23, please replace "The medical or veterinary system of claim 1 The medical or veterinary system of claim 1..." with --The medical or veterinary system of claim 1--

Signed and Sealed this
Twenty-third Day of April, 2013

Teresa Stanek Rea
*Acting Director of the United States Patent and Trademark Office*